United States Patent
Reddy et al.

(10) Patent No.: US 12,016,868 B2
(45) Date of Patent: Jun. 25, 2024

(54) BORONIC ACID DERIVATIVES AND THERAPEUTIC USES THEREOF

(71) Applicant: Qpex Biopharma, Inc., San Diego, CA (US)

(72) Inventors: Raja K. Reddy, San Diego, CA (US); Scott J. Hecker, Del Mar, CA (US)

(73) Assignee: QPEX BIOPHARMA, INC., San Diego, CA (US)

(*) Notice: Subject to any disclaimer, the term of this patent is extended or adjusted under 35 U.S.C. 154(b) by 0 days.

(21) Appl. No.: 17/048,052

(22) PCT Filed: Apr. 17, 2019

(86) PCT No.: PCT/US2019/027844
§ 371 (c)(1),
(2) Date: Oct. 15, 2020

(87) PCT Pub. No.: WO2019/204419
PCT Pub. Date: Oct. 24, 2019

(65) Prior Publication Data
US 2021/0361682 A1 Nov. 25, 2021

Related U.S. Application Data

(60) Provisional application No. 62/660,729, filed on Apr. 20, 2018.

(51) Int. Cl.
| | |
|---|---|
| A61K 31/69 | (2006.01) |
| A61K 31/407 | (2006.01) |
| A61K 31/4196 | (2006.01) |
| A61K 31/427 | (2006.01) |
| A61K 31/43 | (2006.01) |
| A61K 31/431 | (2006.01) |
| A61K 31/4439 | (2006.01) |
| A61K 31/545 | (2006.01) |
| A61K 31/546 | (2006.01) |
| A61P 31/04 | (2006.01) |
| C07F 5/02 | (2006.01) |
| C07F 5/04 | (2006.01) |

(52) U.S. Cl.
CPC ............ *A61K 31/69* (2013.01); *A61K 31/407* (2013.01); *A61K 31/4196* (2013.01); *A61K 31/427* (2013.01); *A61K 31/43* (2013.01); *A61K 31/431* (2013.01); *A61K 31/4439* (2013.01); *A61K 31/545* (2013.01); *A61K 31/546* (2013.01); *A61P 31/04* (2018.01); *C07F 5/025* (2013.01); *C07F 5/04* (2013.01)

(58) Field of Classification Search
CPC .................................. A61K 31/69; A61P 31/04
See application file for complete search history.

(56) References Cited

U.S. PATENT DOCUMENTS

| | | |
|---|---|---|
| 3,686,398 A | 8/1972 | Kohn et al. |
| 4,194,047 A | 3/1980 | Christensen et al. |
| 4,260,543 A | 4/1981 | Miller |
| 4,353,807 A | 10/1982 | Braid |
| 4,409,214 A | 10/1983 | Takaya et al. |
| 4,822,786 A | 4/1989 | Zama et al. |
| 5,442,100 A | 8/1995 | Bjorkquiest et al. |
| 5,888,998 A | 3/1999 | Maiti et al. |
| 6,184,363 B1 | 2/2001 | Shoichet et al. |
| 6,586,615 B1 | 7/2003 | Kettner et al. |
| 7,271,186 B1 | 9/2007 | Shoichet et al. |
| 7,439,253 B2 | 10/2008 | Lampilas et al. |
| 7,582,621 B2 | 9/2009 | Baker et al. |
| 7,612,087 B2 | 11/2009 | Aszodi et al. |
| 7,674,913 B2 | 3/2010 | Campbell et al. |
| 7,825,139 B2 | 11/2010 | Campbell et al. |
| 8,680,136 B2 | 3/2014 | Hirst et al. |
| 9,012,491 B2 | 4/2015 | Reddy et al. |
| 9,101,638 B2 | 8/2015 | Reddy et al. |
| 9,132,140 B2 * | 9/2015 | Reddy ..................... A61P 37/08 |
| 9,156,858 B2 | 10/2015 | Reddy et al. |
| 9,241,947 B2 * | 1/2016 | Reddy .................. A61K 31/407 |
| 9,296,763 B2 | 3/2016 | Hirst et al. |
| 9,511,142 B2 | 12/2016 | Burns et al. |
| 9,642,869 B2 | 5/2017 | Reddy et al. |
| 9,687,497 B1 | 6/2017 | Bis et al. |
| 9,694,025 B2 | 7/2017 | Hirst et al. |
| 10,004,758 B2 | 6/2018 | Hirst et al. |
| 10,085,999 B1 | 10/2018 | Gordon et al. |
| 10,206,937 B2 * | 2/2019 | Reddy .................. A61K 31/407 |
| 10,294,249 B2 | 5/2019 | Hecker et al. |

(Continued)

FOREIGN PATENT DOCUMENTS

| | | |
|---|---|---|
| CN | 102320960 A | 1/2012 |
| EP | 1550657 A1 | 7/2005 |

(Continued)

OTHER PUBLICATIONS

Drawz and Bonomo, Clincal Micorbiology Reviews, vol. 23 (1), pp. 160-201 (Year: 2010).*
Hecker et al., "Discovery of Cyclic Boronic Acid QPX7728, an Ultrabroad-Spectrum Inhibitor of Serine and Metallo-β-lactamases", J Med Chem. (Mar. 2020) 63: 7491-7507.
O'Brien et al., "Enantioselective Synthesis of Boron-Substituted Quaternary Carbons by NHC—Cu-Catalyzed Boronate Conjugate Additions to Unsaturated Carboxylic Esters, Ketones or Thioesters." J Am Chem Soc. (2010) 132(31): 10630-10633.
Reich et al., "Organoselenium chemistry. Alkylation of acid, ester, amide, and ketone enolates with bromomethyl benzyl selenide and sulfide. Preparation of selenocysteine derivatives", J Organ Chem. (1986) 51(15):2981-2988.

(Continued)

*Primary Examiner* — Craig D Ricci
*Assistant Examiner* — Janet L Coppins
(74) *Attorney, Agent, or Firm* — Knobbe, Martens, Olson & Bear, LLP

(57) ABSTRACT

Disclosed herein are antimicrobial compounds, compositions, pharmaceutical compositions, the use and preparation thereof. Some embodiments relate to boronic acid derivatives and their use a therapeutic agents.

23 Claims, No Drawings

(56) References Cited

U.S. PATENT DOCUMENTS

| | | | |
|---|---|---|---|
| 10,570,159 B2 | 2/2020 | Hecker et al. |
| 10,618,918 B2 | 4/2020 | Hecker et al. |
| 10,662,205 B2 | 5/2020 | Hecker et al. |
| 11,180,512 B2 | 11/2021 | Hecker et al. |
| 11,286,270 B2 | 3/2022 | Hecker et al. |
| 2004/0019203 A1 | 1/2004 | Micetich et al. |
| 2004/0157826 A1 | 8/2004 | Lampilas et al. |
| 2005/0020572 A1 | 1/2005 | Aszodi et al. |
| 2005/0070719 A1 | 3/2005 | Belyakov et al. |
| 2006/0019116 A1 | 1/2006 | Conley et al. |
| 2006/0178357 A1 | 8/2006 | Buynak et al. |
| 2006/0210883 A1 | 9/2006 | Chen et al. |
| 2010/0056478 A1 | 3/2010 | Desarbre et al. |
| 2010/0120715 A1 | 5/2010 | Burns et al. |
| 2010/0256092 A1 | 10/2010 | Xia et al. |
| 2010/0292185 A1 | 11/2010 | Burns et al. |
| 2011/0288063 A1 | 11/2011 | Maiti et al. |
| 2012/0040932 A1 | 2/2012 | Hirst et al. |
| 2013/0316978 A1 | 11/2013 | Reddy et al. |
| 2013/0331355 A1 | 12/2013 | Griffith et al. |
| 2013/0345172 A1 | 12/2013 | Hirst et al. |
| 2014/0194381 A1 | 7/2014 | Reddy et al. |
| 2014/0194382 A1 | 7/2014 | Reddy et al. |
| 2014/0194384 A1 | 7/2014 | Reddy et al. |
| 2014/0194385 A1 | 7/2014 | Reddy et al. |
| 2014/0194386 A1 | 7/2014 | Burns et al. |
| 2014/0206648 A1 | 7/2014 | Reddy et al. |
| 2014/0274954 A1 | 9/2014 | Chellappan et al. |
| 2015/0119363 A1 | 4/2015 | Dudley et al. |
| 2016/0220591 A1 | 8/2016 | Hirst et al. |
| 2016/0339045 A1 | 11/2016 | Griffith et al. |
| 2017/0057979 A1 | 3/2017 | Hecker et al. |
| 2017/0088561 A1 | 3/2017 | Reddy et al. |
| 2017/0136047 A1 | 5/2017 | Reddy et al. |
| 2017/0173055 A1 | 6/2017 | Bis et al. |
| 2018/0002351 A1 | 1/2018 | Hecker et al. |
| 2018/0051041 A1 | 2/2018 | Hecker et al. |
| 2018/0071325 A1 | 3/2018 | Hirst et al. |
| 2018/0207183 A1 | 7/2018 | Hirst et al. |
| 2018/0214465 A1 | 8/2018 | Hirst et al. |
| 2019/0084999 A1 | 3/2019 | Hecker et al. |
| 2019/0202832 A1 | 7/2019 | Basarab et al. |
| 2019/0211037 A1 | 7/2019 | Hecker et al. |
| 2019/0233443 A1 | 8/2019 | Hecker et al. |
| 2020/0181177 A1 | 6/2020 | Hecker et al. |
| 2022/0056055 A1 | 2/2022 | Hecker et al. |
| 2023/0144152 A1 | 5/2023 | Lamovskaya et al. |

FOREIGN PATENT DOCUMENTS

| | | | |
|---|---|---|---|
| EP | 2508506 A1 | 10/2012 | |
| EP | 2406233 B1 | 11/2013 | |
| FR | 2573070 A1 | 5/1986 | |
| JP | 2003-229277 | 8/2003 | |
| JP | 2004-291253 | 10/2004 | |
| WO | WO 1987/05297 | 9/1987 | |
| WO | WO 1989/10961 | 11/1989 | |
| WO | WO 1998/56392 A1 | 12/1998 | |
| WO | WO 2000/035904 A1 | 6/2000 | |
| WO | WO 2000/035905 A1 | 6/2000 | |
| WO | WO 2001/023374 A1 | 4/2001 | |
| WO | WO 2001/030149 | 5/2001 | |
| WO | WO 2002/022137 A1 | 3/2002 | |
| WO | WO 2002/083884 | 10/2002 | |
| WO | WO 2003/070714 | 8/2003 | |
| WO | WO 2004/039859 | 5/2004 | |
| WO | WO 2004/058679 A2 | 7/2004 | |
| WO | WO 2004/064755 A2 | 8/2004 | |
| WO | WO 2005/033090 | 4/2005 | |
| WO | WO 2005/035532 A1 | 4/2005 | |
| WO | WO 2005/087700 | 9/2005 | |
| WO | WO 2006/052733 A1 | 5/2006 | |
| WO | WO 2006/091771 | 8/2006 | |
| WO | WO 2007/058602 A2 | 5/2007 | |
| WO | WO 2007/065288 A2 | 6/2007 | |
| WO | WO 2007/095638 | 8/2007 | |
| WO | WO 2008/039420 A2 | 4/2008 | |
| WO | WO 2008/116813 A1 | 10/2008 | |
| WO | WO 2009/046098 A1 | 4/2009 | |
| WO | WO 2009/064413 A1 | 5/2009 | |
| WO | WO 2009/064414 A1 | 5/2009 | |
| WO | WO 2009/091856 A1 | 7/2009 | |
| WO | WO 2009/117540 A1 | 9/2009 | |
| WO | WO 2009/139834 A1 | 11/2009 | |
| WO | WO 2009/140309 A2 | 11/2009 | |
| WO | WO 2010/056827 A1 | 5/2010 | |
| WO | WO 2010/075286 A1 | 7/2010 | |
| WO | WO 2010/097675 A1 | 9/2010 | |
| WO | WO 2010/130708 A1 | 11/2010 | |
| WO | WO 2010/144338 A1 | 12/2010 | |
| WO | WO 2011/017125 A1 | 2/2011 | |
| WO | WO 2011/103686 A1 | 9/2011 | |
| WO | WO 2011/123502 A1 | 10/2011 | |
| WO | WO 2011/154953 | 12/2011 | |
| WO | WO 2012/021455 A1 | 2/2012 | |
| WO | WO 2012/058065 A1 | 5/2012 | |
| WO | WO 2012/067664 A1 | 5/2012 | |
| WO | WO 2012/106995 A1 | 8/2012 | |
| WO | WO 2012/136383 A1 | 10/2012 | |
| WO | WO 2013/033461 A1 | 3/2013 | |
| WO | WO 2013/053372 A1 | 4/2013 | |
| WO | WO 2013/056163 A1 | 4/2013 | |
| WO | WO 2013/092979 A1 | 6/2013 | |
| WO | WO 2013/104774 A1 | 7/2013 | |
| WO | WO 2013/104897 A1 | 7/2013 | |
| WO | WO 2013/122888 A2 | 8/2013 | |
| WO | WO 2013/184845 A1 | 12/2013 | |
| WO | WO 2014/089365 A1 | 6/2014 | |
| WO | WO 2014/107535 A1 | 7/2014 | |
| WO | WO 2014/107536 A1 | 7/2014 | |
| WO | WO 2014/110442 A1 | 7/2014 | |
| WO | WO 2014/144380 A1 | 9/2014 | |
| WO | WO 2014/151958 A1 | 9/2014 | |
| WO | WO 2015/171398 A1 | 11/2015 | |
| WO | WO 2015/171430 A1 | 11/2015 | |
| WO | WO 2015/179308 A1 | 11/2015 | |
| WO | WO 2015/191907 A1 | 12/2015 | |
| WO | WO 2016/003929 A1 | 1/2016 | |
| WO | WO 2016/065282 A1 | 4/2016 | |
| WO | WO 2016/116892 A1 | 7/2016 | |
| WO | WO 2016/149393 | 9/2016 | |
| WO | WO-2016149393 A1 * | 9/2016 | ............ A61K 31/69 |
| WO | WO 2017/100537 A1 | 6/2017 | |
| WO | WO 2018/005662 | 1/2018 | |
| WO | WO 2018/013870 A1 | 1/2018 | |
| WO | WO 2018/005662 | 4/2018 | |
| WO | WO 2019/075084 | 4/2019 | |
| WO | WO 2019/093450 A1 | 5/2019 | |
| WO | WO 2020/112542 A1 | 6/2020 | |
| WO | WO 2021/041616 A1 | 3/2021 | |

OTHER PUBLICATIONS

Rhoads et al., "The Claisen and Cope Rearrangements", Organic Reactions Chapter 1 (1975) 22: 1-166.

Stivala et al., "Highly enantioselective direct alkylation of arylacetic acids with chiral lithium amides as traceless auxiliaries." J Am Chem Soc., (2011)133(31): 11936-11939.

Tang et al., "New Chiral Phosphorus Ligands for Enantioselective Hydrogenation." Chem Rev. (2003) 103: 3029-3070.

Zhang et al., "Catalytic boracarboxylation of alkynes with diborane and carbon dioxide by an N-heterocyclic carbene copper catalyst." J Am Chem Soc. (2012) 134(35): 14314-14317.

European Extended Search Report dated Jan. 31, 2022 for Application No. 19789187.2, filed Nov. 11, 2020.

Abdel-Magid et al., "Reductive Amination of Aldehydes and Ketones with Sodium Triacetoxyborohydride: Studies on Direct and Indirect Reductive Amination Procedures", J Org Chem. (1996) 61(11):3849-3862.

Adediran et al., "A 'cephalosporin-like' cyclic depsipeptide: Synthesis and reaction with beta-lactam-recognizing enzymes", Bioorg Med Chem Lett. (1999) 9(3):341-346.

(56) References Cited

OTHER PUBLICATIONS

Aizpurua et al., "Synthesis of benzyl halides from aldehydes promoted by halosilanes and 1, 1,3,3-tetramethyldisiloxane (TMDS)", Tetrahedron Lett. (1984) 25(10):1103-1104.

Akiyama et al., "N-Hydroxy Amides. Part 6. Synthesis and Spectroscopic Properties of 1-Hydroxypiperazine-2,5-diones", J Chem Soc., Perkin Trans I, (1989) 2:235-239.

Allen et al., "Ansel's Pharmaceutical Dosage Forms and Drug Delivery Systems", 8th Edition (2004) TOC only.

Ambrose et al., Pharmacokinetics-pharmacodynamics of antimicrobial therapy: it's not just for mice anymore. Clin Infect Dis. (2007) 44: 79-86.

Ambrose et al., "Pharmacokinetics-pharmacodynamics of CB-618 in combination with cefepime, ceftazidime, ceftolozane and meropenem: the pharmacological basis for a stand-alone beta-lactamase inhibitor", Antimicrob Agents Chemother. (Nov. 2017) 61(12): e00630-17; 7 pages.

American Chemical Society. STN Chemical Database Registry RN: 1226917; Jun. 2010; 2 pages.

Arya et al., "Advances in asymmetric enolate methodology", Tetrahedron (2000) 56:917-947.

Austad et al. "Development of a multi kilogram-scale, tandem cyclopropanation ring-expansion reaction en route to hedgehog antagonist IPI-926", Org Process Res Dev., (2016) 20(4):786-798; Supporting Information, 70 pages.

Babic et al., "What's new in antibiotic resistance? Focus on beta-lactamases", Drug Res Updates (2006) 9:142-156.

Banker G.S et al. [Eds.], Modern Pharmaceutics, 4th Edition; Marcel Dekker, Inc. (2002); Chapters 9 and 10, 98 pages.

Bassetti et al., "New antibiotics for bad bugs: where are we?", Ann Clin Microbiol Antimicrob. (2013) 12:22-36.

Becker, Daniel E., "Antimicrobial Drugs", Anesth Prog (2013) 60:111-123.

Beenen et al., "Asymmetric copper-catalyzed synthesis of alpha-amino boronate esters from N-tert-butanesulfinyl aldimines", J Am Chem Soc. (2008) 130(22):6910-6911.

Berkhout et al., "Pharmacodynamics of Ceftazidime and Avibactam in Neutropenic Mice with Thigh or Lung Infection", Antimicrob Agents Chemother. (2015) 60 (1): 368-375.

Bhavani et al., Pharmacokinetic-Pharmacodynamic (PK_PD) basis for CLSI carbapenem (CARB) susceptibility breakpoint changes. abstr Abstracts of Papers, 50th Interscience Conference on Antimicrobial Agents and Chemotherapy, Sep. 12-15, 2010; #A1-1382, Boston, MA; 3 pages.

Biedrzycki et al., "Derivatives of tetrahedral boronic acids", J. Organomet. Chem. (1992) 431:255-270.

Bilello et al., "Effect of 2',3'-8 didehydro-3'-deoxythymidine in an in vitro hollow-fiber pharmacodynamic model system correlates with results of dose-ranging clinical studies", Antimicrob Agents Chemother. (1994) 38(6): 1386-1391.

Bou et al., "Cloning, nucleotide sequencing, and analysis of the gene encoding an AmpC beta-lactamase in Acinetobacter baumannii", Antimicrob Agents Chemother (2000) 44(2):428-432.

Bou et al., "OXA-24, a novel class D beta-lactamase with carbapenemase activity in an Acinetobacter baumannii clinical strain", Antimicrob Agents Chemother (2000) 44(6):1556-1561 and Erratum: Antimicrob Agents Chemother. (2006) 50(6) 2280.

Bowker et al., Comparative pharmacodynamics of meropenem using an in-vitro model to simulate once, twice and three times daily dosing in humans. J Antimicrob Chemother (1998) 42: 461-467.

Brabez et al., "Design, synthesis, and biological studies of efficient multivalent melanotropin ligands: tools toward melanoma diagnosis and treatment", J Med Chem. (2011) 54(20):7375-7384.

Braisted et al., "Discovery of a potent small molecule IL-2 inhibitor through fragment assembly", J Am Chem Soc., (2003) 125(13): 3714-3715; Supporting Information, 42 pages.

Brosz et al., "Resolution of alpha-aminoboronic esters by diastereoselective crystallization with pinanediols. Confirmation by x-ray analysis", Tetrahedron: Asymmetry (1997) 8(9):1435-1440.

Buesking et al., "Asymmetric Synthesis of Protected alpha-Amino Boronic Acid Derivatives with an Air- and Moisture-stable Cu(II) Catalyst", J Org Chem. (Mar. 2014) 79(8): 3671-3677.

Bulik et al., "Comparison of the activity of a human simulated, high-dose, prolonged infusion of meropenem against Klebsiella pneumoniae producing the KPC carbapenemase versus that against Pseudomonas aeruginosa in an in vitro pharmacodynamic model", Antimicrob Agents Chemother (2010) 54(2): 804-810.

Bundgaard H. [Ed.], "Design of Prodrugs", Elsevier (1985); TOC, 2 pages.

Bush et al., "Minireview: Updated Functional Classification of beta-Lactamases," Antimicrob Agents Chemo. (2010) 54(3):969-976.

CAS Registry No. 2005:329437 CAPLUS; "Product subclass 28: Vinylboranes", Vaultier et al., (2004); XP-002764965; 1 page.

CAS Registry Nos. 69190-59/60 (2-(bis(phenylthio)methyl)-4,4,5,5-tetramethyl-1,3,2-dioxaborolane) and 69190-60-9 (2-(bis(phenylthio)methyl)-1,3,2-dioxaborinane) Scheme 18 (2015); 2 pages.

CAS Registry No. 105892-95-3 Boronic acid [1-(phenylsulfonyl)heptyl]-, dimethyl ester (2015); 2 pages.

CAS Registry No. 831209-98-4 6H-Dibenz[c,e][1,2]oxaborin, 6a, 10a-dihydro-6-hydroxy; Entered STN: Feb. 15, 2005; 1 page.

CAS Registry No. 831210-03-8 6H-Dibenz[c,e][1,2]oxaborin, 2,4-dibromo-6a, 10a-dihydro-6-hydroxy; Feb. 15, 2005; 1 page.

CAS Registry No. 2114651-20-4; "7-Benzofurancarboxylic acid", Aurora Fine Chemicals; Aug. 16, 2017; 1 page.

CAS Registry No. 1780853-40-8; "7-Benzofurancarboxylic acid", Aurora Fine Chemicals; Jun. 15, 2015; 1 page.

CAS Registry No. 1427326-65-5; "7-Benzofurancarboxylic acid", Ellanova Laboratories; Apr. 5, 2013; 1 page.

CAS Registry No. 1344904-36-4; "7-Benzofurancarboxylic acid", Asiba Pharmatech, Inc.; Nov. 13, 2011; 1 page.

CAS Registry No. 1890373-92-8; "Benzoic acid", Aurora Fine Chemicals; Apr. 15, 2016; 1 page.

Chandrasekhar et al., "The first Corey-Chaykovsky epoxidation and cyclopropanation in ionic liquids", Tetrahedron Letts. (2003) 44:3629-3630.

Charette et al., "Palladium-catalyzed Suzuki-type cross-couplings of iodocyclopropanes with boronic acids: Synthesis of trans-1,2-dicyclopropyl alkenes", J Org Chem. (1996) 61(25): 8718-8719; Supporting Information, 52 pages.

Cheng et al., "Inhibitors of hepatitis C virus polymerase: Synthesis and characterization of novel 2-oxy-6-fluoro-N-((S)-1-hydroxy-3-phenylpropan-2-yl)-benzamides", Bioorg Med Chem Ltts. (2010) 20:2119-2124.

Cheng et al., "Synthesis of Aryl Thioethers through the N-Chlorosuccinimide-Promoted Cross-Coupling Reaction of Thiols with Grignard Reagents", J Org Chem. (2012) 77(22):10369-10374.

Chemicalland21.com. "Meglumine", Jun. 7, 2011. Downloaded from </www.chemicalland21.com/lifescience/phar/N-METHYL-D-GLUCAMINE.htm>; 2 pages.

Chinchilla et al., "Recent advances in Sonogashira reactions", Chem Soc Rev., (2011) 40: 5084-5121.

Clark et al., "Concise synthesis of the C-1-C-12 fragment of amphidinolides T1-T5", Org Biomol Chem. (2011) 9(13): 4823-4830.

Clinical and Laboratory Standards Institute (formerly NCCLS, National Committee for Clinical Laboratory Standards). "Methods for Dilution of Antimicrobial Susceptibility Tests for Bacteria That Grow Aerobically", CLSI (Jan. 2006) M7-A7 26(2), 64 pages.

Clinical and Laboratory Standards Institute (formerly NCCLS, National Committee for Clinical Laboratory Standards). "Methods for Dilution of Antimicrobial Susceptibility Tests for Bacteria That Grow Aerobically", CLSI (Jan. 2009) M07-A8 29(2), 88 pages.

Clinical and Laboratory Standards Institute (formerly NCCLS, National Committee for Clinical Laboratory Standards). "Methods for Dilution of Antimicrobial Susceptibility Tests for Bacteria That Grow Aerobically; Approved Standard—9th Edition", CLSI (Jan. 2012) M07-A9 32(2): 88 pages.

Clinical Trial NCT02168946, "A Phase 3, Multi-Center, Randomized, Open-Label Study of Carbavance (Meropenem/RPX7009) Versus Best Available Therapy in Subjects with Selected Serious

(56) References Cited

OTHER PUBLICATIONS

Infecations Due to Carbapenem-Resistant Enterobacteriaceae", 6. Oct. 2014; retrieved online from URL:https://clinicaltrials.gov/archive/NCT02168946/20140_10_06.

Conte et al., "Intrapulmonary pharmacokinetics and pharmacodynamics of meropenem", Int J Antimicrob Agents (Dec. 2005) 26(6):449-456.

Coppa et al., "A Facile, Convenient and Selective Homolytic Carbamolylation of Heteroaromatic Bases", Heterocycles (1993) 36(12):2687-2696.

Cornella et al., "Ni-catalyzed stereoselective arylation of inert C—O bonds at low temperatures". Org Lett. (2013) 15(24):6298-6301 with Supporting Information in 50 pages.

Coutts et al., "Two Efficient Methods for the Cleavage of Pinanediol Boronate Esters Yielding The Free Boronic Acids", Tetrahedron Lett. (1994) 35(29):5109-5112.

Craig Wa., "Pharmacokinetic/pharmacodynamic parameters: rationale for antibacterial dosing of mice and men", Clin Infect Dis. (1998) 26(1): 1-10.

Cunha, "Meropenem in elderly and renally impaired patients", Int'l J Antimicro Agents (1998) 10: 107-117.

Danziger et al., "Automated Site-directed Drug Design: A General Algorithm for Knowledge Acquisition about Hydrogen-bonding Regions at Protein Surfaces", Proc. Royal Soc London, Series B, Biol. Sciences (1989) 236(1283):101-113.

Darses et al., "Potassium Organotrifluoroborates: New Perspectives in organic Synthesis", Chem Rev. (2008) 108:288-325.

Davoli et al., "Enantioselective total synthesis of (−)-microcarpalide", Tetrahedron (2005) 61:4427-4436.

De Meijere A. [Ed], Science of Synthesis—vol. 24; "Three Carbon-Heteroatom Bonds: Ketene Acetals and Yne-X Compounds", TOC 46 pages.

Di Gioia et al., "Optically Pure N-Hydroxy-O-triisopropylsilyl-alpha-L-amino Acid Methyl Esters from AlCl3-Assisted Ring Opening of Chiral Oxaziridines by Nitrogen Containing Nucleophiles", J Org Chem. (2005) 70(25):10494-10501.

Dörwald F.Z., Side Reactions in Organic Synthesis—A guide to Successful Synthesis Design, Wiley-VCH Verlag Gmbh & Co. KGaA, Weinheim, Germany (2005); Preface in 4 pages.

Drawz et al., "Three Decades of beta-Lactamase Inhibitors", Clin Microbiol Reviews (Jan. 2010) 23(1):160-201.

Drusano et al., Meropenem: clinical response in relation to in vitro susceptibility. Clin Microbiol Infect. (2000) 6: 185-194.

Dunetz et al., "Large-scale applications of amide coupling reagents for the synthesis of pharmaceuticals", Org Process Res Develop. (2016) 20(2): 140-177.

Eggen et al., "Total synthesis of cryptophycin-24 (Arenastatin A) amenable to structural modifications in the C16 side chain", J Org Chem. (2000) 65(23): 7792-7799; and Supporting documents, 22 pages.

Eidam et al., "Design, synthesis, crystal structures and antimicrobial activity of sulfonamide boronic acids as beta-lactamase inhibitors", J Med Chem. (2010) 53(21):7852-7863.

Eissenstat et al., "Aminoalkylindoles: Structure-Activity Relationships of Novel Cannabinoid Mimetics", J Med Chem. (1995) 38(16):3094-3105.

El Nezhawy et al., "Synthesis and antioxidant activity of some thiazolidin-4-one derivatives", Springer; Chemical Monthly/Monatshefte für Chemie (2009) 140(5):531-539.

Endo et al., "Chemoselective Suzuki coupling of diborylmethane for facile synthesis of benzylboronates", Org Lett. (2011) 13(13):3368-3371.

Fan, et al. (2009): STN International HCAPLUS database, Columbus (OH), accession No. 2009: 425839; 6 pages.

Farquhar et al., "Intensely potent doxorubicin analogues: structure-activity relationship", J. Med. Chem. (1998) 41(6):965-972.

Ghosh et al., "Enantioselective total synthesis of (+)-largazole, a potent inhibitor of histone deacetylase", Org Lett. (2008) 10(17):3907-3909.

Giroux, A., "Synthesis of benzylic boronates via palladium-catalyzed cross-coupling reaction of bis(pinacolato)diboron with benzylic halides", Tetrahedron Lett. (2003) 44:233-235.

Goodman et al., [Eds.], "The Pharmacological Basis of Therapeutics", 8th. Edition, Pergamon Press (1990); TOC, 8 pages.

Gorovoy et al., "Boron-Containing Peptidomimetics—A Novel Class of Selective Anti-tubercular Drugs", Chem Biol Drug Des. (Jan. 2013) 81(3):408-413.

Gossinger et al., "Towards EPC-syntheses of the structural class of cochleamycins and macquarimicins. Part 3: EPC-syntheses of the beta-keto lactone subunits and first attempts towards the syntheses of the pentacyclic antibiotics of this group", Tetrahedron (2007) 63:8336-8350.

Graham et al., "D is for Drugs", Chemistry & Industry, Mar. 19, 2013, pp. 28-30, Downloaded from http://www.concertpharma.com/wp-content/uploads/2014/12/ChemistryIndustry-0313.pdf; 3 pages.

Greene, et al., "Greene's Protective Groups in Organic Synthesis", 4th Edition, (2007); pp. 774, 785 & 787.

Gunanathan et al., "Ruthenium catalyzed hydroboration of terminal alkynes to Z vinylboronates", J Am Chem Soc. (2012) 134(35): 14349-14352; Supporting Information, 32 pages.

Hall D.G., [Ed], Boronic Acids [vol. 2]: Preparations and applications in Organic Synthesis, Medicine and Materials, Wiley-VCH, Weinheim, 2nd Edition (2011); TOC.

Hama et al., "Palladium-Catalyzed alpha-Arylation of Zinc Enolates of Esters: Reaction Conditions and Substrate Scope", J Org Chem. (2013) 78(17):8250-8266.

Hartung et al., "Highly Z-selective and Enantioselective Ring Opening/Cross Metathesis Catalyzed by Resolved Stereogenic-At-Ru Complex", J Am Chem Soc. (Jul. 2013) 135(28): 10183-10185.

He et al., "Ligand-promoted borylation of C(sp3)—H bonds with palladium(II) catalysts", Angew Chem Int Ed., (2016) 55(2): 785-789.

Hecker et al., "Discovery of a Cyclic Boronic Acid beta-Lactamase Inhibitor (RPX7009) with Utility vs Class A Serine Carbapenemases", J Med Chem. (Mar. 2015) 58:3682-3692.

Higuchi et al., [Eds.] "Pro-drugs as Novel Drug Delivery Systems", ACS Sumposium Series 14 (1975); TOC, 3 pages.

Höpfl et al., "Dynamic NMR and X-ray diffraction study of (N-B)-diphenyl(2-aminoethoxy) borane derivatives of ephedrines and pseudoephedrines". J Organomet Chem. (1997) 544(2):175-188.

Hoveyda A., "Evolution of catalytic stereoselective olefin metathesis: From ancillary transformation to purveyor of stereochemical identity", J Org Chem. (Jun. 2014) 79(11): 4763-4792.

Hu et al., "Ag(I)-catalyzed C—H borylation of terminal alkynes", Tetrahedron (2014) 70: 5815-5819.

Imanishi et al., "Discovery of a Novel Series of Biphenyl Benzoic Acid Derivatives as Potent and Selective Human beta3-Adrenergic Receptor Agonists with Good Oral Bioavailability. Part I", J Med Chem. (2008) 51(6):1925-1944.

Inglis et al., "Observations on the Deprotection of Pinanediol and Pinacol Boronate Esters via Fluorinated Intermediates", J Org Chem. (2010) 75(2):468-471; Supporting Information, S1-S-76.

Ishii et al., "In vitro potentiation of carbapenems with ME1071, a Novel metallo-β-lactamaselinhibitor, against metallo-β-lactamase producing pseudomonas aeruginosa clinical isolates." Antimicrob. Agents Chemother. doi:10.1128/AAC.01397-09 (2010) 54(9):3625-3629.

Ishiyama et al., "Palladium(0)-catalyzed cross-coupling reaction of alkoxydiboron with haloarenes: A direct procedure for arylboronic esters", J Org Chem. (1995) 60(23): 7508-7510; Supporting Information, 35 pages.

Ito et al., "An efficient constructive method for a tricyclic system: an important intermediate for the synthesis of tricycloclavulone", Tetrahedron Lett. (2003) 44:1259-1261.

Jadhav et al., "Direct synthesis of [alpha-[(tert-Butoxycarbonyl)amino]alkyl]- boronates from (alpha-Haloalkyl)boronates", Org Chem. (1996) 61(22):7951-7954.

Jagannathan et al., "Synthesis of Boronic Acid Analogues of alpha-Amino Acids by Introducing Side Chains as Electrophiles", J Org Chem. (2001) 66(19):6375-6380.

(56) References Cited

OTHER PUBLICATIONS

Jang et al., Copper-catalyzed trans-hydroboration of terminal aryl alkynes: Stereodivergent synthesis of alkenylboron compounds. Org Letts. (2016) 18(6): 1390-1393; Supporting Information in 37 pages.
Jarrett et al., "Nickel(II) bis(phosphine) complexes". Inorg Chem. (1991) 30(9):2098-2104 with Supporting Information in 7 pages.
Jiang et al., "A Practical Synthesis of Cefcapene Pivoxil", Synthesis (2012) 44:207-214.
Johnson et al., "A drug targeting motif for glycosidase inhibitors: An iminosugar-boronate shows unexpectedly selective beta-galactosidase inhibition", Tetrahed Lttrs. (2002) 43(49):8905-8908.
Jordan V.C., "Tamoxifen: A most unlikely pioneering medicine", Drug Discovery (2003) 2:205-213.
Kabalka et al., "Synthesis of a series of bornonated unnatural cyclic amino acids as potential boron neutron capture therapy agents", Appl Organomet Chem. (2008) 22(9):516-522.
Kanai et al., "Synthesis of ortho-Acylbenzylboronates via Cross-Coupling Reaction of (Dialkoxyboryl)methylzinc Reagents with Haloarenes. A Stable ortho-Quinodimethane Precursor", Chem Letts. (1993) 22(5):845-848.
Kawamorita et al., "Synthesis of Primary and Secondary Alkylboronates through Site-Selective C(sp3)-H Activation with Silica-supported Monophosphine-Ir Catalysts", J Am Chem Soc. (2013) 135(8):2947-2950.
Kikuchi et al., "Comparison of the Pharmacodynamics of Biapenem in Bronchial Epithelial Lining Fluid in Healthy Volunteers Given Half-Hour and Three-Hour Intravenous Infusions", Antimicrob Agents Chemother. (Jul. 2009) 53(7):2799-2803.
Kint et al., "New-found fundamentals of bacterial persistence", Trends Microbiol. (2012) 20(12):577-585.
Kinuta et al., "Rhodium-catalyzed borylation of aryl 2-pyridyl ethers through cleavage of the carbon-oxygen bond: borylative removal of the directing group". J Am Chem Soc. (2015) 137(4):1593-1600 with Supporting Information in 198 pages.
Kondo et al., Ruthenium-Catalyzed Monoalkenylation of Aromatic Ketones by Cleavage of Carbon-Heteroatom Bonds with Unconventional Chemoselectivity. Angew Chem Int Ed Engl. (2015) 54(32):9293-9297 with Supporting Information in 95 pages.
Kose et al., "Synthesis of photochromic 2,3-bis(5-methyl-2-phenyl-4-thiazolyl)-1,4-naphthoquinone derivatives", J Photochem Photobiol. A: Chemistry. (2011) 219(1):58-61.
Kotha et al., "Recent applications of the suzuki-miyaura cross-coupling reaction in organic synthesis", Tetrahedron (2002) 58:9633-9695.
Kuang et al., "Convenient and stereoselctive synthesis of (Z)-1-bromo-1-alkenes by microwave-induced reaction", Tetrahedron Letts. (2001) 42(23): 3893-3896.
Kumar et al., "Synthesis of intermediates for the lactone moiety of mevinic acids via tellurium chemistry", J. Org. Chem., (1994) 59(17):4760-4764.
Kumar et al., "Development of Practical Methodologies for the Synthesis of Functionalized Benzoboroxoles", Tetrahedron Lett. (Aug. 25, 2010) 51(34):4482-4485.
Kusakabe et al., "Preparation of Optically Acitve 2-Furylcarbinols by Kinetic Resolution Using the Sharpless Reagent and Their Application in Organic Synthesis", J org Chem (1989) 54(9):2085-2091.
Kuti et al., "Use of Monte Carlo simulation to design an optimized pharmacodynamic dosing strategy for meropenem", J Clin Pharmacol. (Oct. 2003) 43(10): 1116-1123 with Erratum (2005); 1 page.
Laitar et al., "Catalytic diboration of aldehydes via insertion into the copper-boron bond", J Am Chem Soc. (2006) 128(34):11036-11037.
Lapuebla et al., "Activity of Meropenem Combined with RPX7009, a Novel beta-LactamaseInhibitor, against Gram-Negative Clinical Isolates in New York City", Antimicrob Agents Chemother. (Aug. 2015) 59(8):4856-4860.
Larock R. [Ed.] Comprehensive Organic Transformations, VCH Publishers 1989; TOC, 11 pages.

Lebel et al., "Boc-protected amines via a mild and efficient one-pot Curtius rearrangement", Org Letts. (2005) 7(19): 4107-4110.
Lee et al., "Vicinal Diboronates in High Enantiomeric Purity through Tandem Site-Selective NHC-Cu-Catalyzed Boron-Copper Additions to Terminal Alkynes", J Am Chem Soc. (Dec. 2009) 131(51):18234-18235.
Lee et al., "Comparison of 30-min and 3-h infusion regimens for imipenem/cilastatin and for meropenem evaluated by Monte Carlo simulation", Diagn Microbiol Infect Dis. (2010) 68: 251-258.
Li et al., "Population Pharmacokinetic Analysis and Dosing Regimen Optimization of Meropenem in Adult Patients", J Clin Pharmacol. (2006) 46(10): 1171-1178.
Li et al., "Novel macrocyclic Hcv NS3 protease inhibitors derived from α-amino cyclic boronates", Bioorganic Med Chem Lett. (2010) 20:5695-5700.
Li et al., "Synthesis and evaluation of novel alpha-amino cyclic boronates as inhibitors of HCV NS3 protease", Bioorg Med Chem Lett. (2010) 20:3550-3556.
Li et al., "Stereoselective total synthesis of etnangien and etnangien methyl ester", J Org Chem. (2010) 75(8):2429-2444.
Liang et al., "The Efficient Copper(I) (Hexabenzyl)tren Catalyst and Dendritic Analogues for Green "Click" Reactions between Azides and Alkynes in Organic Solvent and in Water: Positive Dendritic Effects and Monometallic Mechanism", Advance Syn Catal. (2011) 353(18): 3434-3450.
Lieberman H.A. [Ed] Pharmaceutical Dosage Forms—Tablets; Marcel Dekker, Inc. (1989) 2nd Ed; TOC; 7 pages.
Lima et al., "Bioisosterism: A Useful Strategy for Molecular Modification and Drug Design", Curr Med Chem. (2005) 12:23-49.
Lin et al., "Enantioselective syn and anti homocrotylation of aldehydes: Application to the formal synthesis of spongidepsin", J Am Chem Soc. (2015) 137(40): 13176-13182; Supporting Information, 177 pages.
Liu et al., "Selective Protein tyrosine phosphatase 1B inhibitors: Targeting the second phosphotyrosine binding site with non-carboxylic acid-containing ligands", J Med Chem. (2003) 46(16):3437-3440; Supporting Information, 38 pages.
Liu et al., "Application of Stereoselective Ether Transfer to the Synthesis of Isotactic Polyethers", J Org Chem. (2010) 75(12):3953-3957.
Livermore et al., "Activities of NXL104 combinations with Ceftazidime and Aztreonam against Carbapenemase-producing Enterobacteriaceae", Antimicr Agents Chemother. (2011) 55(1):390-394.
Livermore et al., "Activity of biapenem (RPX2003) combined with the boronate beta-lactamase inhibitor RPX7009 against carbapenem-resistant Enterobacteriaceae", J Antimicrob Chemother. (Aug. 2013) 68(8):1825-1831.
Lodise et al., "Penetration of meropenem into epithelial lining fluid of patients with ventilator-associated pneumonia", Antimicrob Agents Chemother. (Apr. 2011) 55(4):1606-1610.
Louie et al., Impact of meropenem in combination with tobramycin in a murine model of Pseudomonas aeruginosa pneumonia. Antimicrob Agents Chemother (2013) 57: 2788-2792.
Luithle et al., "Synthesis of enantiomerically pure cis-cyclopropylboronic esters", Eur J Org Chem. (2000) 14: 2557-2562.
MacVane et al., Characterizing in vivo pharmacodynamics of carbapenems against Acinetobacter baumannii in a Murine thigh infection model to support breakpoint determinations. Antimicrob Agents Chemother (2014) 58: 599-601.
Maguire B. A., Inhibition of Bacterial Ribosome Assembly: a Suitable Drug Target? Microbiol Mol Biol Rev. (2009) 73(1):22-35.
Malfertheiner et al., "Current concepts in the management of Helicobacter pylori infection: the Maastricht III Consensus Report", Gut (2007) 56(6):772-781.
Matteson et al., "Iodomethaneboronic Esters and Aminomethaneboronic Esters", J Organomet. Chem. (1979) 170:259-264.
Matteson et al., "A Directed Chiral Synthesis of Amino Acids from Boronic Esters", Tetrahedron Lett. (1987) 28(39):4499-4502.
Matteson, D.S., "Asymmetric Synthesis with Boronic Esters", Acc Chem Res. (1988) 21(8):294-300.
Matteson, "Boronic esters in stereodirected synthesis", Tetrahedron (1989) 45(7):1859-1885.

(56) References Cited

OTHER PUBLICATIONS

Matteson et al., "A stereospecific convergent coupling of nucleophilic and electrophilic chiral carbons", J. Am. Chem. Soc. (1989) 111:4399-4402.
Matteson et al., "Synthesis of asymmetrically deuterated glycerol and dibenzylglyceraldehyde via boronic esters", J. Am. Chem. Soc. (1990) 112:3964-3969.
Matteson et al., "(Alkoxyalkyl)boronic Ester Intermediates for Asymmetric Synthesis", Organometallics (1996) 15:152-163.
Matteson, "Alpha-Halo Baronic Esters in Asymmetric Synthesis", Tetrahedron (1998) 54(36):10555-10607.
Matteson et al., "Glass-Catalyzed Conversion of Boronic Esters of Asymmetric Diols to Diol Sulfites and Amine Complexes of Boron Halides", Oranometallics (2001) 20(13):2920-2923 & supporting Information (9 pages).
Matteson et al., "Cesium Alkyltrifluoroborates from Asymmetric Boronic Esters", Synlett (Jul. 2006) 20:3501-3503.
Matteson et al., "Synthesis of a (Beta-acetamido-alpha-acetoxyethyl) boronic ester via azido boronic esters", J Organomet Chem. (2008) 693:2258-2262.
Matteson, "Boronic Esters in Asymmetric Synthesis", J Org Chem. (Oct. 2013) 78(20): 10009-10023.
McOmie J.R.W. [Ed], Protective Groups in Organic Chemistry, Plenum Press, London & New York (1973); TOC, 3 pages.
Meanwell, "Synopsis of some recent tactical application of bioisosteres in drug design", J. Med. Chem. (2011) 54:2529-2591.
McSharry et al., "Prediction of the pharmacodynamically linked variable of oseltamivir carboxylate for influenza A virus using an in vitro hollow-fiber infection model system", Antimicrob Agents Chemother (2009) 53(6): 2375-2381.
Mendoza et al., "Bis(phenylthio)methaneboronic Esters as Sources of Carbanions and Ketene Thioacetals", J Org Chem. (1979) 44(8):1352-1354.
Micalizio et al., "A Boronic Ester Annulation Strategy for Diversity-Oriented Organic Synthesis", Angew Chem Int Ed Engl. (2002) 41(1):152-154.
Miriagou et al., "Acquired carbapenemases in Gram-negative bacterial pathogens: detection and surveillance issues", Clin Microbiol Infect. (Feb. 2010) 16(2):112-122.
Mkhalid et al., "C—H activation for the construction of C—B bonds", Chem Rev. (2010) 110(2): 890-931.
Molander et al., "Highly stereoselective synthesis of cis-alkenyl pinacolboronates and potassium cis-alkenyltrifluoroborates via a hydroboration/protodeboronation approach", J Org Chem. (2008) 73(17): 6841-6844.
Montalbetti et al., "Amide bond formation and peptide coupling", Tetrahedron (2005) 61:10827-10852.
Montefour et al., "Acinetobacter baumannii: an emerging multidrug-resistant pathogen in critical care", Crit Care Nurse (2008) 28(1): 15-25.
Morandi et al., "Structure-based optimization of cephalothin-analogue boronic acids as beta-lactamase inhibitors", Bioorg Med Chem. (2008) 16(3):1195-205. Epub Nov. 7, 2007.
Mori et al., "Synthesis of 1,3-dienes from alkynes and ethylene: Acetic acid 2-methylene-3-phenethylbut-3-enyl ester", Org Synth. (2005) 81: 1-13.
Morrill et al., "Treatment Options for Carbapenem-Resistant Enterobacteriaceae Infections", Open Forum Infectious Diseases [OFID] Apr. 2015; 15 pages.
Munar et al., "Drug Dosing Adjustments in Patients with Chronic Kidney Disease", Am Fam Physician (May 2007) 75(1): 1487-1496.
Nema et al., "Excipients and Their Role in Approved Injectable Products: Current Usage and Future Directions", PDA J Pharm Sci Technol. (2011) 65(3):287-332.
Ness et al., "Structure-based design guides the improved efficacy of deacylation transition state analogue inhibitors of TEM-1 beta-Lactamase", Biochemistry (2000) 39(18):5312-5321.
Nicasio et al., "Pharmacokinetics-Pharmacodynamics of Tazobactam in Combination with Piperacillin in an In Vitro Infection Model", Antimicrob Agents Chemother. (2016) 60: 2075-2080. doi: 10.1128/AAC.02747-15.
Nicolau Dp., "Pharmacokinetic and pharmacodynamic properties of meropenem", Clin Infect Dis. (2008) 47 Suppl 1: S32-S40.
Noguchi et al., "Boron-masking strategy for the selective synthesis of oligoarenes via iterative Suzuki-Miyaura coupling", J Am Chem Soc. (2007) 129(4): 758-759; Supporting Information, 46 pages.
Nordmann et al., How to Detect NDM-1 Producers, J. Clin. Micro. (2011) 49:718-721.
Overman et al., "Organic Synthesis—Working with Hazardous Chemicals", Org Synth. (1990) 68: 182; 5 pages.
Panek et al., "Diastereoselectivity in the borane methyl sulfide promoted hydroboration of .alpha.-alkoxy-.beta, gamma.-unsaturated esters. Documentation of an alkoxy-directed hydroboration reaction", J. Org. Chem. (1992) 57(20):5288-5290.
Paquette L.A. [Ed.] Encyclopedia of Reagents for Organic Synthesis, vol. 1; J. Wiley & Sons (1995); Cover Only.
Patani et al., "Bioisosterism: A Rational Approach in Drug Design", Chem Rev. (1996) 96:3147-3176.
Paterson et al., "Extended-Spectrum beta-Lactamases: a Clinical Update", Clin Microbiol Rev. (2005) 18(4):657-686.
Pellissier, H., "Recent developments in asymmetric cyclopropanation", Tetrahedron (2008) 64(30-31): 7041-7095.
Perez et al., "Why are we afraid of Acinetobacter baumannii?", Expert Rev Anti Infect Ther. (2008) 6(3): 269-71.
Pietruszka et al., "Enantiomerically pure cyclopropylamines from cyclopropylboronic esters", Eur J Org Chem. (2009) 34: 5998-6008.
Pine et al., "Resonance vs. Tautomerism" in Organic Chemistry; McGraw-Hill, New York 4th Ed. (1980), pp. 218-219.
Pintaric et al., "An Opportunity for Mg-Catalyzed Grignard-Type Reactions: Direct Coupling of Benzylic Halides with Pinacolborane with 10 mol % of Magnesium", J Am Chem Soc. (2010) 132(34): 11825-11827.
Powell et al., "Compendium of excipients for parenteral formulations", PDA J Pharm Sci Technol. (1998) 52(5):238-311.
Queenan et al., "Carbapenemases: the Versatile β-Lactamases", Clin Microbiol Rev. (Jun. 2007) 20(3): 440-458.
Rehm et al., "*Staphylococcus aureus*: Methicillin-susceptible *S. aureus* to Methicillin-resistant *S. aureus* and Vancomycin-resistant S. aureus", Clin Inf Diseases. (2010) 51(S2):S176-S182.
Reissig et al., "High diastereoselection in the alkylation of siloxy-substituted methyl cyclopropanecarboxylates: consequence of a pyramidal ester enolate anion?", J. Am. Chem. Soc. (1982) 104:1735-1737.
Robak et al., "Synthesis and applications of tert-butanesulfinamide", Chem Rev. (2010) 110(6):3600-3740.
Roche, E.B. (Ed.)., Bioreversible Carriers in Drug Design: Theory and Application. New York: Pergamon Press (1987); pp. 14-21.
Rodriguez-Martinez et al., "VIM-19, a Metallo-beta-lactamase with increased Carbapenemase Activity from *Escherichia coli* and Klebsiella pneumoniae", Antimicro Agents Chemother. (2010) 54(1):471-476.
Rosen et al., "Nickel-catalyzed cross-couplings involving carbon-oxygen bonds". Chem Rev. (2011) 111(3):1346-1416.
Rubino et al., "Phase 1 Study of the Safety, Tolerability, and Pharmacokinetics of Vaborbactam and Meropenem Alone and in Combination following Single and Multiple Doses in Healthy Adult Subjects", Antimicrob Agents Chemother. (Apr. 2018) 62(4): E02228-17; 12 pages.
Sabet et al., "In Vivo Efficacy of Carbavance (Meropenem/RPX7009) Against KPC-producing Enterobacteriaceae", Abstracts of the 54th Interscience Conference on Antimicrobial Agents and Chemotherapy (Sep. 5-9, 2014) F-958; 3 pages.
Sabet et al., "Activity of Simulated Human Dosage Regimens of Meropenem and Vaborbactam against Carbapenem-Resistant Enterobacteriaceae in an In Vitro Hollow-Fiber Model", Antimicrob Agents Chemother (2017) 62. pii: e01969-17. doi: 10.1128/AAC.01969-17.
Sabet et al., "Activity of Meropenem-Vaborbactam in Mouse Models of Infection Due to KPC-Producing Carbapenem-Resistant Enterobacteriaceae", Antimicrob Agents Chemother. (2017) 62:1 10 e01446-379 17.

(56) References Cited

OTHER PUBLICATIONS

Saito et al., "Nickel-catalyzed boron insertion into the C2—O bond of benzofurans". J Am Chem Soc. (2016)., 138(47), 15315-15318 with Supporting Information in 103 pages.

Sawant et al., "Synthesis of the C1-C13 Fragment of Biselyngbyaside", Synlett (2011) 20: 3002-3004.

Sawyer et al., "Physical properties and synthetic utility of a-*alkoxyorganolithium* species as studied through ligand selectivity in tin-lithium exchange", J. Am. Chem. Soc. (1988) 110:842-853.

Schwarzer et al., "Combined theoretical and experimental studies of nickel-catalyzed cross-coupling of methoxyarenes with arylboronic esters via C—O bond cleavage". J Am Chem Soc. (2017) 139(30):10347-10358 with Suppl. Information in 255 pages.

Scriven et al., "Azides: Their preparation and synthetic uses", Chem Rev. (1988) 88(2): 297-368.

Selander et al., "Palladium-catalyzed allylic C—OH functionalization for efficient synthesis of functionalized allylsilanes", J Am Chem Soc. (2011) 133(3):409-411.

Shaffer, Robyn Kroop, "The Challenge of Antibiotic-Resistant *Staphylococcus*: Lessons from Hospital Nurseries in the mid-20th Century", Yale J Biol Med. (2013) 86:261-270.

Shao et al., "Asymmetric hydrogenation of 3,5-Dioxoesters catalyzed by Ru-binap complex: A short step asymmetric synthesis of 6-substituted 5,6-dehydro-2-pyrones", Tetrahedron (1993) 49(10):1997-2010.

Singer et al., "Catalytic, enantioselective acetate aldol additions to alpha-, beta-ynals: Preparation of optically active propargylic alcohols", Tetrahedron (1998) 54(25): 7025-7032.

Singh et al., "Asymmetric Homologation of Boronic Esters Bearing Azido and Silyloxy Substituents", J Org Chem. (2000) 65(20):6650-6653 and Erratum: J Org Chem. (2001) 66(22):7560.

Singh et al., "Confronting the challenges of discovery of novel antibacterial agents", Bioorg Med Chem Lett. (2014) 24(16):3683-3689.

Sliwka et al., "Synthetic Sulfur Carotenoids II: Optically Active Carotenoid Thiols", Tetrahedron: Asymmetry (1993) 4(3):361-368.

Solladiéet al., "First Stereocontrolled Synthesis of the (3S,5R,7R,10R,11R)-C1-C13 Fragment of Nystatin A(1)", J Org Chem. (1999) 64(15):5447-5452.

Souto et al., "Synthesis and biological characterization of the histone deacetylase inhibitor largazole and c7-modified analogues", J. Med. Chem. (2010) 53(12):4654-4667.

Spiegel et al., "CP-263, 114 synthetic studies. Construction of an isotwistane ring system via rhodium carbenoid C—H insertion", Tetrahedron (2002) 58:6545-6554.

Sumida et al., "Boron-selective biaryl coupling approach to versatile dibenzoxaborins and application to concise synthesis of defucogilvocarcin M", Org Lttr. (Dec. 2014) 16(23):6240- 6243.

Sun et al., "A method for the deprotection of alkylpinacolyl boronate esters", J Org Chem. (2011) 76(9): 3571-3575; Supporting Information, 8 pages.

Sun et al., "Programmed Synthesis of a Contiguous Stereotriad Motif by Triple Stereospecific Reagent-controlled Homologation", Org Lttr. (Jul. 2013) 15(17):4500-4503.

Tam et al., "Optimization of meropenem minimum concentration/MIC ratio to suppress in vitro resistance of Pseudomonas aeruginosa", Antimicrob Agents Chemother. (2005) 49(12): 4920-4927.

Teo et al., "Efficient and highly aldehyde selective Wacker oxidation", Org Lett. (2012) 14(13):3237-3239.

Theuretzbacher et al., "Update on antibacterial and antifungal drugs—can we master the resistance crisis?", Curr Opin Pharmacol. (2011) 11:429-432.

Tobisu et al., "Nickel-catalyzed alkylative cross-coupling of anisoles with Grignard reagents via C—O bond activation". J Am Chem Soc. (2016) 138(47):6711 and Suppl. Information in 105 pages.

Ty et al., "Synthesis and biological evaluation of enantiomerically pure cyclopropyl analogues of combretastatin A4". Bioorg Med Chem (2013) 21:1357-1366.

U.S. Department of Health and Human Resources, "Antibiotic Resistance Threats in the United States, 2013"; 114 pages.

Valters et al., "Ring-Chain Tautomerism", Plenum Press, New York and London, Softcover reprint of the hardcover 1st Ed. 1985, Chapter 1, 23 pages.

VanScoy et al., "Pharmacokinetics-pharmacodynamics of tazobactam in 386 combination with ceftolozane in an in vitro infection model", Antimicrob Agents Chemother. (2013) 57: 2809-2814. doi: 10.1128/AAC.02513-12.

Vasil'Ev et al., (1977): STN International HCAPLUS database, Columbus (OH), accession No. 1977: 72730; 1 page.

Vitor et al., "Rhenium(I)- and technetium(I) tricarbonyl complexes anchored by bifunctional pyrazole-diamine and pyrazole-dithioether chelators", J Organometal Chem (2004) 689(25): 4764-4774.

Voituriez et al., "Preparation of a storable zinc carbenoid species and its application in cyclopropanation, chain extension, and [2,3]-sigmatropic rearrangement reactions", J Org Chem. (2010) 75(4): 1244-1250; Supporting Information, 20 pages.

Waley, Stephen G., "A quick method for the determination of inhibition constants", Biochem J. (1982) 205(3):631-633.

Walker et al., "Pharmacodynamic activities of meropenem in an animal infection model", (1994), Abstracts of Papers #A91, 34th Interscience Conference on Antimicrobial Agents and Chemotherapy, Orlando , FL., 5 pages.

Walsh et al., "Metallo-beta-Lactamases: the Quiet before the Storm?", Clin Microbiol Rev. (2005) 18(2):306-325.

Wang et al., "Recognition and resistance in TEM beta-lactamase", Biochemistry (2003) 42(28):8434-8444.

Webb et al., "Metal catalysed hydroboration of vinyl sulfides, sulfoxides, sulfones, and sulfonates", J Mol Cat A: Chem. (2007) 275:91-100.

Wenkert et al., "Nickel-induced conversion of carbon-oxygen into carbon-carbon bonds. One-step transformations of enol ethers into olefins and aryl ethers into biaryls".(1979) 101(8):2246-2247.

Wilson D.N., "The A-Z of bacterial translation inhibitors", Crit Rev Biochem Mol Biolog. (2009) 44(6):393-433.

Wohlrab et al., "Total synthesis of plusbacin A3: a depsipeptide antibiotic active against vancomycin-resistant bacteria", J. Am. Chem. Soc. (2007) 129:4175-4177.

Wong et al., "A chemoselective Reformatsky-Negishi approach to α-haloaryl esters", Tetrahedron (2014) 70(7): 1508-1515.

Xia et al., "Synthesis and SAR of novel benzoxaboroles as a new class of beta-lactamase inhibitors", Bioorg Med Chem Lett. (2011) 21:2533-2536.

Xie et al., "Group-assisted purification (GAP) chemistry for the synthesis of Velcade via asymmetric borylation of N-phosphinylimines", Beilstein J Org Chem (Mar. 2014) 10:746-751.

Yamamoto et al., "Iridium-catalyzed hydroboration of alkenes with pinacolborane", Tetrahedron (2004) 60:10695-10700.

Yanagisawa et al., "Nonpeptide angiotensin II receptor antagonists: synthesis, biological activities, and structure-activity relationships of imidazole-5-carboxylic acids bearing alkyl, alkenyl, and hydroxyalkyl substituents at the 4-position and their related compounds", J Med Chem. (1996) 39(1):323-338.

Yuen et al., "Deprotection of pinacolyl boronate esters via hydrolysis of intermediate potassium trifluoroborates", Tetrahed Lttr. (2005) 46(46):7899-7903.

Zhu et al., "Design, preparation, x-ray crystal structure, and reactivity of o-alkoxyphenyliodonium bis(methoxycarbonyl)methanide, a highly soluble carbene precursor", Org Lett. (2012) 14(12): 3170-3173; Supporting Information, 76 pages.

International Search Report and Written Opinion dated Jul. 8, 2019 for International Application No. PCT/US2019/027844, filed Apr. 17, 2019.

Balbach et al., "Pharmaceutical evaluation of early development candidates 'the 100 mg-approach'", Int'l J Pharma. May 4, 2004;275: 1-12.

CAS Registry No. 2006320-60-9; "3,4-dihydro-2-hydroxy-2H-1,2-Oxaborino[6,5-c]pyridine-8-carboxylic acid", CAS, Oct. 5, 2016; 1 page.

CAS Registry No. 2170834-63-4; 'Benzo[e]cycloprop[c][1,2]oxaborin-4-carboxylic acid, 5-fluoro-1,1a,2,7b-tetrahydro-2-hydroxy-, (1aR,7bS); Jan. 23, 2018; 1 Page.

(56) References Cited

OTHER PUBLICATIONS

CAS Registry No. 2170848-99-2; 'Borate(2), [3-[(1S2R)-cyclopropyl-κc2]-6-fluoro-2-(hydroxy-κO)benzoato(3-)]dihydroxy-, sodium (1:2), (t-4)'; Jan. 24, 2018; ? Page .-carboxylic acid, 5-fluoro-1,1a,2,7b-tetrahydro-2-hydroxy-, (1aR,7bS)'; Jan. 23, 2018; 1 Page.

Hong et al., "Ceftolozane/tazobactam: A Novel Antipseudomonal Cephalosporin and B-lactamase-inhibitor Combination", Infect Drug Resist. (2013) 6: 215-223.

Lin et al., "Pharmacokinetics and dose proportionality of ceftibuten in men", Antimicro Agents Chemother. (1995) 39(2): 359-361.

Monogue et al., "Efficacy of Humanized Exposures of Cefiderocol (S-649266) against a DiversePopulation of Gram-negative Bacteria in a Murine Thigh Infection Model", Antimicrob Agents Chemother. (2017) 61(11): e01022-17 in 10 pages.

Roy et al., "Polymorph discrimination using low wavenumber Raman spectroscopy". Org Process Res Dev. Jul. 19, 2013;17(7):976-980.

Singhal et al., "Drug polymorphism and dosage form design: A practical perspective", Adv Drug Deliv Rev. Feb. 23, 2004;56(3): 335-347.

Cahill et al., Cyclic Boronates Inhibit All Classes of ↑-Lactamases. Antimicro Age Chemother. Apr. 2017;61(4): e02260-16.

CAS Registry No. 1964:447952 CAPLUS; "Arylboronic acids. VII. Some reactions of o-formylbenzenebornic acid", Tschampel et al. (1964); 1 page.

\* cited by examiner

BORONIC ACID DERIVATIVES AND THERAPEUTIC USES THEREOF

CROSS REFERENCE TO RELATED APPLICATIONS

This application claims the benefit of U.S. Provisional Application No. 62/660,729 filed Apr. 20, 2018 entitled "BORONIC ACID DERIVATIVES AND THERAPEUTIC USES THEREOF", which is incorporated by reference in its entirety.

BACKGROUND

Field of the Invention

The present invention relates to the fields of chemistry and medicine. More particularly, the present invention relates to boronic acid antimicrobial compounds, compositions, their preparation, and their use as therapeutic agents.

Description of the Related Art

Antibiotics have been effective tools in the treatment of infectious diseases during the last half-century. From the development of antibiotic therapy to the late 1980s there was almost complete control over bacterial infections in developed countries. However, in response to the pressure of antibiotic usage, multiple resistance mechanisms have become widespread and are threatening the clinical utility of anti-bacterial therapy. The increase in antibiotic resistant strains has been particularly common in major hospitals and care centers. The consequences of the increase in resistant strains include higher morbidity and mortality, longer patient hospitalization, and an increase in treatment costs.

Various bacteria have evolved β-lactam deactivating enzymes, namely, β-lactamases, that counter the efficacy of the various β-lactam antibiotics. β-lactamases can be grouped into 4 classes based on their amino acid sequences, namely, Ambler classes A, B, C, and D. Enzymes in classes A, C, and D include active-site serine β-lactamases, and class B enzymes, which are encountered less frequently, are Zn-dependent. These enzymes catalyze the chemical degradation of β-lactam antibiotics, rendering them inactive. Some β-lactamases can be transferred within and between various bacterial strains and species. The rapid spread of bacterial resistance and the evolution of multi-resistant strains severely limits β-lactam treatment options available.

The increase of class D β-lactamase-expressing bacterium strains such as *Acinetobacter baumannii* has become an emerging multidrug-resistant threat. *A. baumannii* strains express A, C, and D class β-lactamases. The class D β-lactamases such as the OXA families are particularly effective at destroying carbapenem type β-lactam antibiotics, e.g., imipenem, the active carbapenems component of Merck's Primaxin® (Montefour, K.; et al. Crit. Care Nurse 2008, 28, 15; Perez, F. et al. Expert Rev. Anti Infect. Ther. 2008, 6, 269; Bou, G.; Martinez-Beltran, J. Antimicrob. Agents Chemother. 2000, 40, 428. 2006, 50, 2280; Bou, G. et al, J. Antimicrob. Agents Chemother. 2000, 44, 1556). This has imposed a pressing threat to the effective use of drugs in that category to treat and prevent bacterial infections. Indeed the number of catalogued serine-based β-lactamases has exploded from less than ten in the 1970s to over 300 variants. These issues fostered the development of five "generations" of cephalosporins. When initially released into clinical practice, extended-spectrum cephalosporins resisted hydrolysis by the prevalent class A β-lactamases, TEM-1 and SHV-1. However, the development of resistant strains by the evolution of single amino acid substitutions in TEM-1 and SHV-1 resulted in the emergence of the extended-spectrum β-lactamase (ESBL) phenotype.

New β-lactamases have recently evolved that hydrolyze the carbapenem class of antimicrobials, including imipenem, biapenem, doripenem, meropenem, and ertapenem, as well as other β-lactam antibiotics. These carbapenemases belong to molecular classes A, B, and D. Class A carbapenemases of the KPC-type predominantly in *Klebsiella pneumoniae* but now also reported in other Enterobacteriaceae, *Pseudomonas aeruginosa* and *Acinetobacter baumannii*. The KPC carbapenemase was first described in 1996 in North Carolina, but since then has disseminated widely in the US. It has been particularly problematic in the New York City area, where several reports of spread within major hospitals and patient morbidity have been reported. These enzymes have also been recently reported in France, Greece, Sweden, United Kingdom, and an outbreak in Germany has recently been reported. Treatment of resistant strains with carbapenems can be associated with poor outcomes.

The zinc-dependent class B metallo-β-lactamases are represented mainly by the VIM, IMP, and NDM types. IMP and VIM-producing *K. pneumonia* were first observed in 1990s in Japan and 2001 in Southern Europe, respectively. IMP-positive strains remain frequent in Japan and have also caused hospital outbreaks in China and Australia. However, dissemination of IMP-producing Enterobacteriaceae in the rest of the word appears to be somewhat limited. VIM-producing enterobacteria can be frequently isolated in Mediterranean countries, reaching epidemic proportions in Greece. Isolation of VIM-producing strains remains low in Northern Europe and in the United States. In stark contrast, a characteristic of NDM-producing *K. pneumonia* isolates has been their rapid dissemination from their epicenter, the Indian subcontinent, to Western Europe, North America, Australia and Far East. Moreover, NDM genes have spread rapidly to various species other than *K. pneumonia*.

The plasmid-expressed class D carbapenemases belong to OXA-48 type. OXA-48 producing *K. pneumonia* was first detected in Turkey, in 2001. The Middle East and North Africa remain the main centers of infection. However, recent isolation of OXA-48-type producing organisms in India, Senegal and Argentina suggest the possibility of a global expansion. Isolation of OXA-48 in bacteria other than *K. pneumonia* underlines the spreading potential of OXA-48.

Treatment of strains producing any of these carbapenemases with carbapenems can be associated with poor outcomes.

Another mechanism of β-lactamase mediated resistance to carbapenems involves permeability or efflux mechanisms combined with hyper production of β-lactamases. One example is the loss of a porin combined with hyperproduction of ampC β-lactamase resulting in resistance to imipenem in *Pseudomonas aeruginosa*. Efflux pump overexpression combined with hyperproduction of the ampC β-lactamase can also result in resistance to a carbapenem such as meropenem.

Thus, there is a need for improved β-lactamase inhibitors.

SUMMARY OF THE INVENTION

Some embodiments disclosed herein relate to a compound having the structure of the Formula (I) or Formula (II):

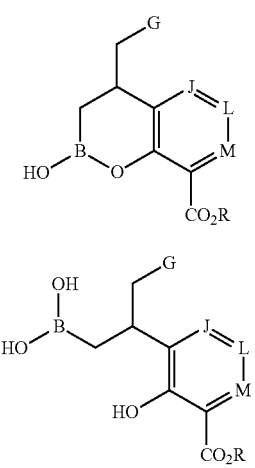

(I)

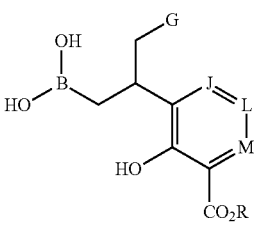

(II)

or a pharmaceutically acceptable salt thereof, wherein:

G is selected from the group consisting of —$OR^1$—C(O) $R^1$, —$C(O)(CH_2)_{0-3}SR^1$, —$C(O)(CH_2)_{1-3}R^1$, —$C(O)OR^1$, —$C(O)NR^1R^2$, —$C(O)NR^1OR^2$, —$N_3$, —$NR^1R^2$, —$NR^1C(O)R^2$, —$NR^1C(O)NR^2R^3$, —$NR^1C(O)OR^2$, —$NR^1S(O)_2R^2$, —$NR^1S(O)_2NR^2R^3$, —$C(=NR^1)R^2$, —$C(=NR^1)NR^2R^3$, —$NR^1CR^2(=NR^3)$, —$NR^1C(=NR^2)NR^3R^4$, —$S(O)_2R^1$, optionally substituted $C_{1-10}$ alkyl, optionally substituted $C_{2-10}$ alkenyl, optionally substituted $C_{2-10}$ alkynyl, optionally substituted $C_{3-7}$ carbocyclyl, optionally substituted 5-10 membered heterocyclyl, optionally substituted $C_{6-10}$ aryl, optionally substituted 5-10 membered heteroaryl, optionally substituted $C_{3-7}$ carbocyclyl-$C_{1-6}$ alkyl, optionally substituted 5-10 membered heterocyclyl-$C_{1-6}$ alkyl, optionally substituted $C_{6-10}$ aryl-$C_{1-6}$ alkyl, and optionally substituted 5-10 membered heteroaryl-$C_{1-6}$ alkyl;

$R^1$, $R^2$, $R^3$, and $R^4$ are each independently selected from the group consisting of —H, optionally substituted $C_{1-4}$ alkyl, optionally substituted $C_{3-7}$ carbocyclyl, optionally substituted 4-10 membered heterocyclyl, optionally substituted $C_{6-10}$ aryl, optionally substituted $C_{6-10}$ aryl-$C_{1-6}$ alkyl, and optionally substituted 5-10 membered heteroaryl;

J is selected from the group consisting of $CR^5$ and N;

L is selected from the group consisting of $CR^6$ and N;

M is selected from the group consisting of $CR^7$ and N;

$R^5$, $R^6$, and $R^7$ are each independently selected from the group consisting of —H, —$OR^8$, halogen, —$CF_3$, optionally substituted $C_2$-$C_6$ alkenyl, optionally substituted $C_2$-$C_6$ alkynyl, optionally substituted $C_1$-$C_6$ heteroalkyl, optionally substituted $C_3$-$C_7$ carbocyclyl, optionally substituted 5-10 membered heterocyclyl, optionally substituted $C_{6-10}$ aryl, optionally substituted 5-10 membered heteroaryl, cyano, $C_1$-$C_6$ alkoxy($C_1$-$C_6$)alkyl, aryloxy, and sulfhydryl (mercapto);

$R^8$ is selected from the group consisting of hydrogen, optionally substituted $C_{1-4}$ alkyl, optionally substituted $C_{3-7}$ carbocyclyl, optionally substituted 4-10 membered heterocyclyl, optionally substituted $C_{6-10}$ aryl, and optionally substituted 5-10 membered heteroaryl;

R is selected from the group consisting of —H, —$C_{1-9}$ alkyl, —$CR^9R^{10}OC(O)C_{1-9}$alkyl, —$CR^9R^{10}OC(O)OC_{1-9}$ alkyl, —$CR^9R^{10}OC(O)C_{6-10}$ aryl, —$CR^9R^{10}OC(O)OC_{6-10}$ aryl,

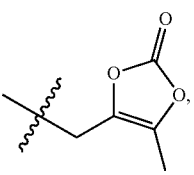 [SMILES: *Cc1oc(=O)oc1C]

—$CR^9R^{10}OC(O)C_{3-7}$ carbocyclyl, —$CR^9R^{10}OC(O)OC_{3-7}$ carbocyclyl, —$CR^9R^{10}OC(O)$(5-10 membered heterocyclyl), and —$CR^9R^{10}OC(O)O$ (5-10 membered heterocyclyl); and $R^9$ and $R^{10}$ are independently selected from the group consisting of —H, optionally substituted $C_{1-4}$ alkyl, optionally substituted $C_{3-7}$ carbocyclyl, optionally substituted 5-10 membered heterocyclyl, optionally substituted $C_{6-10}$ aryl, and optionally substituted 5-10 membered heteroaryl.

Other embodiments disclosed herein include a pharmaceutical composition comprising a therapeutically effective amount of a compound disclosed herein and a pharmaceutically acceptable excipient.

Other embodiments disclosed herein include a method of treating or preventing a bacterial infection, comprising administering to a subject in need thereof a compound disclosed herein.

DETAILED DESCRIPTION

In some embodiments, compounds that contain a boronic acid moiety are provided that act as antimicrobial agents and/or as potentiators of antimicrobial agents. Various embodiments of these compounds include compounds having the structures of Formula (I) as described above or pharmaceutically acceptable salts thereof.

Some embodiments of compounds of Formulas (I) and (II) or their pharmaceutically acceptable salts have the following stereochemistry as shown in the structure of Formula (Ia) or Formula (IIa):

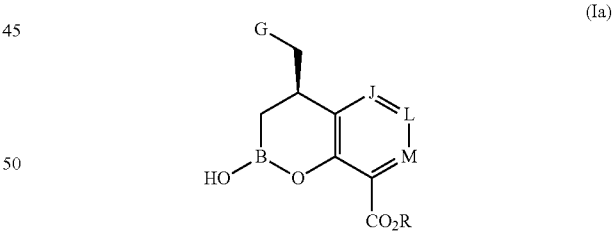

(Ia)

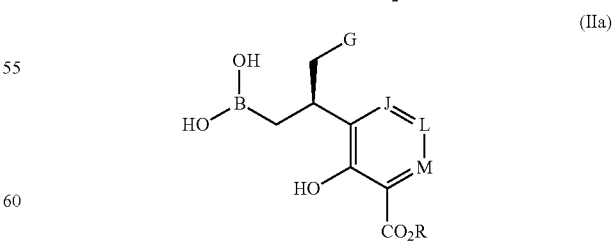

(IIa)

Some embodiments of compounds of Formulas (I) and (II) or their pharmaceutically acceptable salts have the following stereochemistry as shown in the structure of Formula (Ib) or Formula (IIb):

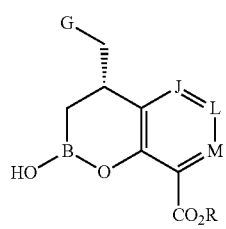
(Ib)

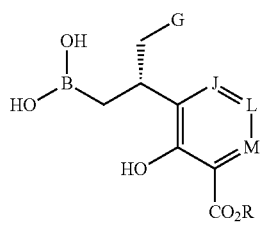
(IIb)

Some embodiments of compounds of Formulas (I) and (II) or their pharmaceutically acceptable salts include compounds having the structure of Formula (Ic) or Formula (IIc):

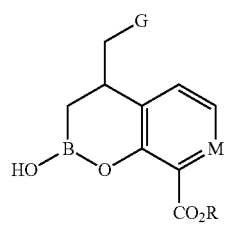
(Ic)

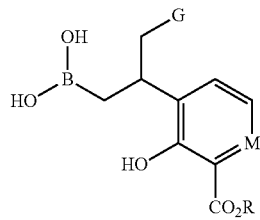
(IIc)

In some embodiments of compounds of Formula (I), (Ia), (Ib), (Ic), (II), (IIa), (IIb), or (IIc) G is selected from the group consisting of —OR$^1$, N$_3$, —NR$^1$R$^2$, NR$^1$C(O)R$^2$, optionally substituted C$_{1-4}$ alkyl, and optionally substituted 5-10 membered heteroaryl;

In some embodiments of compounds of Formula (I), (Ia), (Ib), (Ic), (II), (IIa), (IIb), or (IIc) G is —OR$^1$.

In some embodiments of compounds of Formula (I), (Ia), (Ib), (Ic), (II), (IIa), (IIb), or (IIc) G is selected from the group consisting of —OH, —OMe, —OBn, —CH$_2$OH, N$_3$, NH$_2$, —NHC(=O)H, —NHC(=O)CH$_3$, and

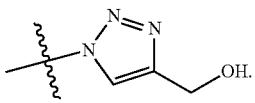 [SMILES: *n1cc(CO)nn1]

In some embodiments of compounds of Formula (I), (Ia), (Ib), (Ic), (II), (IIa), (IIb), or (IIc) G is selected from the group consisting of —OH and —OBn.

In some embodiments of compounds of Formula (I), (Ia), (Ib), (Ic), (II), (IIa), (IIb), or (IIc) G is —OH.

In some embodiments of compounds of Formula (I), (Ia), (Ib), (Ic), (II), (IIa), (IIb), or (IIc) M is CR$^7$ and R$^7$ is selected from the group consisting of —H, —OR$^8$, and halogen.

In some embodiments of compounds of Formula (I), (Ia), (Ib), (Ic), (II), (IIa), (IIb), or (IIc) R$^8$ is optionally substituted C$_{1-4}$ alkyl.

In some embodiments of compounds of Formula (I), (Ia), (Ib), (Ic), (II), (IIa), (IIb), or (IIc) M is selected from the group consisting of —CH, —COMe, CF, and N.

In some embodiments of compounds of Formula (I), (Ia), (Ib), (Ic), (II), (IIa), (IIb), or (IIc) M is —COMe.

In some embodiments of compounds of Formula (I), (Ia), (Ib), (Ic), (II), (IIa), (IIb), or (IIc) R is —H.

Some embodiments include a compound selected from the group consisting of:

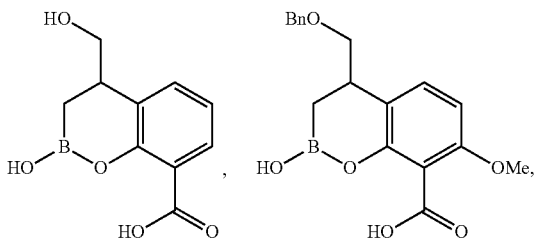

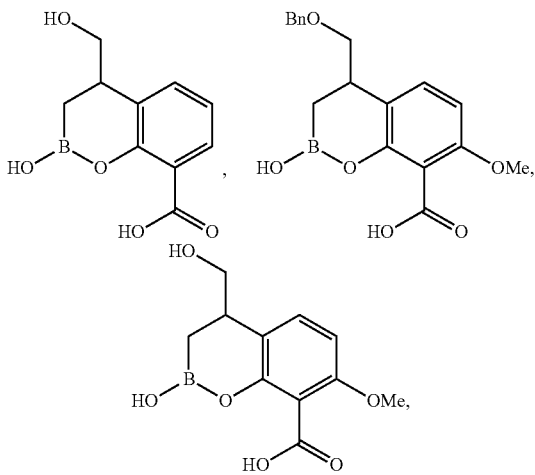

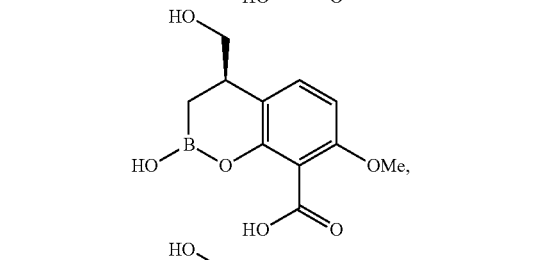

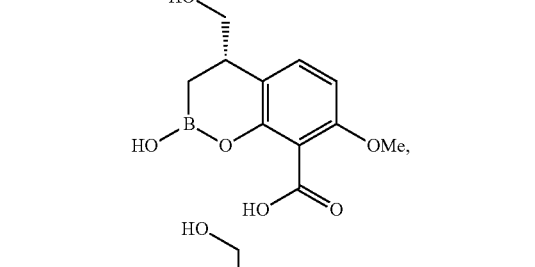
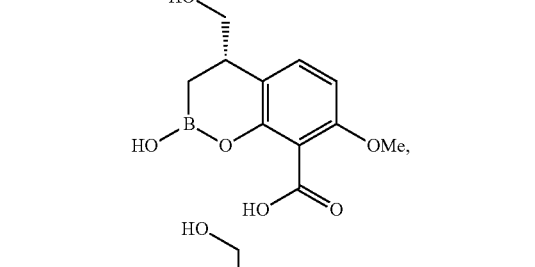

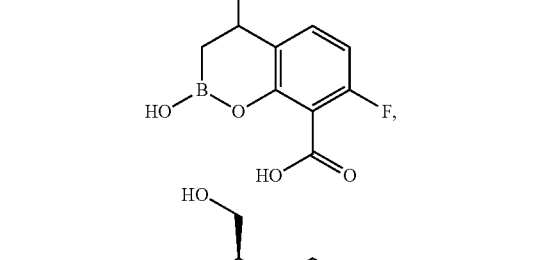
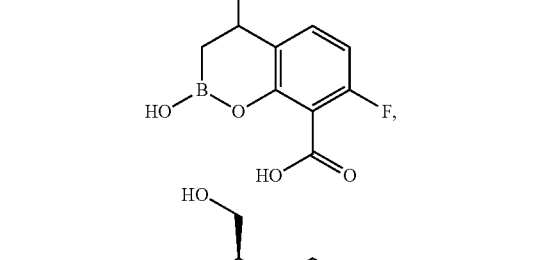

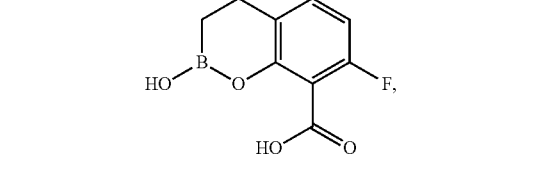
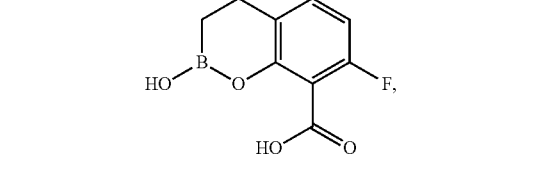

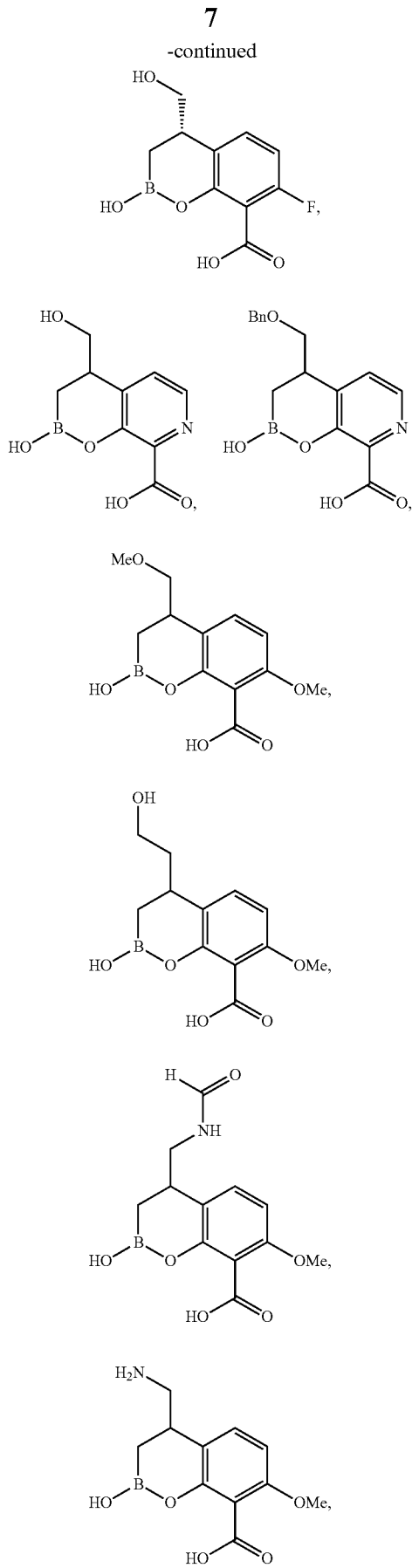

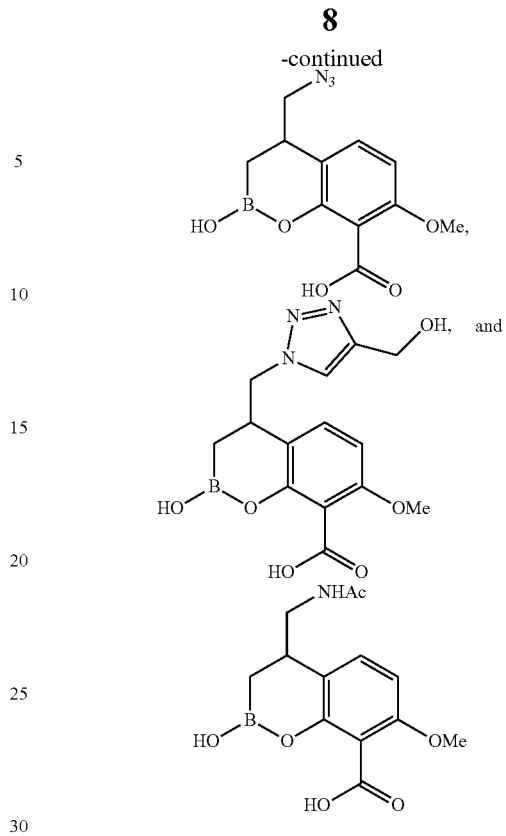

or a pharmaceutically acceptable salt thereof.

Where the compounds disclosed herein have at least one chiral center, they may exist as individual enantiomers and diastereomers or as mixtures of such isomers, including racemates. Separation of the individual isomers or selective synthesis of the individual isomers is accomplished by application of various methods which are well known to practitioners in the art. Unless otherwise indicated, all such isomers and mixtures thereof are included in the scope of the compounds disclosed herein. Furthermore, compounds disclosed herein may exist in one or more crystalline or amorphous forms. Unless otherwise indicated, all such forms are included in the scope of the compounds disclosed herein including any polymorphic forms. In addition, some of the compounds disclosed herein may form solvates with water (i.e., hydrates) or common organic solvents. Unless otherwise indicated, such solvates are included in the scope of the compounds disclosed herein.

The skilled artisan will recognize that some structures described herein may be resonance forms or tautomers of compounds that may be fairly represented by other chemical structures, even when kinetically; the artisan recognizes that such structures may only represent a very small portion of a sample of such compound(s). Such compounds are considered within the scope of the structures depicted, though such resonance forms or tautomers are not represented herein.

In some embodiments, due to the facile exchange of boron esters, the compounds described herein may convert to or exist in equilibrium with alternate forms. Accordingly, in some embodiments, the compounds described herein may exist in combination with one or more of these forms. For example, as shown below, the compounds disclosed herein may exist in cyclic boronate monoesters as formula I or in acyclic form as boronic acids as formula II, or may exist as a mixture of the two forms depending on the medium. When G is —OH or $NHR_2$, compounds of formula II may also cyclize to give compounds of formula III where G" is O or $NR_2$. In this case, the compounds may exist as a mixture of all three forms depending on the medium.

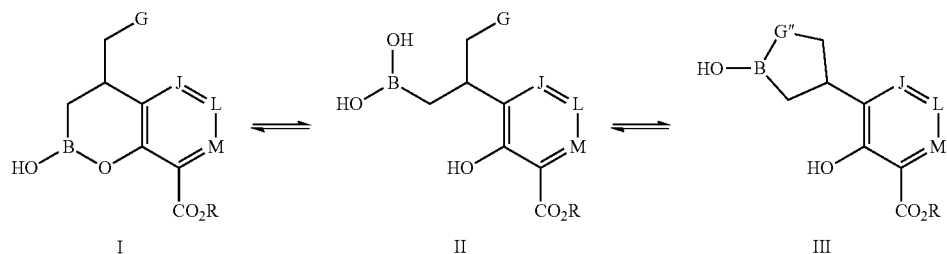

In some embodiments, the compounds described herein may exist in cyclic dimeric form as Formula (A) or trimeric form as Formula (B), tetrameric form as Formula (C) as shown below, or acylic dimeric, trimeric or tetrameric forms and the like.

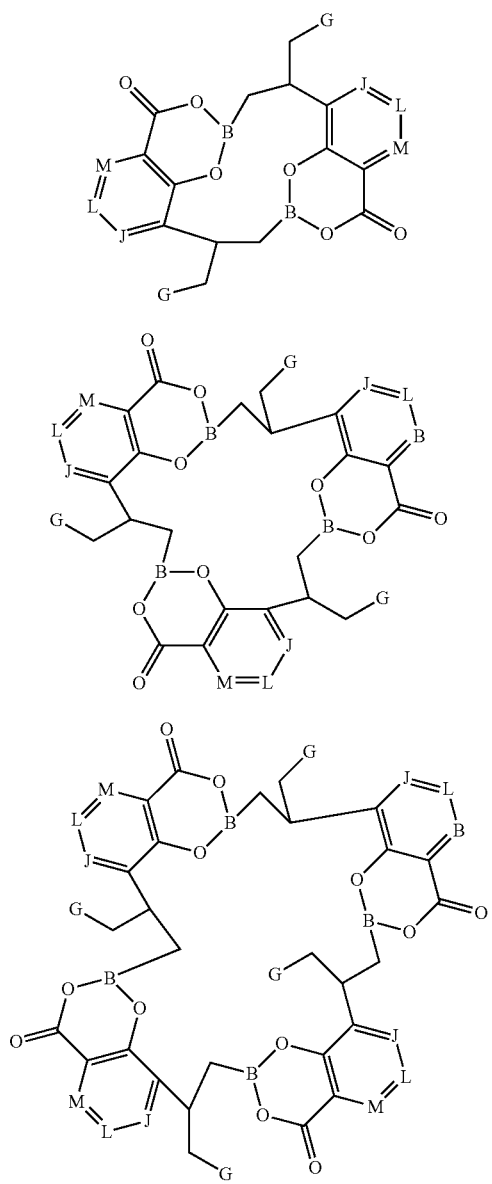

Isotopes may be present in the compounds described. Each chemical element as represented in a compound structure may include any isotope of said element. For example, in a compound structure a hydrogen atom may be explicitly disclosed or understood to be present in the compound. At any position of the compound that a hydrogen atom may be present, the hydrogen atom can be any isotope of hydrogen, including but not limited to hydrogen-1 (protium) and hydrogen-2 (deuterium). Thus, reference herein to a compound encompasses all potential isotopic forms unless the context clearly dictates otherwise.

Definitions

Unless defined otherwise, all technical and scientific terms used herein have the same meaning as is commonly understood by one of ordinary skill in the art to which this disclosure belongs. All patents, applications, published applications, and other publications referred to herein are incorporated by reference in their entirety. In the event that there is a plurality of definitions for a term herein, those in this section prevail unless stated otherwise.

A "prodrug" refers to an agent that is converted into the parent drug in vivo. Prodrugs are often useful because, in some situations, they may be easier to administer than the parent drug. They may, for instance, be bioavailable by oral administration whereas the parent is not. The prodrug may also have improved solubility in pharmaceutical compositions over the parent drug. An example, without limitation, of a prodrug would be a compound which is administered as an ester (the "prodrug") to facilitate transmittal across a cell membrane where water solubility is detrimental to mobility but which then is metabolically hydrolyzed to the carboxylic acid, the active entity, once inside the cell where water-solubility is beneficial. A further example of a prodrug might be a short peptide (polyaminoacid) bonded to an acid group where the peptide is metabolized to reveal the active moiety. Conventional procedures for the selection and preparation of suitable prodrug derivatives are described, for example, in Design of Prodrugs, (ed. H. Bundgaard, Elsevier, 1985), which is hereby incorporated herein by reference in its entirety.

The term "pro-drug ester" refers to derivatives of the compounds disclosed herein formed by the addition of any of several ester-forming groups that are hydrolyzed under physiological conditions. Examples of pro-drug ester groups include pivoyloxymethyl, acetoxymethyl, phthalidyl, indanyl and methoxymethyl, as well as other such groups known in the art, including a (5-R-2-oxo-1,3-dioxolen-4-yl)methyl group. Other examples of pro-drug ester groups can be found in, for example, T. Higuchi and V. Stella, in "Prodrugs as Novel Delivery Systems", Vol. 14, A.C.S. Symposium Series, American Chemical Society (1975); and "Bioreversible Carriers in Drug Design: Theory and Application", edited by E. B. Roche, Pergamon Press: New York, 14-21 (1987) (providing examples of esters useful as prodrugs for compounds containing carboxyl groups). Each of the above-mentioned references is herein incorporated by reference in their entirety.

"Metabolites" of the compounds disclosed herein include active species that are produced upon introduction of the compounds into the biological milieu.

"Solvate" refers to the compound formed by the interaction of a solvent and a compound described herein, a metabolite, or salt thereof. Suitable solvates are pharmaceutically acceptable solvates including hydrates.

The term "pharmaceutically acceptable salt" refers to salts that retain the biological effectiveness and properties of a compound, which are not biologically or otherwise undesirable for use in a pharmaceutical. In many cases, the compounds herein are capable of forming acid and/or base salts by virtue of the presence of amino and/or carboxyl groups or groups similar thereto. Pharmaceutically acceptable acid addition salts can be formed with inorganic acids and organic acids. Inorganic acids from which salts can be derived include, for example, hydrochloric acid, hydrobromic acid, sulfuric acid, nitric acid, phosphoric acid, and the like. Organic acids from which salts can be derived include, for example, acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Pharmaceutically acceptable base addition salts can be formed with inorganic and organic bases. Inorganic bases from which salts can be derived include, for example, sodium, potassium, lithium, ammonium, calcium, magnesium, iron, zinc, copper, manganese, aluminum, and the like; particularly preferred are the ammonium, potassium, sodium, calcium and magnesium salts. Organic bases from which salts can be derived include, for example, primary, secondary, and tertiary amines, substituted amines including naturally occurring substituted amines, cyclic amines, basic ion exchange resins, and the like, specifically such as isopropylamine, trimethylamine, diethylamine, triethylamine, tripropylamine, and ethanolamine. Many such salts are known in the art, as described in WO 87/05297, Johnston et al., published Sep. 11, 1987 (incorporated by reference herein in its entirety). Some examples of pharmaceutically acceptable base addition salts of the compounds disclosed herein have the structure of Formula (I-salt) or (II-salt):

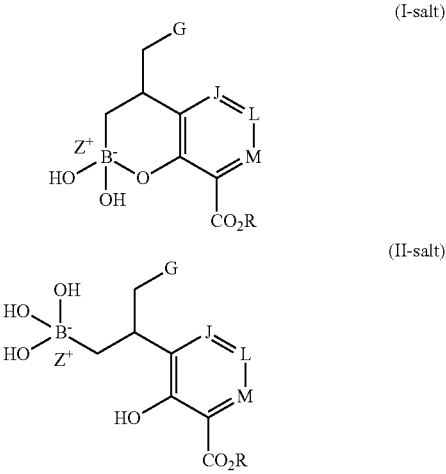

(I-salt)

(II-salt)

wherein Z can be an alkali metal or $NH_4^+$.

As used herein, "$C_a$ to $C_b$" or "$C_{a-b}$" in which "a" and "b" are integers refer to the number of carbon atoms in the specified group. That is, the group can contain from "a" to "b", inclusive, carbon atoms. Thus, for example, a "$C_1$ to $C_4$ alkyl" or "$C_{1-4}$ alkyl" group refers to all alkyl groups having from 1 to 4 carbons, that is, $CH_3$—, $CH_3CH_2$—, $CH_3CH_2CH_2$—, $(CH_3)_2CH$—, $CH_3CH_2CH_2CH_2$—, $CH_3CH_2CH(CH_3)$— and $(CH_3)_3C$—.

The term "halogen" or "halo," as used herein, means any one of the radio-stable atoms of column 7 of the Periodic Table of the Elements, e.g., fluorine, chlorine, bromine, or iodine, with fluorine and chlorine being preferred.

As used herein, "alkyl" refers to a straight or branched hydrocarbon chain that is fully saturated (i.e., contains no double or triple bonds). The alkyl group may have 1 to 20 carbon atoms (whenever it appears herein, a numerical range such as "1 to 20" refers to each integer in the given range; e.g., "1 to 20 carbon atoms" means that the alkyl group may consist of 1 carbon atom, 2 carbon atoms, 3 carbon atoms, etc., up to and including 20 carbon atoms, although the present definition also covers the occurrence of the term "alkyl" where no numerical range is designated). The alkyl group may also be a medium size alkyl having 1 to 9 carbon atoms. The alkyl group could also be a lower alkyl having 1 to 4 carbon atoms. The alkyl group of the compounds may be designated as "$C_{1-4}$ alkyl" or similar designations. By way of example only, "$C_{1-4}$ alkyl" indicates that there are one to four carbon atoms in the alkyl chain, i.e., the alkyl chain is selected from the group consisting of methyl, ethyl, propyl, iso-propyl, n-butyl, iso-butyl, sec-butyl, and t-butyl. Typical alkyl groups include, but are in no way limited to, methyl, ethyl, propyl, isopropyl, butyl, isobutyl, tertiary butyl, pentyl, hexyl, and the like.

As used herein, "alkoxy" refers to the formula —OR wherein R is an alkyl as is defined above, such as "$C_{1-9}$ alkoxy", including but not limited to methoxy, ethoxy, n-propoxy, 1-methylethoxy (isopropoxy), n-butoxy, iso-butoxy, sec-butoxy, tert-butoxy, and the like.

As used herein, "alkylthio" refers to the formula —SR wherein R is an alkyl as is defined above, such as "$C_{1-9}$ alkylthio" and the like, including but not limited to methylmercapto, ethylmercapto, n-propylmercapto, 1-methylethylmercapto (isopropylmercapto), n-butylmercapto, iso-butylmercapto, sec-butylmercapto, tert-butylmercapto, and the like.

As used herein, "alkenyl" refers to a straight or branched hydrocarbon chain containing one or more double bonds. The alkenyl group may have 2 to 20 carbon atoms, although the present definition also covers the occurrence of the term "alkenyl" where no numerical range is designated. The alkenyl group may also be a medium size alkenyl having 2 to 9 carbon atoms. The alkenyl group could also be a lower alkenyl having 2 to 4 carbon atoms. The alkenyl group of the compounds may be designated as "$C_{2-4}$ alkenyl" or similar designations. By way of example only, "$C_{2-4}$ alkenyl" indicates that there are two to four carbon atoms in the alkenyl chain, i.e., the alkenyl chain is selected from the group consisting of ethenyl, propen-1-yl, propen-2-yl, propen-3-yl, buten-1-yl, buten-2-yl, buten-3-yl, buten-4-yl, 1-methyl-propen-1-yl, 2-methyl-propen-1-yl, 1-ethyl-ethen-1-yl, 2-methyl-propen-3-yl, buta-1,3-dienyl, buta-1,2,-dienyl, and buta-1,2-dien-4-yl. Typical alkenyl groups include, but are in no way limited to, ethenyl, propenyl, butenyl, pentenyl, hexenyl, and the like.

As used herein, "alkynyl" refers to a straight or branched hydrocarbon chain containing one or more triple bonds. The alkynyl group may have 2 to 20 carbon atoms, although the present definition also covers the occurrence of the term "alkynyl" where no numerical range is designated. The alkynyl group may also be a medium size alkynyl having 2 to 9 carbon atoms. The alkynyl group could also be a lower alkynyl having 2 to 4 carbon atoms. The alkynyl group of the compounds may be designated as "$C_{2-4}$ alkynyl" or similar designations. By way of example only, "$C_{2-4}$ alkynyl" indicates that there are two to four carbon atoms in the alkynyl chain, i.e., the alkynyl chain is selected from the group consisting of ethynyl, propyn-1-yl, propyn-2-yl, butyn-1-yl, butyn-3-yl, butyn-4-yl, and 2-butynyl. Typical alkynyl groups include, but are in no way limited to, ethynyl, propynyl, butynyl, pentynyl, hexynyl, and the like.

As used herein, "heteroalkyl" refers to a straight or branched hydrocarbon chain containing one or more heteroatoms, that is, an element other than carbon, including but not limited to, nitrogen, oxygen and sulfur, in the chain backbone. The heteroalkyl group may have 1 to 20 carbon atoms although the present definition also covers the occurrence of the term "heteroalkyl" where no numerical range is designated. The heteroalkyl group may also be a medium size heteroalkyl having 1 to 9 carbon atoms. The heteroalkyl group could also be a lower heteroalkyl having 1 to 4 carbon atoms. The heteroalkyl group of the compounds may be designated as "$C_{1-4}$ heteroalkyl" or similar designations. The heteroalkyl group may contain one or more heteroatoms. By way of example only, "$C_{1-4}$ heteroalkyl" indicates that there are one to four carbon atoms in the heteroalkyl chain and additionally one or more heteroatoms in the backbone of the chain.

The term "aromatic" refers to a ring or ring system having a conjugated pi electron system and includes both carbocyclic aromatic (e.g., phenyl) and heterocyclic aromatic groups (e.g., pyridine). The term includes monocyclic or fused-ring polycyclic (i.e., rings which share adjacent pairs of atoms) groups provided that the entire ring system is aromatic.

As used herein, "aryl" refers to an aromatic ring or ring system (i.e., two or more fused rings that share two adjacent carbon atoms) containing only carbon in the ring backbone. When the aryl is a ring system, every ring in the system is aromatic. The aryl group may have 6 to 18 carbon atoms, although the present definition also covers the occurrence of the term "aryl" where no numerical range is designated. In some embodiments, the aryl group has 6 to 10 carbon atoms. The aryl group may be designated as "$C_{6-10}$ aryl," "$C_6$ or $C_{10}$ aryl," or similar designations. Examples of aryl groups include, but are not limited to, phenyl, naphthyl, azulenyl, and anthracenyl.

As used herein, "aryloxy" and "arylthio" refers to RO— and RS—, in which R is an aryl as is defined above, such as "$C_{6-10}$ aryloxy" or "$C_{6-10}$ arylthio" and the like, including but not limited to phenyloxy.

An "aralkyl" or "arylalkyl" is an aryl group connected, as a substituent, via an alkylene group, such "$C_{7-14}$ aralkyl" and the like, including but not limited to benzyl, 2-phenylethyl, 3-phenylpropyl, and naphthylalkyl. In some cases, the alkylene group is a lower alkylene group (i.e., a $C_{1-4}$ alkylene group).

As used herein, "heteroaryl" refers to an aromatic ring or ring system (i.e., two or more fused rings that share two adjacent atoms) that contain(s) one or more heteroatoms, that is, an element other than carbon, including but not limited to, nitrogen, oxygen and sulfur, in the ring backbone. When the heteroaryl is a ring system, every ring in the system is aromatic. The heteroaryl group may have 5-18 ring members (i.e., the number of atoms making up the ring backbone, including carbon atoms and heteroatoms), although the present definition also covers the occurrence of the term "heteroaryl" where no numerical range is designated. In some embodiments, the heteroaryl group has 5 to 10 ring members or 5 to 7 ring members. The heteroaryl group may be designated as "5-7 membered heteroaryl," "5-10 membered heteroaryl," or similar designations. Examples of heteroaryl rings include, but are not limited to, furyl, thienyl, phthalazinyl, pyrrolyl, oxazolyl, thiazolyl, imidazolyl, pyrazolyl, isoxazolyl, isothiazolyl, triazolyl, thiadiazolyl, pyridinyl, pyridazinyl, pyrimidinyl, pyrazinyl, triazinyl, quinolinyl, isoquinlinyl, benzimidazolyl, benzoxazolyl, benzothiazolyl, indolyl, isoindolyl, and benzothienyl.

A "heteroaralkyl" or "heteroarylalkyl" is heteroaryl group connected, as a substituent, via an alkylene group. Examples include but are not limited to 2-thienylmethyl, 3-thienylmethyl, furylmethyl, thienylethyl, pyrrolylalkyl, pyridylalkyl, isoxazollylalkyl, and imidazolylalkyl. In some cases, the alkylene group is a lower alkylene group (i.e., a $C_{1-4}$ alkylene group).

As used herein, "carbocyclyl" means a non-aromatic cyclic ring or ring system containing only carbon atoms in the ring system backbone. When the carbocyclyl is a ring system, two or more rings may be joined together in a fused, bridged or spiro-connected fashion. Carbocyclyls may have any degree of saturation provided that at least one ring in a ring system is not aromatic. Thus, carbocyclyls include cycloalkyls, cycloalkenyls, and cycloalkynyls. The carbocyclyl group may have 3 to 20 carbon atoms, although the present definition also covers the occurrence of the term "carbocyclyl" where no numerical range is designated. The carbocyclyl group may also be a medium size carbocyclyl having 3 to 10 carbon atoms. The carbocyclyl group could also be a carbocyclyl having 3 to 6 carbon atoms. The carbocyclyl group may be designated as "$C_{3-6}$ carbocyclyl" or similar designations. Examples of carbocyclyl rings include, but are not limited to, cyclopropyl, cyclobutyl, cyclopentyl, cyclohexyl, cyclohexenyl, 2,3-dihydro-indene, bicycle[2.2.2]octanyl, adamantyl, and spiro[4.4]nonanyl.

A "(carbocyclyl)alkyl" is a carbocyclyl group connected, as a substituent, via an alkylene group, such as "$C_{4-10}$ (carbocyclyl)alkyl" and the like, including but not limited to, cyclopropylmethyl, cyclobutylmethyl, cyclopropylethyl, cyclopropylbutyl, cyclobutylethyl, cyclopropylisopropyl, cyclopentylmethyl, cyclopentylethyl, cyclohexylmethyl, cyclohexylethyl, cycloheptylmethyl, and the like. In some cases, the alkylene group is a lower alkylene group.

As used herein, "cycloalkyl" means a fully saturated carbocyclyl ring or ring system. Examples include cyclopropyl, cyclobutyl, cyclopentyl, and cyclohexyl.

As used herein, "cycloalkenyl" means a carbocyclyl ring or ring system having at least one double bond, wherein no ring in the ring system is aromatic. An example is cyclohexenyl.

As used herein, "heterocyclyl" means a non-aromatic cyclic ring or ring system containing at least one heteroatom in the ring backbone. Heterocyclyls may be joined together in a fused, bridged or spiro-connected fashion. Heterocyclyls may have any degree of saturation provided that at least one ring in the ring system is not aromatic. The heteroatom(s) may be present in either a non-aromatic or aromatic ring in the ring system. The heterocyclyl group may have 3 to 20 ring members (i.e., the number of atoms making up the ring backbone, including carbon atoms and heteroatoms), although the present definition also covers the occurrence of the term "heterocyclyl" where no numerical range is designated. The heterocyclyl group may also be a medium size heterocyclyl having 3 to 10 ring members. The heterocyclyl group could also be a heterocyclyl having 3 to 6 ring members. The heterocyclyl group may be designated as "3-6 membered heterocyclyl" or similar designations. In preferred six membered monocyclic heterocyclyls, the heteroatom(s) are selected from one up to three of O, N or S, and in preferred five membered monocyclic heterocyclyls, the heteroatom(s) are selected from one or two heteroatoms selected from O, N, or S. Examples of heterocyclyl rings include, but are not limited to, azepinyl, acridinyl, carbazolyl, cinnolinyl, dioxolanyl, imidazolinyl, imidazolidinyl, morpholinyl, oxiranyl, oxepanyl, thiepanyl, piperidinyl, piperazinyl, dioxopiperazinyl, pyrrolidinyl, pyrrolidonyl, pyrrolidionyl, 4-piperidonyl, pyrazolinyl, pyrazolidinyl, 1,3-dioxinyl, 1,3-dioxanyl, 1,4-dioxinyl, 1,4-dioxanyl, 1,3-oxathianyl, 1,4-oxathiinyl, 1,4-oxathianyl, 2H-1,2-oxazinyl, trioxanyl, hexahydro-1,3,5-triazinyl, 1,3-dioxolyl, 1,3-dioxolanyl, 1,3-dithiolyl, 1,3-dithiolanyl, isoxazolinyl, isoxazolidinyl, oxazolinyl, oxazolidinyl, oxazolidinonyl, thiazolinyl, thiazolidinyl, 1,3-oxathiolanyl, indolinyl, isoindolinyl, tetrahydrofuranyl, tetrahydropyranyl, tetrahydrothiophenyl, tetrahydrothiopyranyl, tetrahydro-1,4-thiazinyl, thiamorpholinyl, dihydrobenzofuranyl, benzimidazolidinyl, and tetrahydroquinoline.

A "(heterocyclyl)alkyl" is a heterocyclyl group connected, as a substituent, via an alkylene group. Examples include, but are not limited to, imidazolinylmethyl and indolinylethyl.

As used herein, "acyl" refers to $-C(=O)R$, wherein R is hydrogen, $C_{1-6}$ alkyl, $C_{2-6}$ alkenyl, $C_{2-6}$ alkynyl, $C_{3-7}$ carbocyclyl, aryl, 5-10 membered heteroaryl, and 5-10 membered heterocyclyl, as defined herein. Non-limiting examples include formyl, acetyl, propanoyl, benzoyl, and acryl.

An "O-carboxy" group refers to a "$-OC(=O)R$" group in which R is selected from hydrogen, $C_{1-6}$ alkyl, $C_{2-6}$ alkenyl, $C_{2-6}$ alkynyl, $C_{3-7}$ carbocyclyl, aryl, 5-10 membered heteroaryl, and 5-10 membered heterocyclyl, as defined herein.

A "C-carboxy" group refers to a "$-C(=O)OR$" group in which R is selected from hydrogen, $C_{1-6}$ alkyl, $C_{2-6}$ alkenyl, $C_{2-6}$ alkynyl, $C_{3-7}$ carbocyclyl, aryl, 5-10 membered heteroaryl, and 5-10 membered heterocyclyl, as defined herein. A non-limiting example includes carboxyl (i.e., $-C(=O)OH$).

A "cyano" group refers to a "$-CN$" group.

A "cyanato" group refers to an "$-OCN$" group.

An "isocyanato" group refers to a "$-NCO$" group.

A "thiocyanato" group refers to a "$-SCN$" group.

An "isothiocyanato" group refers to an "$-NCS$" group.

A "sulfinyl" group refers to an "$-S(=O)R$" group in which R is selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein.

A "sulfonyl" group refers to an "$-SO_2R$" group in which R is selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein.

An "S-sulfonamido" group refers to a "$-SO_2NR_AR_B$" group in which $R_A$ and $R_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein.

An "N-sulfonamido" group refers to a "$-N(R_A)SO_2R_B$" group in which $R_A$ and $R_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein.

An "O-carbamyl" group refers to a "$-OC(=O)NR_AR_B$" group in which $R_A$ and $R_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein.

An "N-carbamyl" group refers to an "$-N(R_A)OC(=O)R_B$" group in which $R_A$ and $R_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein.

An "O-thiocarbamyl" group refers to a "$-OC(=S)NR_AR_B$" group in which $R_A$ and $R_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein.

An "N-thiocarbamyl" group refers to an "$-N(R_A)OC(=S)R_B$" group in which $R_A$ and $R_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein.

A "C-amido" group refers to a "$-C(=O)NR_AR_B$" group in which $R_A$ and $R_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein.

An "N-amido" group refers to a "$-N(R_A)C(=O)R_B$" group in which $R_A$ and $R_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein.

An "amino" group refers to a "$-NR_AR_B$" group in which $R_A$ and $R_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein.

An "aminoalkyl" group refers to an amino group connected via an alkylene group.

An "alkoxyalkyl" group refers to an alkoxy group connected via an alkylene group, such as a "$C_{2-8}$ alkoxyalkyl" and the like.

As used herein, a substituted group is derived from the unsubstituted parent group in which there has been an exchange of one or more hydrogen atoms for another atom or group. Unless otherwise indicated, when a group is deemed to be "substituted," it is meant that the group is substituted with one or more substituents independently selected from $C_1$-$C_6$ alkyl, $C_1$-$C_6$ alkenyl, $C_1$-$C_6$ alkynyl, $C_1$-$C_6$ heteroalkyl, $C_3$-$C_7$ carbocyclyl (optionally substituted with halo, $C_1$-$C_6$ alkyl, $C_1$-$C_6$ alkoxy, $C_1$-$C_6$ haloalkyl, and $C_1$-$C_6$ haloalkoxy), $C_3$-$C_7$-carbocyclyl-$C_1$-$C_6$-alkyl (optionally substituted with halo, $C_1$-$C_6$ alkyl, $C_1$-$C_6$ alkoxy, $C_1$-$C_6$ haloalkyl, and $C_1$-$C_6$ haloalkoxy), 5-10 membered heterocyclyl (optionally substituted with halo, $C_1$-$C_6$ alkyl, $C_1$-$C_6$ alkoxy, $C_1$-$C_6$ haloalkyl, and $C_1$-$C_6$ haloalkoxy), 5-10 membered heterocyclyl-$C_1$-$C_6$-alkyl (optionally substituted with halo, $C_1$-$C_6$ alkyl, $C_1$-$C_6$ alkoxy, $C_1$-$C_6$ haloalkyl, and $C_1$-$C_6$ haloalkoxy), aryl (optionally substituted with halo, $C_1$-$C_6$ alkyl, $C_1$-$C_6$ alkoxy, $C_1$-$C_6$ haloalkyl, and $C_1$-$C_6$ haloalkoxy), aryl($C_1$-$C_6$)alkyl (optionally substituted with halo, $C_1$-$C_6$ alkyl, $C_1$-$C_6$ alkoxy, $C_1$-$C_6$ haloalkyl, and $C_1$-$C_6$ haloalkoxy), 5-10 membered heteroaryl (optionally substituted with halo, $C_1$-$C_6$ alkyl, $C_1$-$C_6$ alkoxy, $C_1$-$C_6$ haloalkyl, and $C_1$-$C_6$ haloalkoxy), 5-10 membered heteroaryl($C_1$-$C_6$) alkyl (optionally substituted with halo, $C_1$-$C_6$ alkyl, $C_1$-$C_6$ alkoxy, $C_1$-$C_6$ haloalkyl, and $C_1$-$C_6$ haloalkoxy), halo, cyano, hydroxy, $C_1$-$C_6$ alkoxy, $C_1$-$C_6$ alkoxy($C_1$-$C_6$)alkyl (i.e., ether), aryloxy, sulfhydryl (mercapto), halo($C_1$-$C_6$) alkyl (e.g., —$CF_3$), halo($C_1$-$C_6$)alkoxy (e.g., —$OCF_3$), $C_1$-$C_6$ alkylthio, arylthio, amino, amino($C_1$-$C_6$)alkyl, nitro, O-carbamyl, N-carbamyl, O-thiocarbamyl, N-thiocarbamyl, C-amido, N-amido, S-sulfonamido, N-sulfonamido, C-carboxy, O-carboxy, acyl, cyanato, isocyanato, thiocyanato, isothiocyanato, sulfinyl, sulfonyl, and oxo (=O). Wherever a group is described as "optionally substituted" that group can be substituted with the above substituents.

In some embodiments, substituted group(s) is (are) substituted with one or more substituent(s) individually and independently selected from $C_1$-$C_4$ alkyl, amino, hydroxy, and halogen.

It is to be understood that certain radical naming conventions can include either a mono-radical or a di-radical, depending on the context. For example, where a substituent requires two points of attachment to the rest of the molecule, it is understood that the substituent is a di-radical. For example, a substituent identified as alkyl that requires two points of attachment includes di-radicals such as —$CH_2$—, —$CH_2CH_2$—, —$CH_2CH(CH_3)CH_2$—, and the like. Other radical naming conventions clearly indicate that the radical is a di-radical such as "alkylene" or "alkenylene."

As used herein, "alkylene" means a branched, or straight chain fully saturated di-radical chemical group containing only carbon and hydrogen that is attached to the rest of the molecule via two points of attachment (i.e., an alkanediyl). The alkylene group may have 1 to 20 carbon atoms, although the present definition also covers the occurrence of the term alkylene where no numerical range is designated. The alkylene group may also be a medium size alkylene having 1 to 9 carbon atoms. The alkylene group could also be a lower alkylene having 1 to 4 carbon atoms. The alkylene group may be designated as "$C_{1-4}$ alkylene" or similar designations. By way of example only, "$C_{1-4}$ alkylene" indicates that there are one to four carbon atoms in the alkylene chain, i.e., the alkylene chain is selected from the group consisting of methylene, ethylene, ethan-1,1-diyl, propylene, propan-1,1-diyl, propan-2,2-diyl, 1-methyl-ethylene, butylene, butan-1,1-diyl, butan-2,2-diyl, 2-methyl-propan-1,1-diyl, 1-methyl-propylene, 2-methyl-propylene, 1,1-dimethyl-ethylene, 1,2-dimethyl-ethylene, and 1-ethyl-ethylene.

As used herein, "alkenylene" means a straight or branched chain di-radical chemical group containing only carbon and hydrogen and containing at least one carbon-carbon double bond that is attached to the rest of the molecule via two points of attachment. The alkenylene group may have 2 to 20 carbon atoms, although the present definition also covers the occurrence of the term alkenylene where no numerical range is designated. The alkenylene group may also be a medium size alkenylene having 2 to 9 carbon atoms. The alkenylene group could also be a lower alkenylene having 2 to 4 carbon atoms. The alkenylene group may be designated as "$C_{2-4}$ alkenylene" or similar designations. By way of example only, "$C_{2-4}$ alkenylene" indicates that there are two to four carbon atoms in the alkenylene chain, i.e., the alkenylene chain is selected from the group consisting of ethenylene, ethen-1,1-diyl, propenylene, propen-1,1-diyl, prop-2-en-1,1-diyl, 1-methyl-ethenylene, but-1-enylene, but-2-enylene, but-1,3-dienylene, buten-1,1-diyl, but-1,3-dien-1,1-diyl, but-2-en-1,1-diyl, but-3-en-1,1-diyl, 1-methyl-prop-2-en-1,1-diyl, 2-methyl-prop-2-en-1,1-diyl, 1-ethyl-ethenylene, 1,2-dimethyl-ethenylene, 1-methyl-propenylene, 2-methyl-propenylene, 3-methyl-propenylene, 2-methyl-propen-1,1-diyl, and 2,2-dimethyl-ethen-1,1-diyl.

When two R groups are said to form a ring (e.g., a carbocyclyl, heterocyclyl, aryl, or heteroaryl ring) "together with the atom to which they are attached," it is meant that the collective unit of the atom and the two R groups are the recited ring. The ring is not otherwise limited by the definition of each R group when taken individually. For example, when the following substructure is present:

and $R^1$ and $R^2$ are defined as selected from the group consisting of hydrogen and alkyl, or $R^1$ and $R^2$ together with the nitrogen to which they are attached form a heterocyclyl, it is meant that $R^1$ and $R^2$ can be selected from hydrogen or alkyl, or alternatively, the substructure has structure:

where ring A is a heterocyclyl ring containing the depicted nitrogen.

Similarly, when two "adjacent" R groups are said to form a ring "together with the atoms to which they are attached," it is meant that the collective unit of the atoms, intervening bonds, and the two R groups are the recited ring. For example, when the following substructure is present:

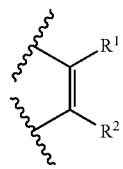

and $R^1$ and $R^2$ are defined as selected from the group consisting of hydrogen and alkyl, or $R^1$ and $R^2$ together with the atoms to which they are attached form an aryl or carbocylyl, it is meant that $R^1$ and $R^2$ can be selected from hydrogen or alkyl, or alternatively, the substructure has structure:

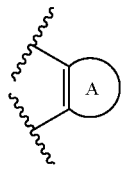

where A is an aryl ring or a carbocylyl containing the depicted double bond.

Wherever a substituent is depicted as a di-radical (i.e., has two points of attachment to the rest of the molecule), it is to be understood that the substituent can be attached in any directional configuration unless otherwise indicated. Thus, for example, a substituent depicted as -AE- or

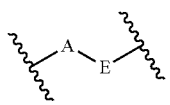

includes the substituent being oriented such that the A is attached at the leftmost attachment point of the molecule as well as the case in which A is attached at the rightmost attachment point of the molecule.

As used herein, "isosteres" of a chemical group are other chemical groups that exhibit the same or similar properties. For example, tetrazole is an isostere of carboxylic acid because it mimics the properties of carboxylic acid even though they both have very different molecular formulae. Tetrazole is one of many possible isosteric replacements for carboxylic acid. Other carboxylic acid isosteres contemplated include —SO$_3$H, —SO$_2$HNR, —PO$_2$(R)$_2$, —PO$_3$(R)$_2$, —CONHNSO$_2$R, —COHNSO$_2$R, and —CONRCN, where R is selected from hydrogen, C$_{1-6}$ alkyl, C$_{2-6}$ alkenyl, C$_{2-6}$ alkynyl, C$_{3-7}$ carbocyclyl, C$_{6-10}$ aryl, 5-10 membered heteroaryl, and 3-10 membered heterocyclyl, as defined herein. In addition, carboxylic acid isosteres can include 5-7 membered carbocycles or heterocycles containing any combination of CH$_2$, O, S, or N in any chemically stable oxidation state, where any of the atoms of said ring structure are optionally substituted in one or more positions. The following structures are non-limiting examples of carbocyclic and heterocyclic isosteres contemplated. The atoms of said ring structure may be optionally substituted at one or more positions with R as defined above.

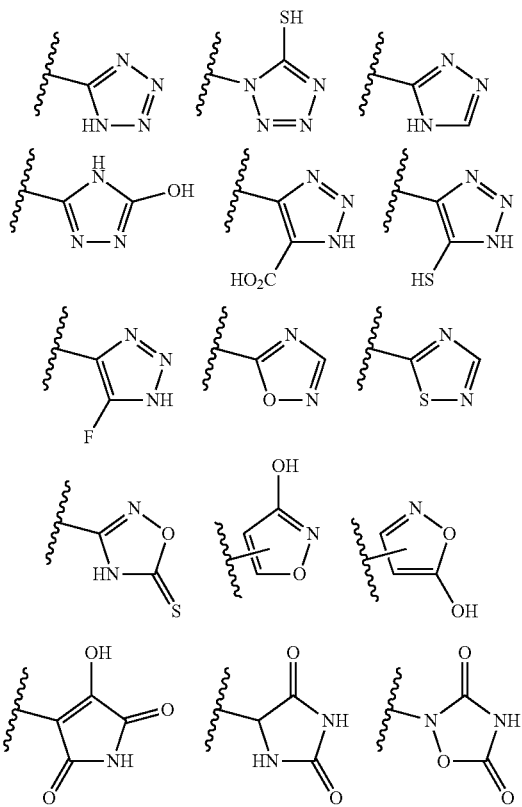

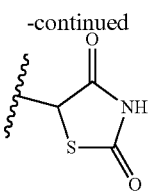

It is also contemplated that when chemical substituents are added to a carboxylic isostere, the compound retains the properties of a carboxylic isostere. It is contemplated that when a carboxylic isostere is optionally substituted with one or more moieties selected from R as defined above, then the substitution and substitution position is selected such that it does not eliminate the carboxylic acid isosteric properties of the compound. Similarly, it is also contemplated that the placement of one or more R substituents upon a carbocyclic or heterocyclic carboxylic acid isostere is not a substitution at one or more atom(s) that maintain(s) or is/are integral to the carboxylic acid isosteric properties of the compound, if such substituent(s) would destroy the carboxylic acid isosteric properties of the compound.

Other carboxylic acid isosteres not specifically exemplified in this specification are also contemplated.

The term "agent" or "test agent" includes any substance, molecule, element, compound, entity, or a combination thereof. It includes, but is not limited to, e.g., protein, polypeptide, peptide or mimetic, small organic molecule, polysaccharide, polynucleotide, and the like. It can be a natural product, a synthetic compound, or a chemical compound, or a combination of two or more substances. Unless otherwise specified, the terms "agent", "substance", and "compound" are used interchangeably herein.

The term "analog" is used herein to refer to a molecule that structurally resembles a reference molecule but which has been modified in a targeted and controlled manner, by replacing a specific substituent of the reference molecule with an alternate substituent. Compared to the reference molecule, an analog would be expected, by one skilled in the art, to exhibit the same, similar, or improved utility. Synthesis and screening of analogs, to identify variants of known compounds having improved characteristics (such as higher binding affinity for a target molecule) is an approach that is well known in pharmaceutical chemistry.

The term "mammal" is used in its usual biological sense. Thus, it specifically includes, but is not limited to, primates, including simians (chimpanzees, apes, monkeys) and humans, cattle, horses, sheep, goats, swine, rabbits, dogs, cats, rats and mice but also includes many other species.

The term "microbial infection" refers to the invasion of the host organism, whether the organism is a vertebrate, invertebrate, fish, plant, bird, or mammal, by pathogenic microbes. This includes the excessive growth of microbes that are normally present in or on the body of a mammal or other organism. More generally, a microbial infection can be any situation in which the presence of a microbial population(s) is damaging to a host mammal. Thus, a mammal is "suffering" from a microbial infection when excessive numbers of a microbial population are present in or on a mammal's body, or when the effects of the presence of a microbial population(s) is damaging the cells or other tissue of a mammal. Specifically, this description applies to a bacterial infection. Note that the compounds of preferred embodiments are also useful in treating microbial growth or contamination of cell cultures or other media, or inanimate surfaces or objects, and nothing herein should limit the preferred embodiments only to treatment of higher organisms, except when explicitly so specified in the claims.

The term "pharmaceutically acceptable carrier" or "pharmaceutically acceptable excipient" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. In addition, various adjuvants such as are commonly used in the art may be included. Considerations for the inclusion of various components in pharmaceutical compositions are described, e.g., in Gilman et al. (Eds.) (1990); Goodman and Gilman's: The Pharmacological Basis of Therapeutics, 8th Ed., Pergamon Press, which is incorporated herein by reference in its entirety.

"Subject" as used herein, means a human or a non-human mammal, e.g., a dog, a cat, a mouse, a rat, a cow, a sheep, a pig, a goat, a non-human primate or a bird, e.g., a chicken, as well as any other vertebrate or invertebrate.

An "effective amount" or a "therapeutically effective amount" as used herein refers to an amount of a therapeutic agent that is effective to relieve, to some extent, or to reduce the likelihood of onset of, one or more of the symptoms of a disease or condition, and includes curing a disease or condition. "Curing" means that the symptoms of a disease or condition are eliminated; however, certain long-term or permanent effects may exist even after a cure is obtained (such as extensive tissue damage).

"Treat," "treatment," or "treating," as used herein refers to administering a pharmaceutical composition for prophylactic and/or therapeutic purposes. The term "prophylactic treatment" refers to treating a subject who does not yet exhibit symptoms of a disease or condition, but who is susceptible to, or otherwise at risk of, a particular disease or condition, whereby the treatment reduces the likelihood that the patient will develop the disease or condition. The term "therapeutic treatment" refers to administering treatment to a subject who exhibits symptoms of a disease or condition.

Methods of Preparation

The compounds disclosed herein may be synthesized by methods described below, or by modification of these methods. Ways of modifying the methodology include, among others, temperature, solvent, reagents etc., known to those skilled in the art. In general, during any of the processes for preparation of the compounds disclosed herein, it may be necessary and/or desirable to protect sensitive or reactive groups on any of the molecules concerned. This may be achieved by means of conventional protecting groups, such as those described in *Protective Groups in Organic Chemistry* (ed. J. F. W. McOmie, Plenum Press, 1973); and P. G. M. Green, T. W. Wutts, *Protecting Groups in Organic Synthesis* (3rd ed.) Wiley, New York (1999), which are both hereby incorporated herein by reference in their entirety. The protecting groups may be removed at a convenient subsequent stage using methods known from the art. Synthetic chemistry transformations useful in synthesizing applicable compounds are known in the art and include e.g. those described in R. Larock, *Comprehensive Organic Transformations*, VCH Publishers, 1989, or L. Paquette, ed., *Encyclopedia of Reagents for Organic Synthesis*, John Wiley and Sons, 1995, which are both hereby incorporated herein by reference in their entirety. The routes shown and described herein are illustrative only and are not intended, nor are they to be construed, to limit the scope of the claims in any manner whatsoever. Those skilled in the art will be able to recognize modifications of the disclosed syntheses and to devise alternate routes based on the disclosures herein; all such modifications and alternate routes are within the scope of the claims.

In the following schemes, protecting groups for oxygen atoms are selected for their compatibility with the requisite synthetic steps as well as compatibility of the introduction and deprotection steps with the overall synthetic schemes (P. G. M. Green, T. W. Wutts, Protecting Groups in Organic Synthesis (3rd ed.) Wiley, New York (1999)). Handling of protecting and/or stereodirecting groups specific to boronic acid derivatives is described in a recent review of chemistry of boronic acids: D. G. Hall (Ed.), Boronic Acids. Preparation and Application in Organic Synthesis and Medicine, Wiley VCH (2005) and in earlier reviews: Matteson, D. S. (1988). Asymmetric synthesis with boronic esters. Accounts of Chemical Research, 21(8), 294-300, and Matteson, D. S. (1989). Tetrahedron, 45(7), 1859-1885), all of which are incorporated herein by reference in their entirety. The latter review articles also describe methodology for stereoselective insertion of halomethine functionality next to the boronate which is employed in the synthetic schemes below.

In addition to standard acid-catalyzed deprotection, special methods for removal of boronic acid protecting and/or stereodirecting groups include methods using fluorides (Yuen, A. K. L., & Hutton, C. A. (2005). Tetrahedron Letters, 46(46), 7899-7903—incorporated herein by reference in its entirety) or periodate oxidation (Coutts, S. J., et al. (1994). Tetrahedron Letters, 35(29), 5109-5112—incorporated herein by reference in its entirety) can also be employed in preparations of the compounds disclosed herein.

In strategies employing pinanediol or other diol-based chiral auxiliaries for stereospecific introduction of new chiral centers, the early stages of chemistry on boronic intermediates can be performed on chiral boronate esters or alternatively nonchiral borate/boronate intermediates can be used in early stages followed by transesterification with chiral diols prior to the step where stereoselection is required.

Synthesis of Compounds of Formula I

The following example schemes are provided for the guidance of the reader, and collectively represent an example method for making the compounds encompassed herein. Furthermore, other methods for preparing compounds described herein will be readily apparent to the person of ordinary skill in the art in light of the following reaction schemes and examples. Unless otherwise indicated, all variables are as defined above.

Compounds of Formula (Ia) where R is H can be prepared as depicted in Schemes 1-11 from key intermediates V', XIII' and XX' and XXVI', which may be assembled by known reactions (Boronic Acids: Preparations and Applications in Organic Synthesis, Medicine and Materials, D. G. Hall, ed., Wiley-VCH, Weinheim, 2011, which is incorporated herein by reference in its entirety). Methods in the following section are defined for pure enantiomers of Formula (Ia). These methods are also applicable to make compounds of other enantiomer, Formula (Ic) or to make a racemic mixture by modifying the stereo-defining step.

Scheme 1

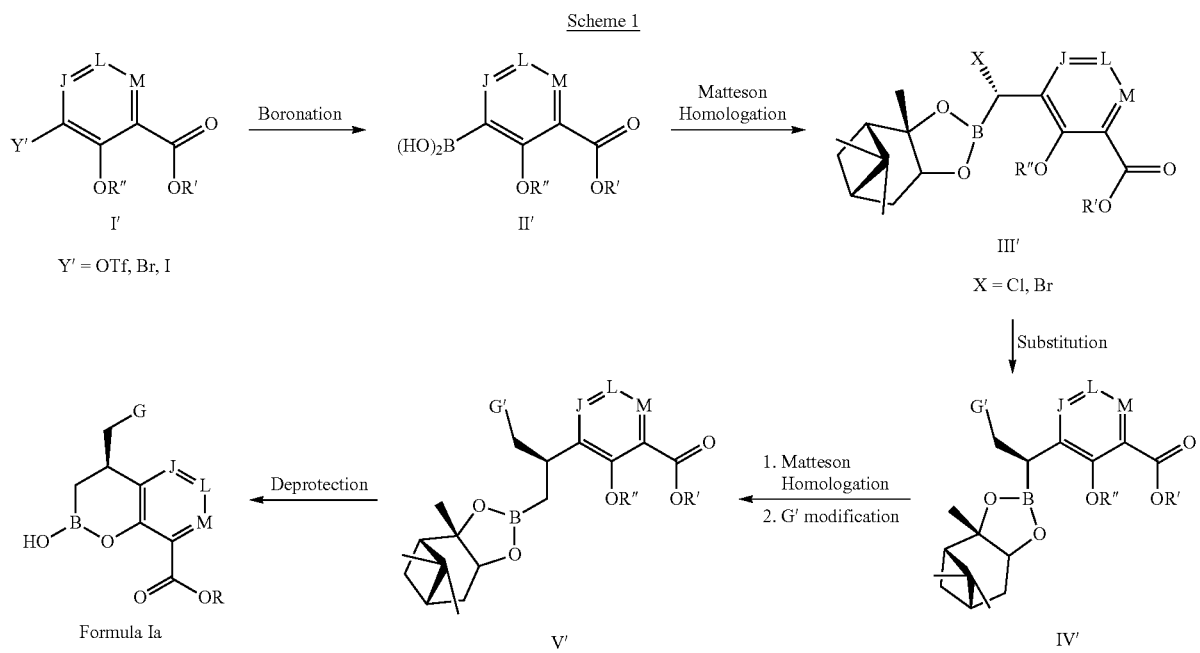

Compounds of Formula (Ia) can be made starting from protected aryl or heteroaryl intermediates of Formula II' via a double Matteson homologation sequence (*J. Org. Chem.*, 2013, 78, 10009-10023, which is incorporated herein by reference in its entirety). The compounds of Formula II' may be attained from compounds of Formula I' by means of several earlier known methods (WO0458679, which is incorporated herein by reference in its entirety) with conventional protecting groups for R' and R", such as those described in *Protective Groups in Organic Chemistry* (ed. J. F. W. McOmie, Plenum, 1973, which is incorporated herein by reference in its entirety); and *Protecting Groups in Organic Synthesis* P. G. M. Wutts, T. W. Green, Wiley, New York, 1999, which is incorporated herein by reference in its entirety) from commercially available salicylic acid derivatives. Aryl compounds of Formula I' upon boronation by well-known available methods (*Chem. Rev.* 2010, 110, 890-931, which is incorporated herein by reference in its entirety) and boronate ester formation with desired chiral auxiliary give precursor for Matteson homologation. Compounds of Formula III' where X=Cl and R' is Boc and R" is t-Butyl or R' and R" are protected together as isopropylidine or any other groups protected separately or together in cyclic form may be made from compounds of Formula II' via homologation upon chloromethylene insertion with good stereocontrol by Matteson reaction conditions (WO0946098, which is incorporated herein by reference in its entirety). Compounds of Formula III' where X is bromo may be made analogously to the chloro compounds of Scheme 1, utilizing dibromomethane (*J. Am. Chem. Soc.* 1990, 112, 3964-969, which is incorporated herein by reference in its entirety). The halo derivatives of Formula III' where X is Cl or Br undergo stereospecific substitution by vinyl magnesium halide or allyl magnesium halide or enolate of t-butyl acetate (*Tetrahedron* 2005, 61, 4427-4536, which is incorporated herein by reference in its entirety), to give compounds of Formula IV'. These intermediates of Formula IV' can be further treated to a non-substituted methylene homologation under Matteson reaction conditions. Such resulting intermediates can be further modified by conversion of G' groups to G substitution. G' groups such as vinyl or allyl functionalities can be converted to corresponding alcohols or acids or aldehydes by periodate oxidation or ozonolysis. Aldehyde functionalities can be converted to substituted amines by reductive amination to G-substituted compounds of Formula V'.

Simultaneous deprotection of pinane ester and salicylic acid protective groups of compounds of Formula V' can be achieved by heating with dilute HCl, affording the desired compounds of Formula (Ia). This transformation may also be achieved by treatment with $BCl_3$ or $BBr_3$ (WO09064414, which is incorporated herein by reference in its entirety). Alternatively, the deprotection may be attained via transesterification with isobutyl boronic acid in presence of dilute acid (WO09064413, which is incorporated herein by reference in its entirety) or via other known methods (*J. Org. Chem.* (2010), 75, 468-471, which is incorporated herein by reference in its entirety).

Salicylic acid derivatives of Formula I' where Y' is a leaving group undergo coupling reaction with Reformatsky reagent of acetate in Negishi conditions to give intermediates of Formula VI' where X' is OR'" (*Tetrahedron*, 2014, 1508-1515, *J. Org. Chem.*, 2013, 78, 8250-8266, which is incorporated herein by reference in its entirety) (Scheme 2). Such intermediates may be alkylated with halomethylene boronate derivative VIIA, followed by modification of ester by selective hydrolysis and reduction to give compounds of Formula V' in high stereoselectivity (*J. Am. Chem. Soc.*, 2011, 133, 11936-11939, which is incorporated herein by reference in its entirety). Intermediates of Formula VI' undergo methylenation to give derivatives of VII' (*J. Org. Chem.*, 1986, 51, 2981-2988, which is incorporated herein by reference in its entirety). Intermediates of Formula VII' undergo asymmetric boronation in known conditions to give compounds of Formula V' (*J. Am. Chem. Soc.*, 2010, 132, 10630-10633, which is incorporated herein by reference in its entirety). Such asymmetric boronation may also feasible where X' is $-NOR^1$. Intermediates of Formula V' can be further transformed to compound of Formula (Ia) under the conditions described in Scheme 1.

Scheme 2

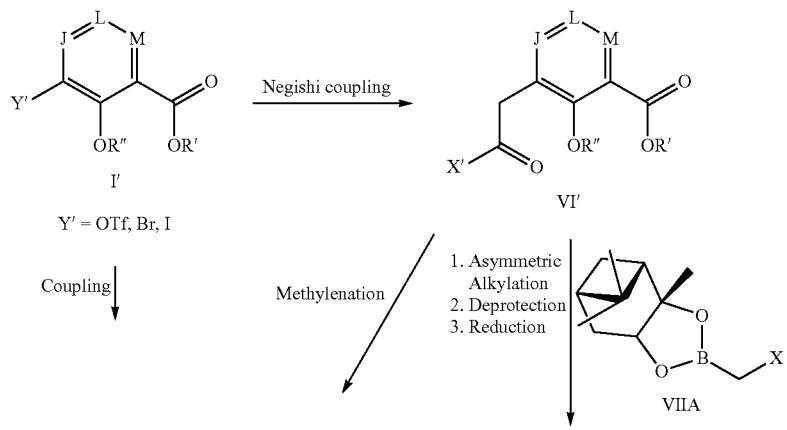

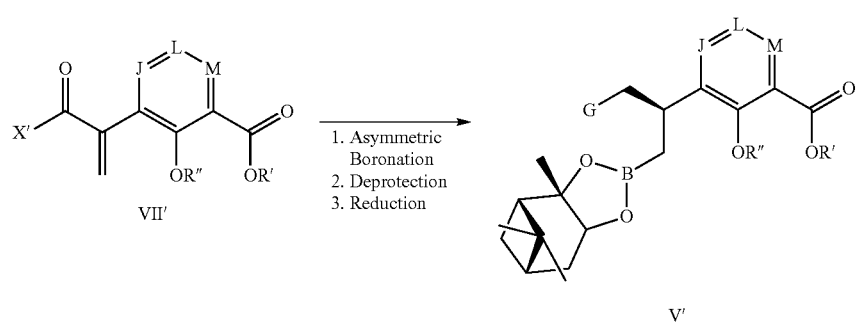

In an alternative sequence, compounds of Formula (Ia) can be made via boracarboxylation followed by asymmetric hydrogenation of acetylene intermediates of Formula VIII' as shown in Scheme 3. Aryl or heteroaryl derivatives Formula I' undergo a Pd-mediated coupling reaction to give an acetylene-substituted compound with TMS-acetylene. Boracarboxylation of alkynes with a diborane compound and carbon dioxide in presence of an N-heterocyclic carbene copper (I) complex as a catalyst gives α,β-unsaturated θ-boralactone derivatives regio- and stereoselectively via a borylcupration/carboxylation (*J. Am. Chem. Soc.* 2012, 134, 14314-14317, which is incorporated herein by reference in its entirety). Such resulting derivatives can be transformed to esters of carboxylate and boronate to give intermediates of Formula IX'. Asymmetric hydrogenation of intermediates of Formula IX' (*Chem. Rev.* 2003, 103, 3029-3070, which is incorporated herein by reference in its entirety) can be utilized to give enantiomerically pure compounds of Formula X'. Such compounds may be further transformed to compounds of Formula V' by selective hydrolysis and reduction to give appropriate G substitution which on final deprotection gives compounds of Formula (Ia) via the steps as described above in Scheme 1.

Scheme 3

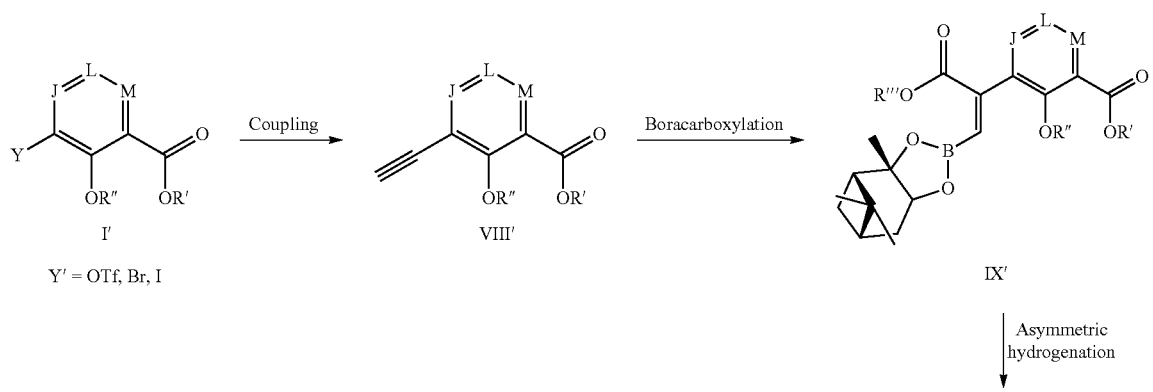

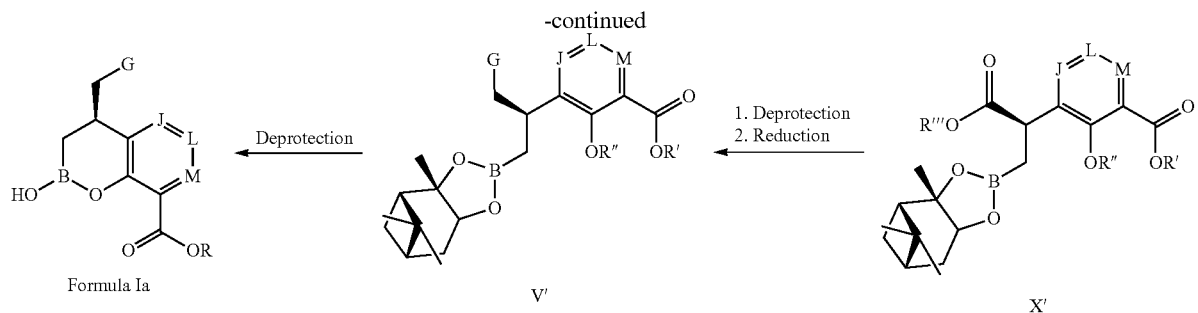

Compounds of Formula (Ia) where G=—NR¹C(O)R⁴, —NR¹C(O)NR¹R², or —NR¹C(O)OR³ may be prepared from carboxylic acid esters of Formula XI' (obtained via compounds of Formula V' where G is —CH₂CO₂ᵗBu and R' and R" together are protected isopropylidene) as shown in Scheme 4. Such compounds may be converted to amides via selective t-Butyl ester hydrolysis and Curtius rearrangement (*Chem. Rev.* 1988, 88, 297-368; *Org. Lett.*, 2005, 4107-4110, which are incorporated herein by reference in the entirety) followed by deprotection and amide formation to give compounds of Formula XIII'. Compounds of Formula XII' may also be transformed to compounds of Formula (Ia) where G is —NHC(O)—O—R by hydrolysis.

Scheme 4

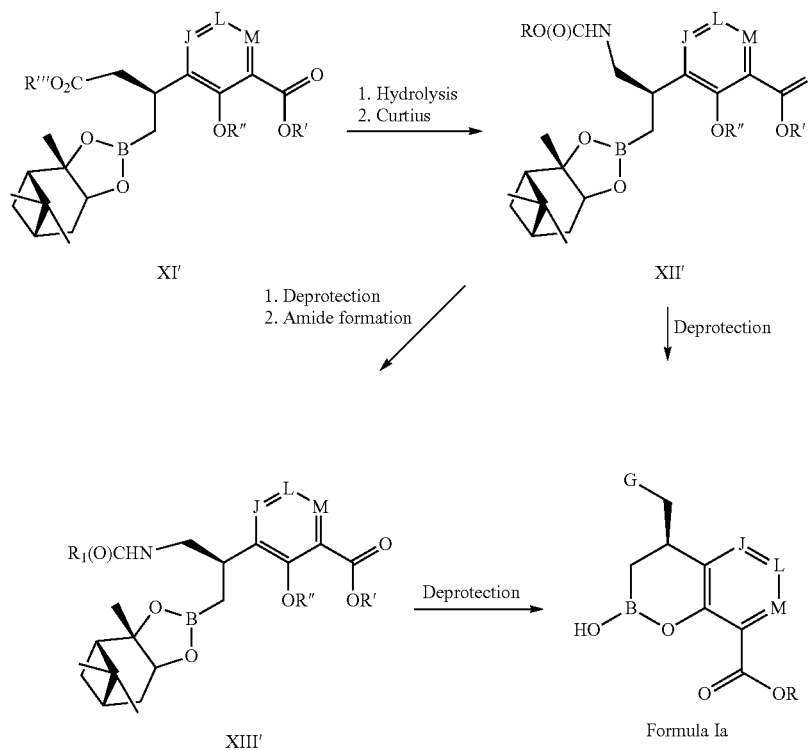

In an alternate route as shown in Scheme 5, compounds of Formula (Ia) can be obtained via intermediates of Formula XVII'. Such intermediates of Formula XVII' can be assembled by asymmetric hydroboration (*J. Am. Chem. Soc.* 2014, 136, 15501-15504) and trans-esterification of 1,1'-disubstituted alkenes of Formula XVI'. Intermediates of Formula XVI' can be obtained by coupling of substituted 2-bromo-propene derivatives with boronic acids of Formula XIV' by palladium-catalyzed reactions. Intermediates of Formula XVII' can be further transformed to compounds of Formula V' by converting the G' group to G (from esters to acids by selective hydrolysis followed by conversion to alcohols or amides) utilizing transformations shown in Schemes 3 and 4.

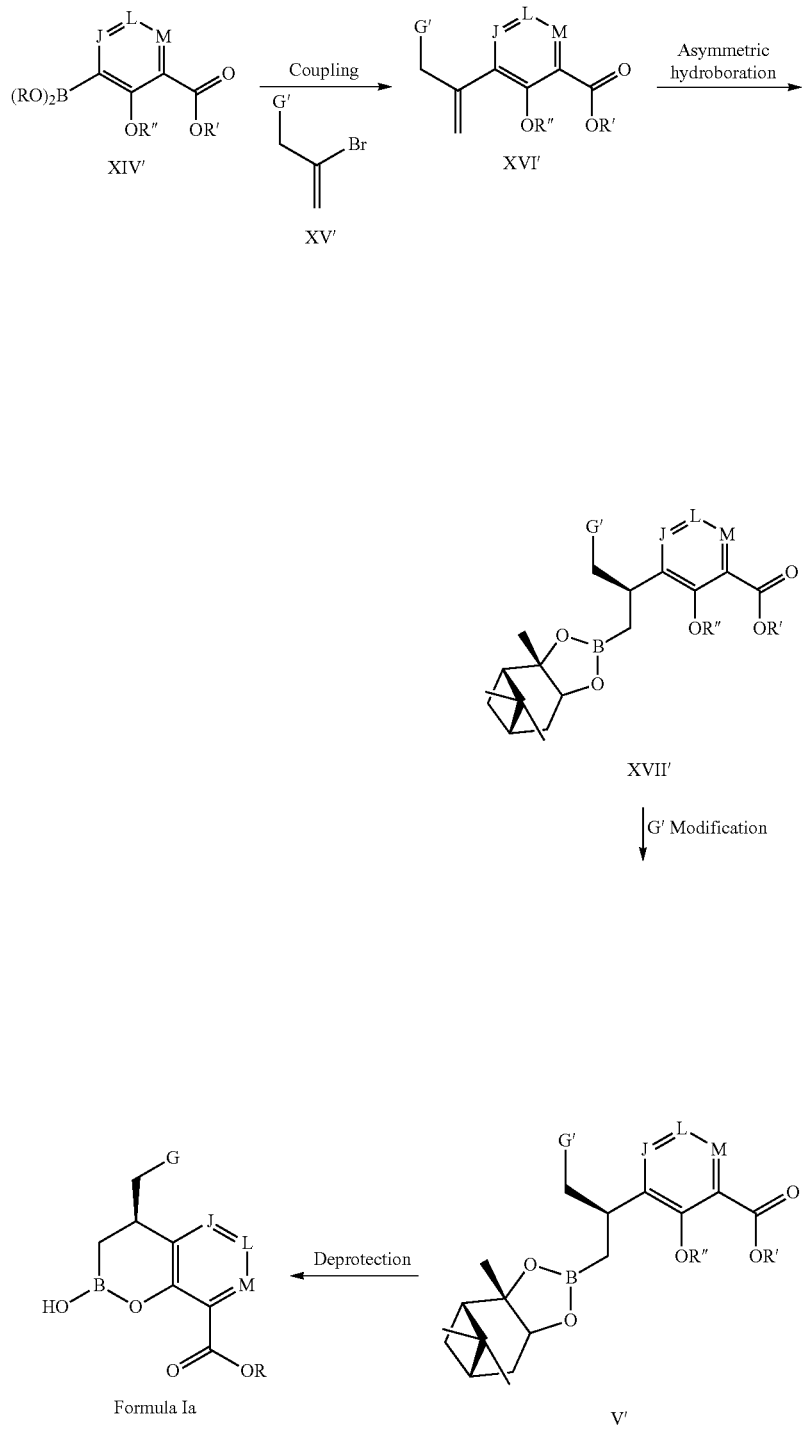

Compounds of Formula (Ia) can also be assembled in a convergent method as shown in Scheme 6 via intermediates of Formula XX'. Such intermediates of Formula XX' are made by coupling of substituted diboronate precursors of Formula XIX' (*Org. Lett.*, 2014, 16, 6240-6243) with precursors of Formula I' by palladium catalysis. Diboronates of Formula XIX' are prepared from propargyl derivatives of Formula XVIII' by utilizing an Ir-catalyzed method (*J. Am. Chem. Soc.*, 2010, 132, 2548-2549). Such intermediates of Formula XX' (where G' can be —OTIPS or —CO$_2$Me or —CONR'R" for further modification or deprotection) are known to undergo enantioselective hydrogenation (*Angew. Chem. Int. Ed.*, 2011, 50, 1-6; *Chem. Eur. J.*, 2012, 18, 6724-6728) to result in intermediates of Formula XXI'. Modification of G' group to G and deprotection of XXI', as described above leads to compounds of Formula (Ia).

Scheme 6

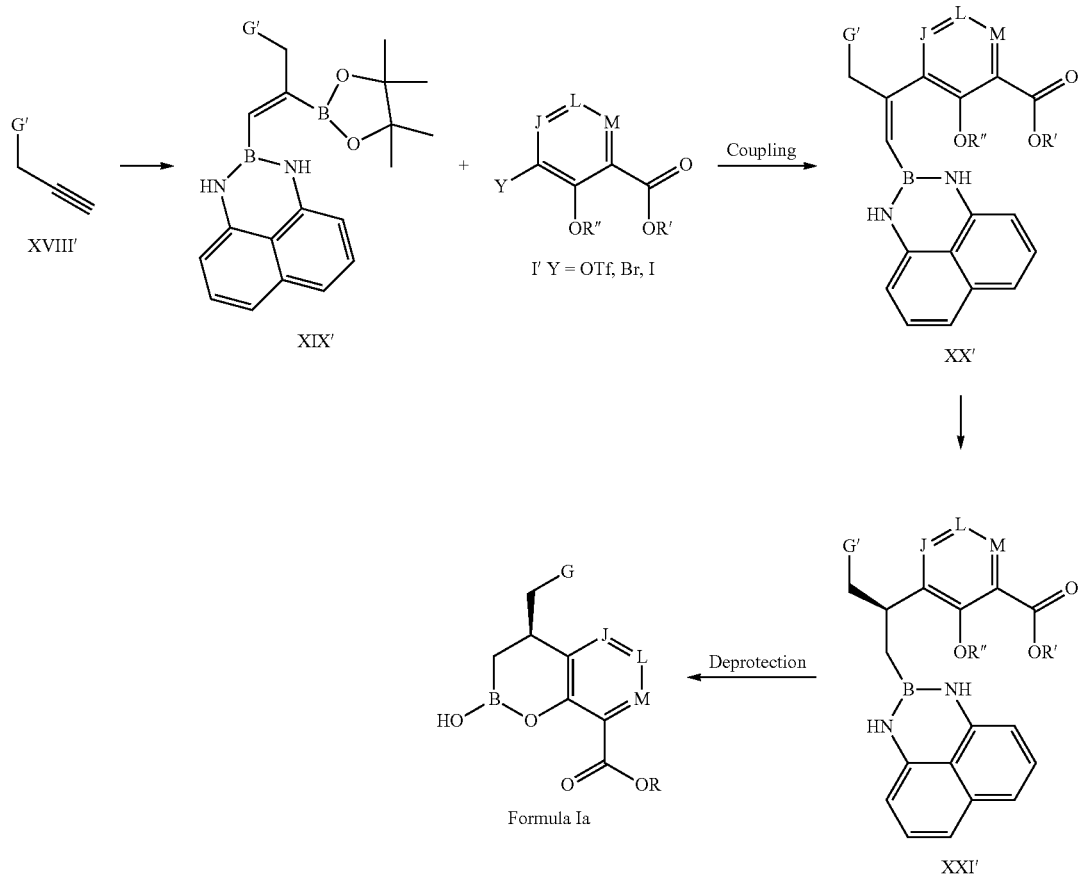

In an alternative synthetic route shown below, compounds of Formula (Ia) can be made via nickel-catalyzed boron-insertion (*J. Am. Chem. Soc.*, 2016, 138, 15315-15318) of benzofuran derivatives of Formula XXV' to give intermediates of Formula XXVI'. Such oxaborinane intermediates upon enantioselective hydrogenation (*Angew. Chem. Int. Ed.*, 2011, 50, 1-6; *Chem. Eur. J.*, 2012, 18, 6724-6728) followed by modification of G' group and deprotection give compounds of Formula (Ia). Benzofuran derivatives of Formula XXV' can be made by several known diverse methods including cyclization of intermediates of Formula XXIV' (*Org. Biomol. Chem.*, 2016, 14, 8074-8087). Such intermediates of Formula XXIV' can be obtained via alkylation of appropriately substituted phenol derivatives of Formula XXIII' with substituted bromoacetone derivatives of Formula XXII' (*Tetrahedron*, 2013, 69, 5937-5944).

Scheme 7

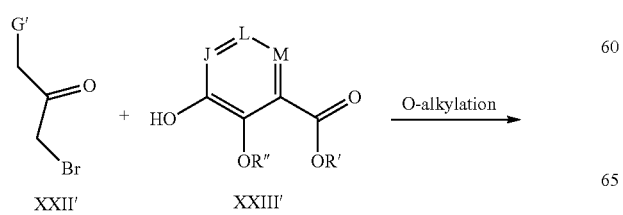

-continued

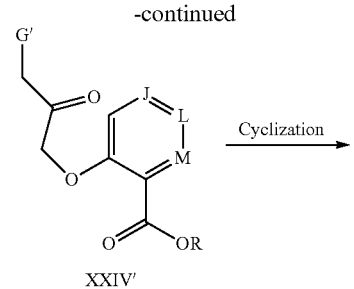

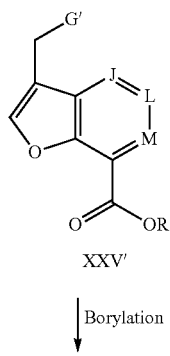

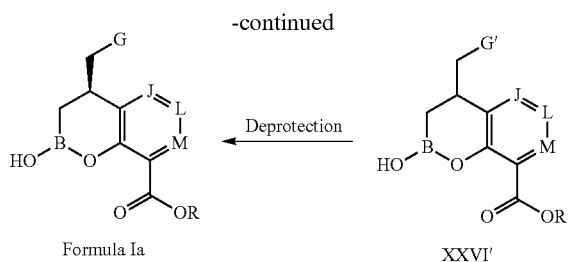

Intermediates of Formula XXIX', which may alternatively be featured in routes to attain compounds of Formula (Ia) may be prepared as shown in Scheme 8. Such intermediates of Formula XXIX' can be synthesized from compounds of Formula XXVII' where X' is a triflate, bromo, or iodo group by utilizing a Reformatsky reagent of a bromomethylene acetate ester (*J. Org. Chem.*, 2013, 78, 8250-8266; *Chem Lett.*, 1993, 845-848, which are incorporated herein by reference in the entirety). Compounds of Formula XXVIII' where X' is substituted with bromo or iodo groups can be attained from appropriately protected commercial 2,5-hydroxy-benzoic acid derivatives (*J. Med. Chem.*, 2003, 46, 3437-3440, which is incorporated herein by reference in its entirety). Intermediates of Formula XXXVIII' can also be prepared via carboxylation of derivatives of Formula XXXVII' where Z' is a fluoro or OR' or SR' by earlier described methods (WO12106995, which is incorporated herein by reference in its entirety).

Scheme 8

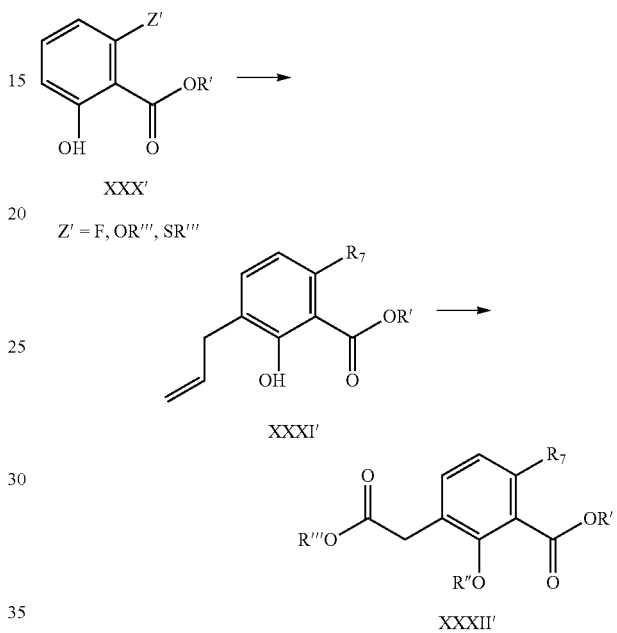

In another exemplary synthetic route, as shown in Scheme 9, the compounds of Formula XXXII' can be prepared from a salicylic acid derivative of a compound of Formula XXXI'. The compounds of Formula XXX' upon diallylation under basic conditions followed by thermal Claisen rearrangement (*Org. React.* 1975, 22, 1-252, which is incorporated herein by reference in its entirety) and ester hydrolysis give compounds of Formula XXXI'. Such compounds upon protection and oxidation followed by esterification result in phenylacetic acid derivatives of Formula XXXII'. Compounds of Formula XXXII' can be further transformed as shown above in Scheme 2. The compound of formula XXX' can also undergo the steps listed above in Scheme 8 to form an ortho-carboxylate-substituted compound of Formula XXIX'.

Synthesis of Prodrugs

Compounds of Formula (Ia) where the R is a prodrug moiety may be synthesized by a variety of known methods of producing different carboxylic acid prodrugs (*Prodrugs: Challenges and Rewards*, V. J. Stella, et al., ed., Springer, New York, 2007, which is incorporated herein by reference in its entirety). These prodrugs include but are not limited to substituted or non-substituted alkyl esters, (acyloxy)alkyl esters (Synthesis 2012, 44, 207, which is incorporated herein by reference in its entirety), [(alkoxycarbonyl)oxy]methyl esters (WO10097675, which is incorporated herein by reference in its entirety), or (oxodioxolyl)methyl esters (*J. Med. Chem.* 1996, 39, 323-338, which is incorporated herein by reference in its entirety). Such prodrugs can be made from compounds of Formula (Ia) where R=H (Formula XXXIII') by treatment with acid or in neutral conditions (e.g., carbodiimide coupling) in the presence of alcohols (ROH) or via base-promoted esterification with RX where X is a leaving group in the presence of an appropriate base.

One exemplary but non-limiting general synthetic route for preparing prodrugs is shown in Scheme 10 below. The boronic acid of Formula XXXIII' can react with a chloro- or bromo-substituted prodrug moiety to form a prodrug of Formula (Ia) where R is a prodrug moiety. Examples of the prodrug moiety R can be —$C_{1-9}$ alkyl, —$CR^9R^{10}OC(O)C_{1-9}$ alkyl, —$CR^9R^{10}OC(O)OC_{1-9}$alkyl, —$CR^9R^{10}OC(O)$ $C_{3-7}$ carbocyclyl, —$CR^9R^{10}OC(O)OC_{3-7}$ carbocyclyl; —$CR^9R^{10}OC(O)(5\text{-}10$ membered heterocyclyl), —$CR^9R^{10}OC(O)O$ (5-10 membered heterocyclyl), and

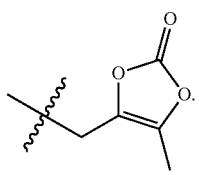 [SMILES: *Cc1oc(=O)oc1C]

Scheme 10

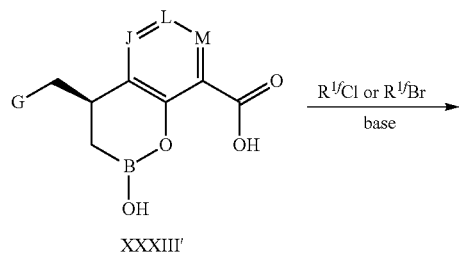

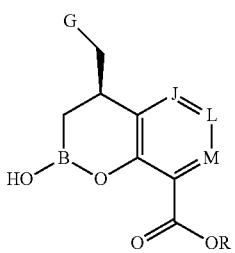

Formula Ia

Alternatively, boronate esters of Formula XXXIV' or corresponding trifluoroborates (*Chem. Rev.* 2008, 108, 288-325, which is incorporated herein by reference in its entirety) may be also utilized for introduction of prodrugs and to convert them to final prodrugs (Scheme 11). Such carboxylic acids (XXXIV') can be made from compounds of Formula V' by selective deprotection of OR'. The prodrug group may also be introduced earlier in the sequence in compounds of Formula IV' where R' is R. Such a sequence in which a prodrug is introduced in earlier intermediates is only feasible when the ester is stable enough under the final deprotection conditions to remove the phenol protective group and boronate ester group.

Scheme 11

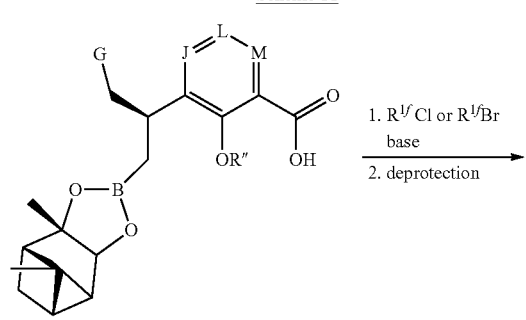

XXXIV'

Administration and Pharmaceutical Compositions

The compounds are administered at a therapeutically effective dosage. While human dosage levels have yet to be optimized for the compounds described herein, generally, a daily dose may be from about 0.25 mg/kg to about 120 mg/kg or more of body weight, from about 0.5 mg/kg or less to about 70 mg/kg, from about 1.0 mg/kg to about 50 mg/kg of body weight, or from about 1.5 mg/kg to about 10 mg/kg of body weight. Thus, for administration to a 70 kg person, the dosage range would be from about 17 mg per day to about 8000 mg per day, from about 35 mg per day or less to about 7000 mg per day or more, from about 70 mg per day to about 6000 mg per day, from about 100 mg per day to about 5000 mg per day, or from about 200 mg to about 3000 mg per day. The amount of active compound administered will, of course, be dependent on the subject and disease state being treated, the severity of the affliction, the manner and schedule of administration and the judgment of the prescribing physician.

Administration of the compounds disclosed herein or the pharmaceutically acceptable salts thereof can be via any of the accepted modes of administration for agents that serve similar utilities including, but not limited to, orally, subcutaneously, intravenously, intranasally, topically, transdermally, intraperitoneally, intramuscularly, intrapulmonarilly, vaginally, rectally, or intraocularly. Oral and parenteral administrations are customary in treating the indications that are the subject of the preferred embodiments.

The compounds useful as described above can be formulated into pharmaceutical compositions for use in treatment of these conditions. Standard pharmaceutical formulation techniques are used, such as those disclosed in Remington's The Science and Practice of Pharmacy, 21st Ed., Lippincott Williams & Wilkins (2005), incorporated by reference in its entirety. Accordingly, some embodiments include pharmaceutical compositions comprising: (a) a safe and therapeutically effective amount of a compound described herein (including enantiomers, diastereoisomers, tautomers, polymorphs, and solvates thereof), or pharmaceutically acceptable salts thereof; and (b) a pharmaceutically acceptable carrier, diluent, excipient or combination thereof.

In addition to the selected compound useful as described above, come embodiments include compositions containing a pharmaceutically-acceptable carrier. The term "pharmaceutically acceptable carrier" or "pharmaceutically acceptable excipient" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. In addition, various adjuvants such as are commonly used in the art may be included. Considerations for the inclusion of various components in pharmaceutical compositions are described, e.g., in Gilman et al. (Eds.) (1990); Goodman and Gilman's: The Pharmacological Basis of Therapeutics, 8th Ed., Pergamon Press, which is incorporated herein by reference in its entirety.

Some examples of substances, which can serve as pharmaceutically-acceptable carriers or components thereof, are sugars, such as lactose, glucose and sucrose; starches, such as corn starch and potato starch; cellulose and its derivatives, such as sodium carboxymethyl cellulose, ethyl cellulose, and methyl cellulose; powdered tragacanth; malt; gelatin; talc; solid lubricants, such as stearic acid and magnesium stearate; calcium sulfate; vegetable oils, such as peanut oil, cottonseed oil, sesame oil, olive oil, corn oil and oil of theobroma; polyols such as propylene glycol, glycerine, sorbitol, mannitol, and polyethylene glycol; alginic acid; emulsifiers, such as the TWEENS; wetting agents, such sodium lauryl sulfate; coloring agents; flavoring agents; tableting agents, stabilizers; antioxidants; preservatives; pyrogen-free water; isotonic saline; and phosphate buffer solutions.

The choice of a pharmaceutically-acceptable carrier to be used in conjunction with the subject compound is basically determined by the way the compound is to be administered.

The compositions described herein are preferably provided in unit dosage form. As used herein, a "unit dosage form" is a composition containing an amount of a compound that is suitable for administration to an animal, preferably mammal subject, in a single dose, according to good medical practice. The preparation of a single or unit dosage form however, does not imply that the dosage form is administered once per day or once per course of therapy. Such dosage forms are contemplated to be administered once, twice, thrice or more per day and may be administered as infusion over a period of time (e.g., from about 30 minutes to about 2-6 hours), or administered as a continuous infusion, and may be given more than once during a course of therapy, though a single administration is not specifically excluded. The skilled artisan will recognize that the formulation does not specifically contemplate the entire course of therapy and such decisions are left for those skilled in the art of treatment rather than formulation.

The compositions useful as described above may be in any of a variety of suitable forms for a variety of routes for administration, for example, for oral, nasal, rectal, topical (including transdermal), ocular, intracerebral, intracranial, intrathecal, intra-arterial, intravenous, intramuscular, or other parental routes of administration. The skilled artisan will appreciate that oral and nasal compositions comprise compositions that are administered by inhalation, and made using available methodologies. Depending upon the particular route of administration desired, a variety of pharmaceutically-acceptable carriers well-known in the art may be used. Pharmaceutically-acceptable carriers include, for example, solid or liquid fillers, diluents, hydrotropies, surface-active agents, and encapsulating substances. Optional pharmaceutically-active materials may be included, which do not substantially interfere with the inhibitory activity of the compound. The amount of carrier employed in conjunction with the compound is sufficient to provide a practical quantity of material for administration per unit dose of the compound. Techniques and compositions for making dosage forms useful in the methods described herein are described in the following references, all incorporated by reference herein: Modern Pharmaceutics, 4th Ed., Chapters 9 and 10 (Banker & Rhodes, editors, 2002); Lieberman et al., Pharmaceutical Dosage Forms: Tablets (1989); and Ansel, Introduction to Pharmaceutical Dosage Forms 8th Edition (2004).

Various oral dosage forms can be used, including such solid forms as tablets, capsules, granules and bulk powders. Tablets can be compressed, tablet triturates, enteric-coated, sugar-coated, film-coated, or multiple-compressed, containing suitable binders, lubricants, diluents, disintegrating agents, coloring agents, flavoring agents, flow-inducing agents, and melting agents. Liquid oral dosage forms include aqueous solutions, emulsions, suspensions, solutions and/or suspensions reconstituted from non-effervescent granules, and effervescent preparations reconstituted from effervescent granules, containing suitable solvents, preservatives, emulsifying agents, suspending agents, diluents, sweeteners, melting agents, coloring agents and flavoring agents.

The pharmaceutically-acceptable carrier suitable for the preparation of unit dosage forms for peroral administration is well-known in the art. Tablets typically comprise conventional pharmaceutically-compatible adjuvants as inert diluents, such as calcium carbonate, sodium carbonate, mannitol, lactose and cellulose; binders such as starch, gelatin and sucrose; disintegrants such as starch, alginic acid and croscarmelose; lubricants such as magnesium stearate, stearic acid and talc. Glidants such as silicon dioxide can be used to improve flow characteristics of the powder mixture. Coloring agents, such as the FD&C dyes, can be added for appearance. Sweeteners and flavoring agents, such as aspartame, saccharin, menthol, peppermint, and fruit flavors, are useful adjuvants for chewable tablets. Capsules typically comprise one or more solid diluents disclosed above. The selection of carrier components depends on secondary considerations like taste, cost, and shelf stability, which are not critical, and can be readily made by a person skilled in the art.

Peroral compositions also include liquid solutions, emulsions, suspensions, and the like. The pharmaceutically-acceptable carriers suitable for preparation of such compositions are well known in the art. Typical components of carriers for syrups, elixirs, emulsions and suspensions include ethanol, glycerol, propylene glycol, polyethylene glycol, liquid sucrose, sorbitol and water. For a suspension, typical suspending agents include methyl cellulose, sodium carboxymethyl cellulose, AVICEL RC-591, tragacanth and sodium alginate; typical wetting agents include lecithin and polysorbate 80; and typical preservatives include methyl paraben and sodium benzoate. Peroral liquid compositions may also contain one or more components such as sweeteners, flavoring agents and colorants disclosed above.

Such compositions may also be coated by conventional methods, typically with pH or time-dependent coatings, such that the subject compound is released in the gastrointestinal tract in the vicinity of the desired topical application, or at various times to extend the desired action. Such dosage forms typically include, but are not limited to, one or more of cellulose acetate phthalate, polyvinylacetate phthalate, hydroxypropyl methyl cellulose phthalate, ethyl cellulose, Eudragit coatings, waxes and shellac.

Compositions described herein may optionally include other drug actives.

Other compositions useful for attaining systemic delivery of the subject compounds include sublingual, buccal and nasal dosage forms. Such compositions typically comprise one or more of soluble filler substances such as sucrose, sorbitol and mannitol; and binders such as acacia, microcrystalline cellulose, carboxymethyl cellulose and hydroxypropyl methyl cellulose. Glidants, lubricants, sweeteners, colorants, antioxidants and flavoring agents disclosed above may also be included.

A liquid composition, which is formulated for topical ophthalmic use, is formulated such that it can be administered topically to the eye. The comfort should be maximized as much as possible, although sometimes formulation considerations (e.g. drug stability) may necessitate less than optimal comfort. In the case that comfort cannot be maximized, the liquid should be formulated such that the liquid is tolerable to the patient for topical ophthalmic use. Additionally, an ophthalmically acceptable liquid should either be packaged for single use, or contain a preservative to prevent contamination over multiple uses.

For ophthalmic application, solutions or medicaments are often prepared using a physiological saline solution as a major vehicle. Ophthalmic solutions should preferably be maintained at a comfortable pH with an appropriate buffer system. The formulations may also contain conventional, pharmaceutically acceptable preservatives, stabilizers and surfactants.

Preservatives that may be used in the pharmaceutical compositions disclosed herein include, but are not limited to, benzalkonium chloride, PHMB, chlorobutanol, thimerosal, phenylmercuric, acetate and phenylmercuric nitrate. A useful surfactant is, for example, Tween 80. Likewise, various useful vehicles may be used in the ophthalmic preparations disclosed herein. These vehicles include, but are not limited to, polyvinyl alcohol, povidone, hydroxypropyl methyl cellulose, poloxamers, carboxymethyl cellulose, hydroxyethyl cellulose and purified water.

Tonicity adjustors may be added as needed or convenient. They include, but are not limited to, salts, particularly sodium chloride, potassium chloride, mannitol and glycerin, or any other suitable ophthalmically acceptable tonicity adjustor.

Various buffers and means for adjusting pH may be used so long as the resulting preparation is ophthalmically acceptable. For many compositions, the pH will be between 4 and 9. Accordingly, buffers include acetate buffers, citrate buffers, phosphate buffers and borate buffers. Acids or bases may be used to adjust the pH of these formulations as needed.

In a similar vein, an ophthalmically acceptable antioxidant includes, but is not limited to, sodium metabisulfite, sodium thiosulfate, acetylcysteine, butylated hydroxyanisole and butylated hydroxytoluene.

Other excipient components, which may be included in the ophthalmic preparations, are chelating agents. A useful chelating agent is edetate disodium, although other chelating agents may also be used in place or in conjunction with it.

For topical use, creams, ointments, gels, solutions or suspensions, etc., containing the compound disclosed herein are employed. Topical formulations may generally be comprised of a pharmaceutical carrier, co-solvent, emulsifier, penetration enhancer, preservative system, and emollient.

For intravenous administration, the compounds and compositions described herein may be dissolved or dispersed in a pharmaceutically acceptable diluent, such as a saline or dextrose solution. Suitable excipients may be included to achieve the desired pH, including but not limited to NaOH, sodium carbonate, sodium acetate, HCl, and citric acid. In various embodiments, the pH of the final composition ranges from 2 to 8, or preferably from 4 to 7. Antioxidant excipients may include sodium bisulfite, acetone sodium bisulfite, sodium formaldehyde, sulfoxylate, thiourea, and EDTA. Other non-limiting examples of suitable excipients found in the final intravenous composition may include sodium or potassium phosphates, citric acid, tartaric acid, gelatin, and carbohydrates such as dextrose, mannitol, and dextran. Further acceptable excipients are described in Powell, et al., Compendium of Excipients for Parenteral Formulations, *PDA J Pharm Sci and Tech* 1998, 52 238-311 and Nema et al., Excipients and Their Role in Approved Injectable Products: Current Usage and Future Directions, *PDA J Pharm Sci and Tech* 2011, 65 287-332, both of which are incorporated herein by reference in their entirety. Antimicrobial agents may also be included to achieve a bacteriostatic or fungistatic solution, including but not limited to phenylmercuric nitrate, thimerosal, benzethonium chloride, benzalkonium chloride, phenol, cresol, and chlorobutanol.

The compositions for intravenous administration may be provided to caregivers in the form of one more solids that are reconstituted with a suitable diluent such as sterile water, saline or dextrose in water shortly prior to administration. In other embodiments, the compositions are provided in solution ready to administer parenterally. In still other embodiments, the compositions are provided in a solution that is further diluted prior to administration. In embodiments that include administering a combination of a compound described herein and another agent, the combination may be provided to caregivers as a mixture, or the caregivers may mix the two agents prior to administration, or the two agents may be administered separately.

The actual dose of the active compounds described herein depends on the specific compound, and on the condition to be treated; the selection of the appropriate dose is well within the knowledge of the skilled artisan.

Methods of Treatment

Some embodiments of the present invention include methods of treating bacterial infections with the compounds and compositions comprising the compounds described herein. Some methods include administering a compound, composition, pharmaceutical composition described herein to a subject in need thereof. In some embodiments, a subject can be an animal, e.g., a mammal (including a human). In some embodiments, the bacterial infection comprises a bacterium described herein. As will be appreciated from the foregoing, methods of treating a bacterial infection include methods for preventing bacterial infection in a subject at risk thereof.

In some embodiments, the subject is a human.

Further embodiments include administering a combination of compounds to a subject in need thereof. A combination can include a compound, composition, pharmaceutical composition described herein with an additional medicament.

Some embodiments include co-administering a compound, composition, and/or pharmaceutical composition described herein, with an additional medicament. By "co-administration," it is meant that the two or more agents may be found in the patient's bloodstream at the same time, regardless of when or how they are actually administered. In one embodiment, the agents are administered simultaneously. In one such embodiment, administration in combination is accomplished by combining the agents in a single dosage form. In another embodiment, the agents are administered sequentially. In one embodiment, the agents are administered through the same route, such as orally. In another embodiment, the agents are administered through different routes, such as one being administered orally and another being administered intravenously.

Examples of additional medicaments include an antibacterial agent, antifungal agent, an antiviral agent, an anti-inflammatory agent and an anti-allergic agent.

Preferred embodiments include combinations of a compound, composition or pharmaceutical composition described herein with an antibacterial agent such as a β-lactam. Examples of such β-lactams include Amoxicillin, Ampicillin (e.g., Pivampicillin, Hetacillin, Bacampicillin, Metampicillin, Talampicillin), Epicillin, Carbenicillin (Carindacillin), Ticarcillin, Temocillin, Azlocillin, Piperacillin, Mezlocillin, Mecillinam (Pivmecillinam), Sulbenicillin, Benzylpenicillin (G), Clometocillin, Benzathine benzylpenicillin, Procaine benzylpenicillin, Azidocillin, Penamecillin, Phenoxymethylpenicillin (V), Propicillin, Benzathine phenoxymethylpenicillin, Pheneticillin, Cloxacillin (e.g., Dicloxacillin, Flucloxacillin), Oxacillin, Methicillin, Nafcillin, Faropenem, Biapenem, Doripenem, Ertapenem, Imipenem, Meropenem, Panipenem, Cefazolin, Cefacetrile, Cefadroxil, Cefalexin, Cefaloglycin, Cefalonium, Cefaloridine, Cefalotin, Cefapirin, Cefatrizine, Cefazedone, Cefazaflur, Cefradine, Cefroxadine, Ceftezole, Cefaclor, Cefamandole, Cefminox, Cefonicid, Ceforanide, Cefotiam, Cefprozil, Cefbuperazone, Cefuroxime, Cefuzonam, Cefoxitin, Cefotetan, Cefmetazole, Loracarbef, Cefixime, Ceftazidime, Ceftriaxone, Cefcapene, Cefdaloxime, Cefdinir, Cefditoren, Cefetamet, Cefmenoxime, Cefodizime, Cefoperazone, Cefotaxime, Cefpimizole, Cefpiramide, Cefpodoxime, Cefsulodin, Cefteram, Ceftibuten, Ceftiolene, Ceftizoxime, Flomoxef, Latamoxef, Cefepime, Cefozopran, Cefpirome, Cefquinome, Ceftobiprole, Ceftaroline, Ceftiofur, Cefquinome, Cefovecin, Aztreonam, Tigemonam, and Carumonam.

Preferred embodiments include β-lactams such as Ceftazidime, Biapenem, Doripenem, Ertapenem, Imipenem, Meropenem, Tebipenem, Tebipenem pivoxil, Apapenem, and Panipenem.

Additional preferred embodiments include β-lactams such as Aztreonam, Tigemonam, and Carumonam.

Some embodiments include a combination of the compounds, compositions and/or pharmaceutical compositions described herein with an additional agent, wherein the additional agent comprises a monobactam. Examples of monobactams include aztreonam, tigemonam, nocardicin A, carumonam, and tabtoxin. In some such embodiments, the compound, composition and/or pharmaceutical composition comprises a class A, C, or D β-lactamase inhibitor. Some embodiments include co-administering the compound, composition or pharmaceutical composition described herein with one or more additional agents.

Some embodiments include a combination of the compounds, compositions and/or pharmaceutical compositions described herein with an additional agent, wherein the additional agent comprises a class B β-lactamase inhibitor. An example of a class B β-lactamase inhibitor includes ME1071 (Yoshikazu Ishii et al, "In Vitro Potentiation of Carbapenems with ME1071, a Novel Metallo-β-Lactamase Inhibitor, against Metallo-β-lactamase Producing *Pseudomonas aeruginosa* Clinical Isolates." Antimicrob. Agents Chemother. doi:10.1128/AAC.01397-09 (July 2010)). Some embodiments include co-administering the compound, composition or pharmaceutical composition described herein with one or more additional agents.

Some embodiments include a combination of the compounds, compositions and/or pharmaceutical compositions described herein with an additional agent, wherein the additional agent comprises one or more agents that include a class A, B, C, or D β-lactamase inhibitor. Some embodiments include co-administering the compound, composition or pharmaceutical composition described herein with the one or more additional agents.

Indications

The compounds and compositions comprising the compounds described herein can be used to treat bacterial infections. Bacterial infections that can be treated with the compounds, compositions and methods described herein can comprise a wide spectrum of bacteria. Example organisms include gram-positive bacteria, gram-negative bacteria, aerobic and anaerobic bacteria, such as *Staphylococcus, Lactobacillus, Streptococcus, Sarcina, Escherichia, Enterobacter, Klebsiella, Pseudomonas, Acinetobacter, Mycobacterium, Proteus, Campylobacter, Citrobacter, Nisseria, Baccillus, Bacteroides, Peptococcus, Clostridium, Salmonella, Shigella, Serratia, Haemophilus, Brucella*, and other organisms.

More examples of bacterial infections include *Pseudomonas aeruginosa, Pseudomonas fluorescens, Pseudomonas acidovorans, Pseudomonas alcaligenes, Pseudomonas putida, Stenotrophomonas maltophilia, Burkholderia cepacia, Aeromonas hydrophilia, Escherichia coli, Citrobacter freundii, Salmonella typhimurium, Salmonella typhi, Salmonella paratyphi, Salmonella enteritidis, Shigella dysenteriae, Shigella flexneri, Shigella sonnei, Enterobacter cloacae, Enterobacter aerogenes, Klebsiella pneumoniae, Klebsiella oxytoca, Serratia marcescens, Francisella tularensis, Morganella morganii, Proteus mirabilis, Proteus vulgaris, Providencia alcalifaciens, Providencia rettgeri, Providencia stuartii, Acinetobacter baumannii, Acinetobacter calcoaceticus, Acinetobacter haemolyticus, Yersinia enterocolitica, Yersinia pestis, Yersinia pseudotuberculosis, Yersinia intermedia, Bordetella pertussis, Bordetella parapertussis, Bordetella bronchiseptica, Haemophilus influenzae, Haemophilus parainfluenzae, Haemophilus haemolyticus, Haemophilus parahaemolyticus, Haemophilus ducreyi, Pasteurella multocida, Pasteurella haemolytica, Branhamella catarrhalis, Helicobacter pylori, Campylobacter fetus, Campylobacter jejuni, Campylobacter coli, Borrelia burgdorferi, Vibrio cholerae, Vibrio parahaemolyticus, Legionella pneumophila, Listeria monocytogenes, Neisseria gonorrhoeae, Neisseria meningitidis, Kingella, Moraxella, Gardnerella vaginalis, Bacteroides fragilis, Bacteroides distasonis, Bacteroides* 3452A homology group, *Bacteroides vulgatus, Bacteroides ovalus, Bacteroides thetaiotaomicron, Bacteroides uniformis, Bacteroides eggerthii, Bacteroides splanchnicus, Clostridium difficile, Mycobacterium tuberculosis, Mycobacterium avium, Mycobacterium intracellulare, Mycobacterium leprae, Corynebacterium diphtheriae, Corynebacterium ulcerans, Streptococcus pneumoniae, Streptococcus agalactiae, Streptococcus pyogenes, Enterococcus faecalis, Enterococcus faecium, Staphylococcus aureus, Staphylococcus epidermidis, Staphylococcus saprophyticus, Staphylococcus intermedius, Staphylococcus hyicus* subsp. *hyicus, Staphylococcus haemolyticus, Staphylococcus hominis*, or *Staphylococcus saccharolyticus*.

To further illustrate this invention, the following examples are included. The examples should not, of course, be construed as specifically limiting the invention. Variations of these examples within the scope of the claims are within the purview of one skilled in the art and are considered to fall within the scope of the invention as described, and claimed herein. The reader will recognize that the skilled artisan, armed with the present disclosure, and skill in the art is able to prepare and use the invention without exhaustive examples. The following examples will further describe the present invention, and are used for the purposes of illustration only, and should not be considered as limiting.

EXAMPLES

General Procedures

Materials used in preparing the cyclic boronic acid ester derivatives described herein may be made by known methods or are commercially available. It will be apparent to the skilled artisan that methods for preparing precursors and functionality related to the compounds claimed herein are generally described in the literature including, for example, procedures described in U.S. Pat. No. 7,271,186 and WO2009064414, each of which is incorporated by reference in its entirety. In these reactions, it is also possible to make use of variants which are themselves known to those of ordinary skill in this art, but are not mentioned in greater detail. The skilled artisan given the literature and this disclosure is well equipped to prepare any of the compounds.

It is recognized that the skilled artisan in the art of organic chemistry can readily carry out manipulations without further direction, that is, it is well within the scope and practice of the skilled artisan to carry out these manipulations. These include reduction of carbonyl compounds to their corresponding alcohols, oxidations, acylations, aromatic substitutions, both electrophilic and nucleophilic, etherifications, esterification and saponification and the like. These manipulations are discussed in standard texts such as March Advanced Organic Chemistry (Wiley), Carey and Sundberg, Advanced Organic Chemistry (incorporated herein by reference in their entirety) and the like.

The skilled artisan will readily appreciate that certain reactions are best carried out when other functionality is masked or protected in the molecule, thus avoiding any undesirable side reactions and/or increasing the yield of the reaction. Often the skilled artisan utilizes protecting groups to accomplish such increased yields or to avoid the undesired reactions. These reactions are found in the literature and are also well within the scope of the skilled artisan. Examples of many of these manipulations can be found for example in T. Greene and P. Wuts Protecting Groups in Organic Synthesis, 4th Ed., John Wiley & Sons (2007), incorporated herein by reference in its entirety.

The following example schemes are provided for the guidance of the reader, and represent preferred methods for making the compounds exemplified herein. These methods are not limiting, and it will be apparent that other routes may be employed to prepare these compounds. Such methods specifically include solid phase based chemistries, including combinatorial chemistry. The skilled artisan is thoroughly equipped to prepare these compounds by those methods given the literature and this disclosure. The compound numberings used in the synthetic schemes depicted below are meant for those specific schemes only, and should not be construed as or confused with same numberings in other sections of the application.

Trademarks used herein are examples only and reflect illustrative materials used at the time of the invention. The skilled artisan will recognize that variations in lot, manufacturing processes, and the like, are expected. Hence the examples, and the trademarks used in them are non-limiting, and they are not intended to be limiting, but are merely an illustration of how a skilled artisan may choose to perform one or more of the embodiments of the invention.

The following abbreviations have the indicated meanings:
ACN or MeCN=acetonitrile
cod=cyclooctadiene
DCM=dichloromethane
DMF=N,N-dimethylformamide
DMAP=4-dimethylaminopyridine
dppf=1,1'-bis(diphenylphosphino)ferrocene
EDCI=N-(3-dimethylaminopropyl)-N'-ethylcarbodiimide hydrochloride
ESBL=extended-spectrum β-lactamase
EtOAc or EA=ethyl acetate
HATU=2-(7-aza-1H-benzotriazole-1-yl)-1,1,3,3-tetramethyluronium hexafluorophosphate
LDA=lithium diisopropylamide
MIC=minimum inhibitory concentration
NMR=nuclear magnetic resonance
PE=petroleum ether
RFC=radial flow chromatography
rt=room temperature
TBAF=tetrabutylammonium fluoride
TBSCl=tert-butyldimethylsilyl chloride
TBS=tert-butyldimethylsilyl
TES=triethylsilane
TFA=trifluoroacetic acid
TFAA=trifluoroacetic anhydride
THF=tetrahydrofuran
TIPS=triisopropylsilyl
TLC=thin layer chromatography The following example schemes are provided for the guidance of the reader, and collectively represent an example method for making the compounds provided herein. Furthermore, other methods for preparing compounds described herein will be readily apparent to the person of ordinary skill in the art in light of the following reaction schemes and examples. Unless otherwise indicated, all variables are as defined above.

Example 1

2-Hydroxy-4-(hydroxymethyl)-3,4-dihydro-1,2-benzoxaborinine-8-carboxylic Acid (Compound 1)

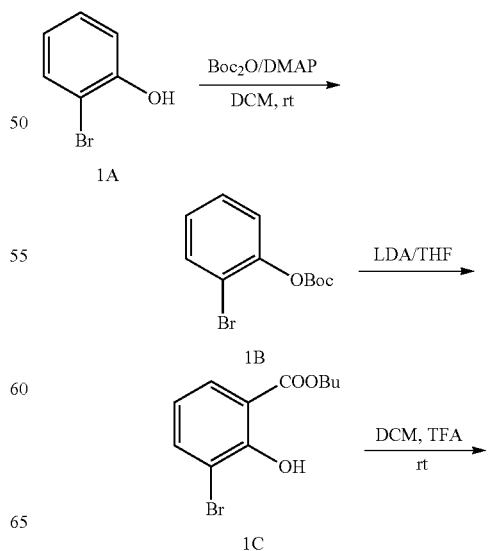

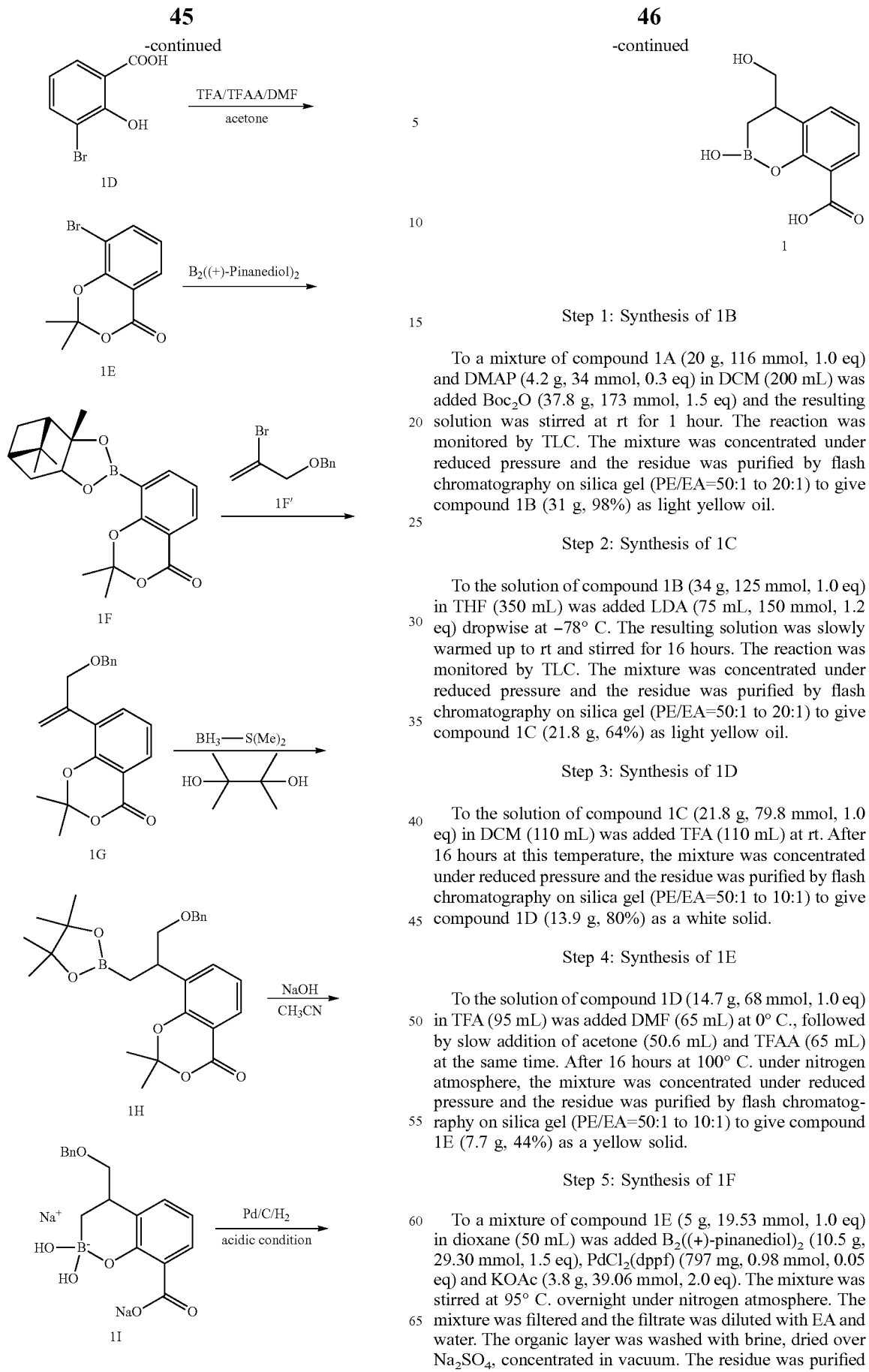

Step 1: Synthesis of 1B

To a mixture of compound 1A (20 g, 116 mmol, 1.0 eq) and DMAP (4.2 g, 34 mmol, 0.3 eq) in DCM (200 mL) was added Boc$_2$O (37.8 g, 173 mmol, 1.5 eq) and the resulting solution was stirred at rt for 1 hour. The reaction was monitored by TLC. The mixture was concentrated under reduced pressure and the residue was purified by flash chromatography on silica gel (PE/EA=50:1 to 20:1) to give compound 1B (31 g, 98%) as light yellow oil.

Step 2: Synthesis of 1C

To the solution of compound 1B (34 g, 125 mmol, 1.0 eq) in THF (350 mL) was added LDA (75 mL, 150 mmol, 1.2 eq) dropwise at −78° C. The resulting solution was slowly warmed up to rt and stirred for 16 hours. The reaction was monitored by TLC. The mixture was concentrated under reduced pressure and the residue was purified by flash chromatography on silica gel (PE/EA=50:1 to 20:1) to give compound 1C (21.8 g, 64%) as light yellow oil.

Step 3: Synthesis of 1D

To the solution of compound 1C (21.8 g, 79.8 mmol, 1.0 eq) in DCM (110 mL) was added TFA (110 mL) at rt. After 16 hours at this temperature, the mixture was concentrated under reduced pressure and the residue was purified by flash chromatography on silica gel (PE/EA=50:1 to 10:1) to give compound 1D (13.9 g, 80%) as a white solid.

Step 4: Synthesis of 1E

To the solution of compound 1D (14.7 g, 68 mmol, 1.0 eq) in TFA (95 mL) was added DMF (65 mL) at 0° C., followed by slow addition of acetone (50.6 mL) and TFAA (65 mL) at the same time. After 16 hours at 100° C. under nitrogen atmosphere, the mixture was concentrated under reduced pressure and the residue was purified by flash chromatography on silica gel (PE/EA=50:1 to 10:1) to give compound 1E (7.7 g, 44%) as a yellow solid.

Step 5: Synthesis of 1F

To a mixture of compound 1E (5 g, 19.53 mmol, 1.0 eq) in dioxane (50 mL) was added B$_2$((+)-pinanediol)$_2$ (10.5 g, 29.30 mmol, 1.5 eq), PdCl$_2$(dppf) (797 mg, 0.98 mmol, 0.05 eq) and KOAc (3.8 g, 39.06 mmol, 2.0 eq). The mixture was stirred at 95° C. overnight under nitrogen atmosphere. The mixture was filtered and the filtrate was diluted with EA and water. The organic layer was washed with brine, dried over Na$_2$SO$_4$, concentrated in vacuum. The residue was purified by column chromatography on silica gel (PE/EA=1:0 to 10:1) to give compound 1F (2.0 g, 29%).

Step 6: Synthesis of 1G

To a solution of compound 1F (1.0 g, 2.81 mmol, 1.0 eq) in THF (10 mL) was added 1F' (1.3 g, 5.62 mmol, 2.0 eq), Pd(PPh$_3$)$_4$ (162 mg, 0.14 mmol, 0.05 eq) and 2 N Na$_2$CO$_3$ (7.0 mL, 14.0 mmol, 5 eq). The mixture was stirred at 80° C. overnight under nitrogen atmosphere. Then the mixture was diluted with EA washed with water and brine, dried over Na$_2$SO$_4$, concentrated in vacuum. The residue was purified by column chromatography on silica gel (PE/EA=1:0 to 10:1) to give compound 1G (715 mg, 78%).

Step 7: Synthesis of 1H

To a solution of 2 M BH$_3$—S(Me)$_2$ (1.2 mL, 2.47 mmol, 2.0 eq) in dry THF (10 mL) at −15° C. under nitrogen atmosphere was added a solution of compound 1G (400 mg, 1.24 mmol, 1.0 eq) in dry THF (1 mL), slowly. The reaction mixture was stirred at rt for 2 h, quenched by water, and extracted with EA. The organic layer was washed with brine, dried over Na$_2$SO$_4$, and concentrated in vacuum. The residue was dissolved in dry THF (8 mL), and 2,3-Dimethylbutane-2,3-diol (292 mg, 2.47 mmol, 2.0 eq) was added. The reaction mixture was stirred at rt overnight. Then the reaction was filtered and the filtrate was concentrated. The residue was purified by column chromatography on silica gel (PE/EA=30:1 to 10:1) to give compound 1H (106 mg, 19%).

Step 8: Synthesis of 1I

To a solution of compound 1H (120 mg, 0.266 mmol, 1.0 eq) in H$_2$O/ACN (1 mL/1 mL) was added 0.5 M NaOH (1 mL, 0.5 mmol, 1.8 eq) and the resulting mixture stirred at rt for 3 h. Then the mixture was purified by prep-HPLC (under neutral conditions) to give compound 1I (50 mg, 60%).

Step 9: Synthesis of 1

To a solution of compound 1I (110 mg, 0.70 mmol, 1.0 eq) in MeOH (10 mL) was added Pd/C (11 mg, 10%, w/w). The resulting mixture was stirred at rt for 4 h under 1 atm of H$_2$. After filtration through a pad of Celite®, the filtrate was purified by prep-HPLC (under acidic conditions) to give compound 1 (20 mg, 26%).

LC-MS: 221 [M−H]$^-$ $^1$H NMR (400 MHz, CD$_3$OD) δ 7.75-7.70 (m, 1H), 7.46-7.35 (m, 1H), 6.87-6.81 (dd, J=7.6, 8.0 Hz, 1H), 4.09 (d, J=6.8 Hz, 1H), 3.76-3.72 (m, 1H), 3.59-3.57 (m, 1H), 1.20-1.18 (m, 2H)

Example 2

Disodium Salt of 4-(benzyloxymethyl)-2-hydroxy-7-methoxy-3,4-dihydro-1,2-benzoxaborinine-8-carboxylic Acid (Compound 2)

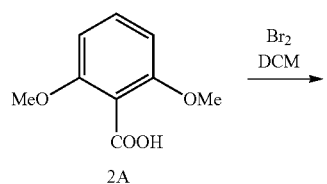

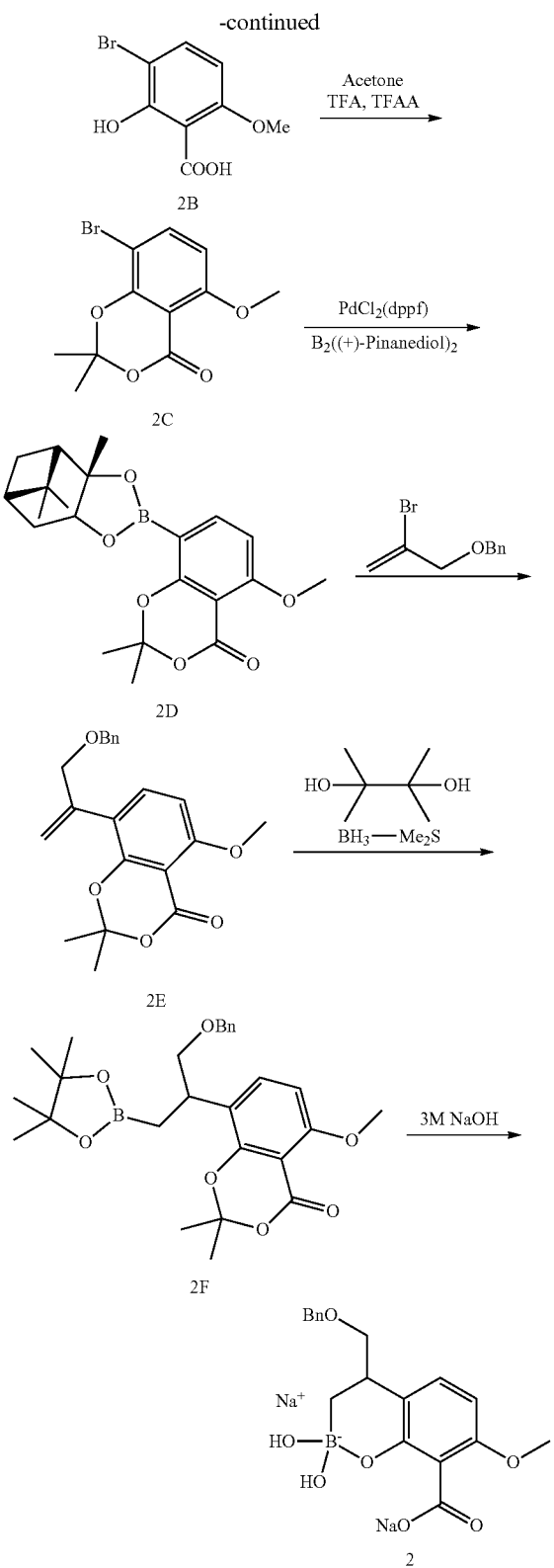

Step 1: Synthesis of 2B

A solution of bromine (14.06 mL, 274 mmol, 1 eq.) in CH$_2$Cl$_2$ (20 mL) was added slowly over 8 h to a suspension of 2,6-dimethoxybenzoic acid (2A) (50 g, 274 mmol) in CH₂Cl₂ (200 mL). After stirring at rt overnight, the light orange slurry was heated and a portion of the solvent (methyl bromide, hydrogen bromide and CH₂Cl₂) was removed by distillation at atmospheric pressure (total volume distilled 100 mL). Ethanol (150 mL) was added and the remaining CH₂Cl₂ was distilled off at atmospheric pressure, slowly increasing the bath temperature to 90° C. Upon completion of the distillation (1 h), the heterogeneous mixture was cooled to rt. After stirring 1 h at rt, the slurry was cooled to 0° C. After stirring at 0° C. for 2 h, the solids were collected by filtration. The filtrate was recirculated to rinse the flask and stir bar. The solids were rinsed with ethanol at 0° C. (2×50 mL), air dried, then dried under high vacuum to give compound 2B as fine white needles (58.23 g, 85.9%).

Step 2: Synthesis of 2C

A 10-mL syringe filled with trifluoroacetic anhydride (11.25 mL, 81 mmol, 2 eq) and a 20-mL syringe filled with acetone (17 mL, 232 mmol, 5.7 eq) simultaneously dispensed their contents via syringe pump over 24 hours into a clear solution of 2B (10 g, 40 mmol) in TFA (10 mL) at 70° C. After 1 hour, the starting material began to crystallize out. TFA (5 mL) was added, affording a clear solution. After another hour at 70° C. the solution became slightly heterogeneous. Upon completion of the addition, HPLC showed 89:11 product to starting material. After stirring at 70° C. overnight, the ratio was 92:8. The reaction mixture was cooled to rt, diluted with ethyl acetate (15 mL), filtered over Celite®, and the pad and flask were rinsed with ethyl acetate (2×10 mL). The clear black filtrate was concentrated to dryness. The solids were taken up in ethyl acetate (50 mL) and CH₂Cl₂ (10 mL, to improve solubility of the product) and washed twice with a saturated solution of NaHCO₃ (50 and 30 mL). The brown/black solution was concentrated to dryness. The residue was taken up in ethyl acetate (10 mL) and the mixture was heated to reflux. Heptane (3×10 mL) was added and the mixture was brought to reflux (after the last addition of heptane, the product started crystallizing). The heterogeneous mixture was refluxed for 15 min and was allowed to cool to rt. After stirring at rt for 2 hours and 0° C. for 2 hours, the solids were collected by filtration. The filtrate was recirculated to rinse the flask. The solids were rinsed with 3:1 heptane/ethyl acetate at 0° C. (2×10 mL), air dried, then dried under high vacuum to give compound 2C as a light tan powder (8.83 g, 76%).

Step 3: Synthesis of 2D

To a mixture of compound 2C (10.0 g, 3.5 mmol, 1.0 eq) in dioxane (300 mL) was added B₂((+)-pinanediol)₂ (18.8 g, 52.5 mmol, 1.5 eq), PdCl₂(dppf) (2.8 g, 3.5 mmol, 0.1 eq) and KOAc (6.86 g, 70 mmol, 2.0 eq). The mixture was stirred at 96° C. overnight under nitrogen atmosphere. Then the mixture was filtered and the filtrate was and diluted with EA, washed with water and brine, dried over Na₂SO₄, and concentrated in vacuum. The residue was purified by column chromatography on silica gel (PE/EA=30:1 to 5:1) and triturated with PE/EA (10:1) to give compound 2D (7.9 g, 58%).

Step 4: Synthesis of 2E

To a mixture of compound 2D (7.3 g, 19.06 mmol, 1.0 eq) in THF (120 mL) was added bromide 1F' (5.6 g, 24.8 mmol, 1.3 eq), Pd(PPh₃)₄ (1.1 g, 0.95 mmol, 0.05 eq) and 2 N Na₂CO₃ (48 mL, 95 mmol, 5.0 eq). The mixture was stirred at 80° C. for 12 h under nitrogen atmosphere. The mixture was filtered and the filtrate was and extracted with EA and H₂O, and the organic layer was separated and washed with brine, dried over Na₂SO₄, and concentrated in vacuum. The residue was purified by column chromatography on silica gel (PE/EA=20:1 to 5:1) to give compound 2E (9.0 g, 100%, contained some pinanediol).

Step 5: Synthesis of 2F

To a solution of 2 M BH₃—S(Me)₂ (32 mL, 63.56 mmol, 1.5 eq) in dry THF (300 mL) at −15° C. under nitrogen atmosphere was added a solution of compound 2E (15 g, 42.37 mmol, 1.0 eq) in dry THF (50 mL) slowly. The mixture was then moved away from the ice-bath and stirred for 2 h at rt. The mixture was quenched with water and extracted with EA. The organic layer was washed with brine, dried over Na₂SO₄, and concentrated in vacuum. The residue was dissolved in dry THF (150 mL), pinacol (7.5 g, 63.56 mmol, 1.5 eq) was added, and the resulting mixture stirred at rt overnight. The reaction was filtered and the filtrate was concentrated. The residue was purified by column chromatography on silica gel (PE/EA=30:0 to 5:1) to give compound 2F (8 g, 39%).

Step 6: Synthesis of 2

To a solution of compound 2F (8 g, 16.59 mmol, 1.0 eq) in H₂O/ACN (7 mL/15 mL) was added 3 M NaOH (11.1 mL, 33.3 mmol, 2 eq), and the mixture was stirred at rt for 20 h. The mixture was purified by prep-HPLC to give compound 2 (6 g, 100%).

LC-MS: 343 [M+H]⁺

¹H NMR (400 MHz, CD₃OD): δ 7.41-7.18 (m, 5H), 7.04-6.93 (m, 1H), 6.29-6.16 (m, 1H), 4.51 (m, 2H), 3.75-3.68 (m, 3H), 3.67-3.59 (m, 2H), 2.98-2.85 (m, 1H), 0.61-0.50 (m, 1H), 0.41-0.29 (m, 1H).

Example 3

2-Hydroxy-4-(hydroxymethyl)-7-methoxy-3,4-dihydro-1,2-benzoxaborinine-8-carboxylic Acid (Compound 3)

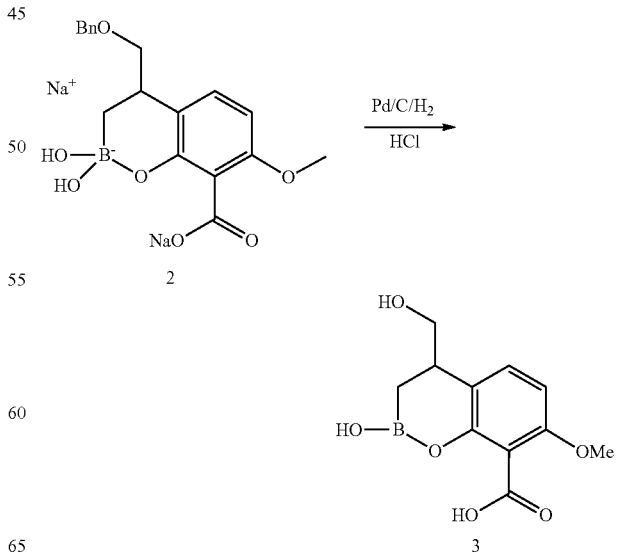

To a solution of compound 2 (2.0 g, 5.85 mmol, 1.0 eq) in methanol (20 mL) was added 1 N HCl (to adjust the solution to pH 5-6) and Pd/C (200 mg, 10% W/W). The mixture was stirred under $H_2$ at rt for 16 h, filtered through Celite® and purified by prep-HPLC (under acidic conditions) to give compound 3 (310 mg, 21%).

LC-MS: 253 [M+H]$^+$ $^1$H NMR (400 MHz, CD$_3$OD) δ 7.21-7.20 (m, 1H), 6.67-6.65 (d, J=8.4 Hz, 1H), 3.84 (s, 3H), 3.58-3.57 (m, 2H), 3.02-2.85 (m, 1H), 1.15-1.13 (m, 2H).

Example 4

(4R)-2-hydroxy-4-(hydroxymethyl)-7-methoxy-3,4-dihydro-1,2-benzoxaborinine-8-carboxylic Acid and (4S)-2-hydroxy-4-(hydroxymethyl)-7-methoxy-3,4-dihydro-1,2-benzoxaborinine-8-carboxylic Acid (Compounds 4 and 5)

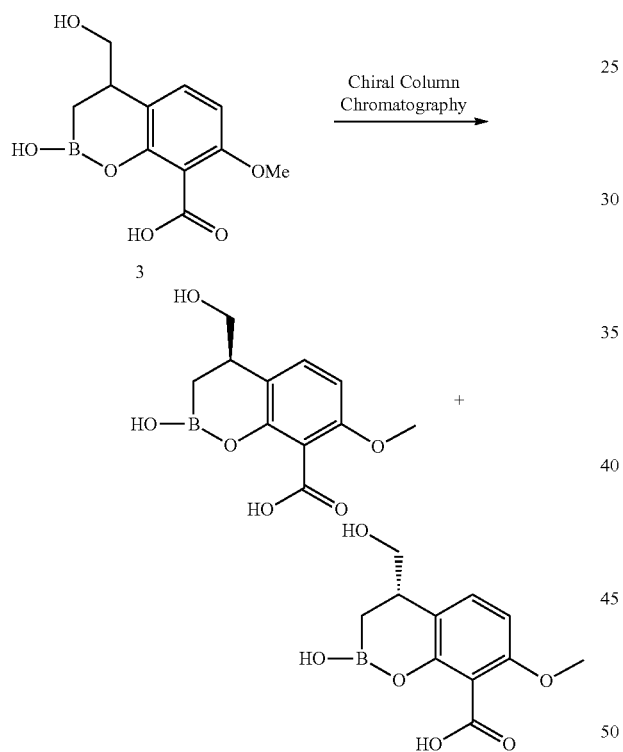

2-Hydroxy-4-(hydroxymethyl)-7-methoxy-3,4-dihydro-1,2-benzoxaborinine-8-carboxylic acid (Compound 3) (1.03 g) was separated by chiral column (Superchiral S-AD, Hexane/EtOH/MeOH/formic acid=60/13/27/0.01, v/v/v/v) to give Compound 4 344 mg, 33% and Compound 5, 410 mg, 39%. Compound 4 and Compound 5 are depicted as the stereoisomers in the scheme above, although absolute stereochemistry of the individual isomers is yet to be determined.

Compound 4:

LC-MS: 251 [M–H]$^-$ $^1$H NMR (400 MHz, CD$_3$OD) δ 7.21-7.20 (m, 1H), 6.67-6.65 (d, J=8.4 Hz, 1H), 3.84 (s, 3H), 3.58-3.57 (m, 2H), 3.02-2.85 (m, 1H), 1.15-1.13 (m, 2H).

Compound 5:

LC-MS: 251 [M–H]$^-$ $^1$H NMR (400 MHz, CD$_3$OD) δ 7.21-7.20 (m, 1H), 6.67-6.65 (d, J=8.4 Hz, 1H), 3.84 (s, 3H), 3.58-3.57 (m, 2H), 3.02-2.85 (m, 1H), 1.15-1.13 (m, 2H).

Example 5

7-fluoro-2-hydroxy-4-(hydroxymethyl)-3,4-dihydro-1,2-benzoxaborinine-8-carboxylic Acid (Compound 6)

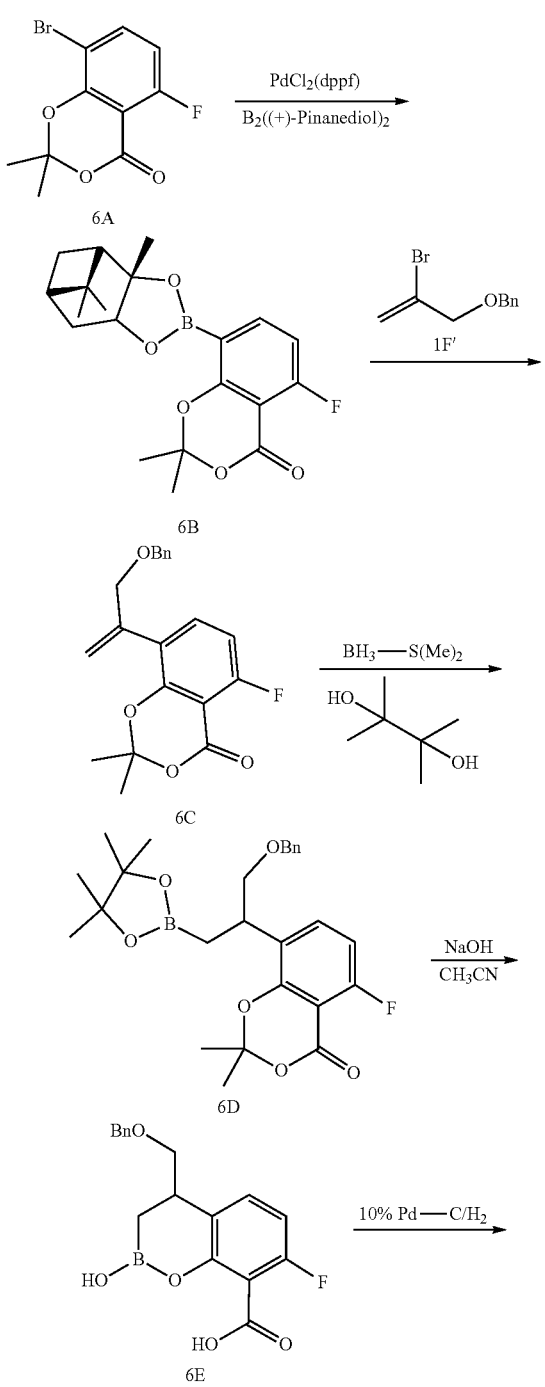

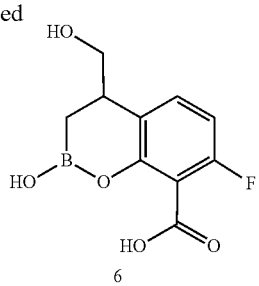

6

Step 1: Synthesis of Compound 6A

Compound 6A was prepared from a Boc-t-Butyl ester intermediate (previously disclosed in WO 2015/179308) by TFA deprotection (as described in step 3 of Example 1) followed by isopropylidene protection (as described in step 2 of Example 2).

Step 2: Synthesis of Compound 6B

To a mixture of bromide compound 6A (20.0 g, 72.99 mmol, 1.0 eq) in dioxane (200 mL) was added $B_2((+)$-Pinanediol$)_2$ (39.2 g, 109.5 mmol, 1.5 eq), $PdCl_2(dppf)$ (3.0 g, 3.65 mmol, 0.05 eq) and KOAc (14.3 g, 145.9 mmol, 2.0 eq). The mixture was stirred at 95° C. overnight under nitrogen atmosphere. The mixture was filtered and the filtrate diluted with EtOAc and washed with water, brine, dried over $Na_2SO_4$, and concentrated in vacuum. The residue was purified by column chromatography on silica gel (PE/EA=1:0 to 10:1) to give compound 6B (13.5 g, 49%).

Step 3: Synthesis of Compound 6C

To a mixture of compound 6B (13.5 g, 36.1 mmol, 1.0 eq) in THF (90 mL) was added 1F' (12.2 g, 54.14 mmol, 1.5 eq), $Pd(PPh_3)_4$ (2.1 g, 1.80 mmol, 0.05 eq) and 2 N $Na_2CO_3$ (90 mL, 180.5 mmol, 5.0 eq). The mixture was stirred at 80° C. overnight under nitrogen atmosphere. Then the mixture was filtered through a pad of Celite®, and water was added. The mixture was extracted with EA. The combined organic layers were washed with water, brine, dried over $Na_2SO_4$, and concentrated in vacuum. The residue was purified by column chromatography on silica gel (PE/EA=50:1 to 10:1) to give compound 6C (9.8 g, 79%).

Step 4: Synthesis of Compound 6D

To a solution of 2 M $BH_3$—$S(Me)_2$ (1.5 mL, 2.92 mmol, 2.0 eq) in dry THF (10 mL) at −15° C. under nitrogen atmosphere was added a solution of compound 6C (500 mg, 1.462 mmol, 1.0 eq) in dry THF (2 mL) slowly. The reaction mixture was stirred at rt for 2 h, quenched with water, and extracted with EA. The organic layer was washed with brine, dried over $Na_2SO_4$, and concentrated in vacuum. The residue was dissolved in dry THF (8 mL). To the resulting mixture was added 2,3-dimethylbutane-2,3-diol (345 mg, 2.92 mmol, 2.0 eq). The reaction was stirred at rt overnight. Then the reaction was filtered and the filtrate was concentrated. The residue was purified by column chromatography on silica gel (PE/EA=30:0 to 10:1) to give compound 6D (188 mg, 27%).

Step 5: Synthesis of Compound 6E

To a solution of compound 6D (188 mg, 0.4 mmol, 1.0 eq) in $H_2O/ACN$ (1 mL/1 mL) was added 3 M NaOH (0.26 mL, 0.8 mmol, 2.0 eq) and the resulting mixture was stirred at rt overnight. The crude product 6E was used for next step directly.

Step 6: Synthesis of Compound 6

To the crude of 6E was added Pd/C (18 mg, 10% w/w). The mixture was stirred at rt overnight under $H_2$. After filtration, the mixture was purified by prep-HPLC (under neutral conditions) to give 8 mg of compound 6.

LC-MS: 282 [M+MeCN+H]$^+$; 239 [M−H]$^-$ $^1$H NMR (400 MHz, $CD_3OD$) δ 7.03 (m, 1H), 6.40-6.38 (m, 1H), 3.87-3.83 (m, 1H), 3.71-3.68 (m, 1H), 3.04-3.03 (m, 1H), 0.71 (m, 2H)

Example 6

(4R)-7-fluoro-2-hydroxy-4-(hydroxymethyl)-3,4-dihydro-1,2-benzoxaborinine-8-carboxylic Acid and (4S)-7-fluoro-2-hydroxy-4-(hydroxymethyl)-3,4-dihydro-1,2-benzoxaborinine-8-carboxylic Acid (Compounds 7 and 8)

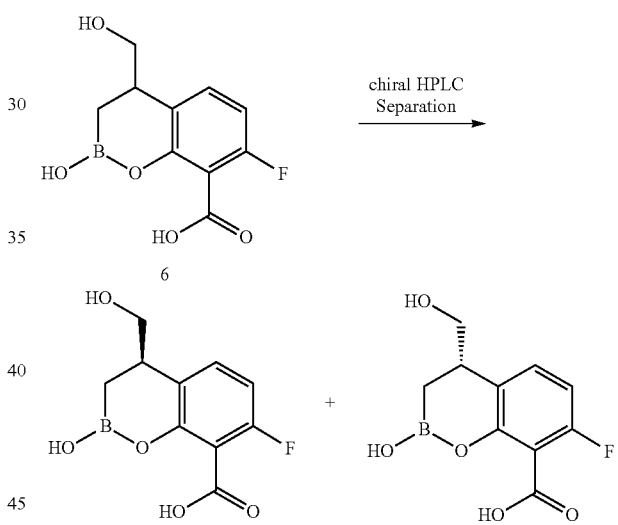

7-Fluoro-2-hydroxy-4-(hydroxymethyl)-3,4-dihydro-1,2-benzoxaborinine-8-carboxylic acid (Compound 6) was separated by HPLC with a chiral column (Superchiral S-AD, Hexane/EtOH/MeOH/TFA=90/3.3/6.7/0.05 (v/v/v)) to give Compound 7 (40.8 mg, 16%) and Compound 8 (33.0 mg, 13%). Compound 7 and Compound 8 are depicted as the stereoisomers in the scheme above, although absolute stereochemistry of the individual isomers is yet to be determined.

Compound 7:

LC-MS: 239 [M−H]$^-$ $^1$H NMR (400 MHz, $CD_3OD$) δ 7.32-7.29 (m, 1H), 6.71-6.67 (m, 1H), 3.97-3.79 (m, 1H), 3.76-3.54 (m, 2H), 1.18-1.13 (m, 2H).

Compound 8:

LC-MS: 239[M−H]$^-$ $^1$H NMR (400 MHz, $CD_3OD$) δ 7.32-7.29 (m, 1H), 6.71-6.67 (m, 1H), 3.97-3.79 (m, 1H), 3.76-3.54 (m, 2H), 1.18-1.13 (m, 2H).

Example 7

2-Hydroxy-4-(hydroxymethyl)-3,4-dihydrooxaborinino[6,5-c]pyridine-8-carboxylic Acid (Compound 9)

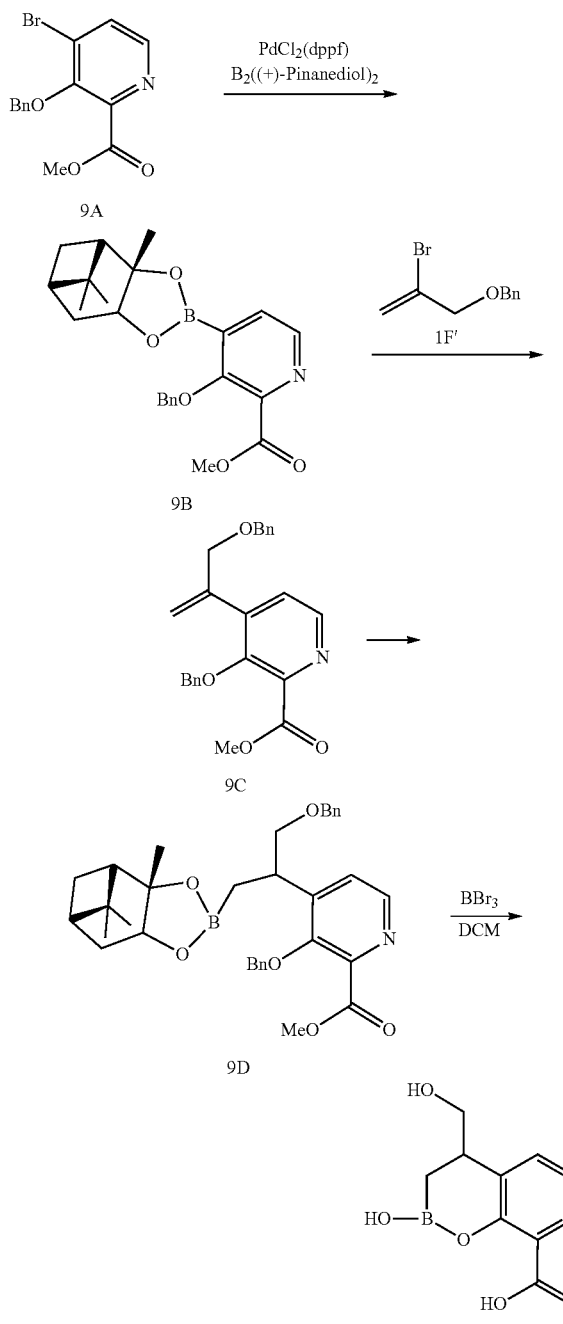

Step 1: Synthesis of Compound 9B

To a mixture of compound 9A (Tetrahedron, 2011, 67, 8757-8762) (1.0 g, 3.12 mmol, 1.0 eq) in dioxane (10 mL) was added $B_2((+)\text{-pinanediol})_2$ (1.67 g, 4.67 mmol, 1.5 eq), $PdCl_2(dppf)$ (255 mg, 0.31 mmol, 0.1 eq) and KOAc (916 mg, 9.35 mmol, 3.0 eq). The mixture was stirred at 55° C. overnight under nitrogen atmosphere. The mixture was filtered and the filtrate was extracted with EA and $H_2O$, and the organic layer was separated, washed with brine, dried over $Na_2SO_4$, and concentrated in vacuum. The residue was purified by column chromatography on silica gel (PE/EA/DCM=30:1:0 to 5:1:1) to give compound 9B (1.1 g, 84%).

Step 2: Synthesis of Compound 9C

To a mixture of compound 9B (1.1 g, 2.61 mmol, 1.0 eq) in THF (90 mL) was added 1F' (1.18 g, 5.22 mmol, 2.0 eq), $Pd(PPh_3)_4$ (151 mg, 0.13 mmol, 0.05 eq), and 2 N $Na_2CO_3$ (6.5 mL, 13.0 mmol, 5 eq). The mixture was stirred at 80° C. overnight under nitrogen atmosphere. Then the mixture was filtered and the filtrate was washed with ethyl acetate. The organic layer was washed with water and brine, dried over $Na_2SO_4$, and concentrated in vacuum. The crude product was purified by column chromatography on silica gel (PE/EA=20:1 to 5:1) to give compound 9C (978 mg, 96%).

Step 3: Synthesis of Compound 9D

To a mixture of compound 9C (350 mg, 0.90 mmol, 1.0 eq) in methanol (2 mL) was added $B_2((+)\text{-pinanediol})_2$ (370 mg, 1.03 mmol, 1.15 eq), $Cu_2O$ (10 mg, 0.072 mmol, 0.08 eq), $PPh_3$ (26 mg, 0.099 mmol, 0.11 eq), and $KH_2PO_4$ (188 mg, 1.079 mmol, 1.2 eq). The mixture was stirred at 40° C. for 2.5 h under nitrogen atmosphere. Then the mixture was filtered and the filtrate was washed with EA, and the organic layer was washed with brine, dried over $Na_2SO_4$, and concentrated in vacuum. The residue was purified by column chromatography on silica gel (PE/EA=20:1 to 2:1) to give compound 9D (350 mg, 68%).

Step 4: Synthesis of Compound 9

To a solution of compound 9D (197 mg, 0.411 mmol, 1.0 eq) in DCM (1.5 mL) was added 1 M $BBr_3$ (1.3 mL, 1.30 mmol, 5 eq), the mixture was stirred at rt for 1 h, and then the mixture was purified by prep-HPLC (under acidic conditions) to give compound 9 (5.5 mg).

LC-MS: 224 $[M+H]^+$

1H NMR (400 MHz, $D_2O$) δ 8.20-8.19 (d, J=5.6 Hz, 1H), 7.90-7.89 (d, J=5.6 Hz, 1H), 3.91-3.89 (m, 1H), 3.85-3.81 (m, 1H), 3.73-3.70 (m, 1H), 1.25-1.20 (m, 2H).

Example 8

Disodium Salt 4-(benzyloxymethyl)-2-hydroxy-3,4-dihydrooxaborinino[6,5-c]pyridine-8-carboxylic Acid (Compound 10)

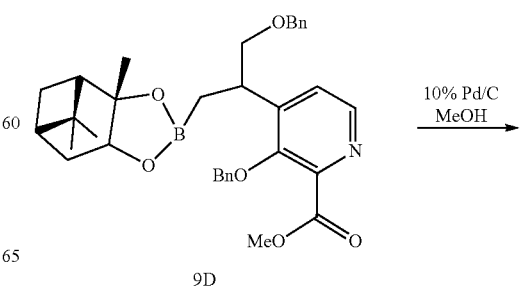

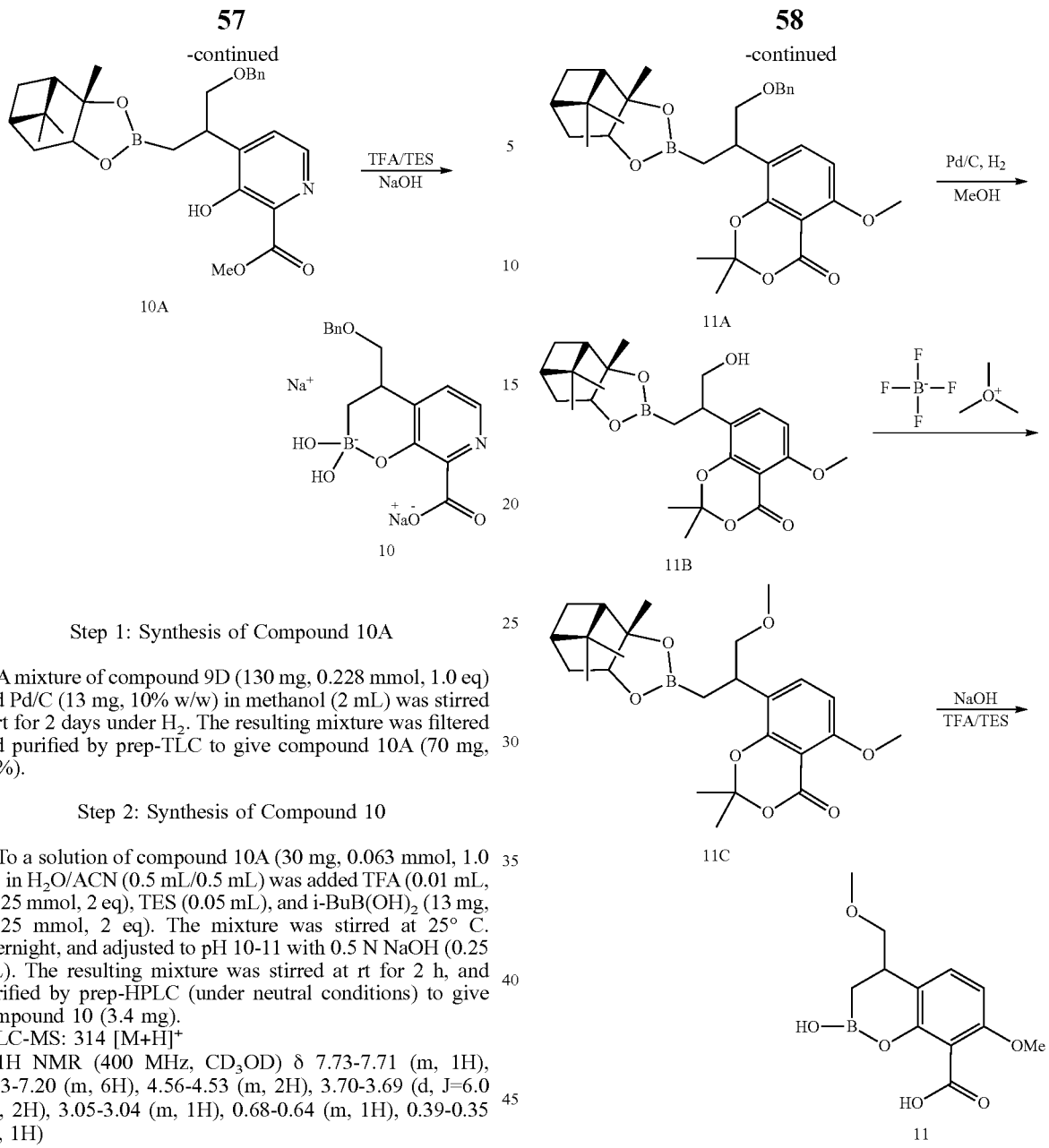

Step 1: Synthesis of Compound 10A

A mixture of compound 9D (130 mg, 0.228 mmol, 1.0 eq) and Pd/C (13 mg, 10% w/w) in methanol (2 mL) was stirred at rt for 2 days under $H_2$. The resulting mixture was filtered and purified by prep-TLC to give compound 10A (70 mg, 64%).

Step 2: Synthesis of Compound 10

To a solution of compound 10A (30 mg, 0.063 mmol, 1.0 eq) in $H_2O$/ACN (0.5 mL/0.5 mL) was added TFA (0.01 mL, 0.125 mmol, 2 eq), TES (0.05 mL), and i-BuB(OH)$_2$ (13 mg, 0.125 mmol, 2 eq). The mixture was stirred at 25° C. overnight, and adjusted to pH 10-11 with 0.5 N NaOH (0.25 mL). The resulting mixture was stirred at rt for 2 h, and purified by prep-HPLC (under neutral conditions) to give compound 10 (3.4 mg).

LC-MS: 314 [M+H]$^+$

1H NMR (400 MHz, CD$_3$OD) δ 7.73-7.71 (m, 1H), 7.33-7.20 (m, 6H), 4.56-4.53 (m, 2H), 3.70-3.69 (d, J=6.0 Hz, 2H), 3.05-3.04 (m, 1H), 0.68-0.64 (m, 1H), 0.39-0.35 (m, 1H)

Example 9

2-Hydroxy-7-methoxy-4-(methoxymethyl)-3,4-dihydro-1,2-benzoxaborinine-8-carboxylic Acid (Compound 11)

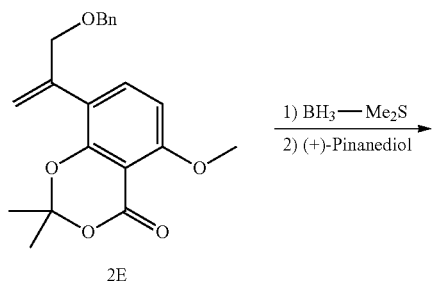

Step 1: Synthesis of Compound 11A

To a solution of BH$_3$—S(Me)$_2$ (28.2 mL, 56.4 mmol, 2.0 eq) in dry THF (60 mL) at −15° C. was added compound 2E (10 g, 28.2 mmol, 1 eq). The mixture was warmed to rt and stirred for 3.5 h. TLC showed no compound 2E left. The mixture was diluted with water (30 mL) and extracted with EA (2×60 mL). The organic phase was dried over Na$_2$SO$_4$ and concentrated to give a residue, which was used for next step without further purification.

The residue prepared above was dissolved with dry THF (60 mL). (+)-Pinanediol (9.6 g, 56.4 mmol, 2.0 eq) was added into the solution. The mixture was stirred overnight at rt, and concentrated. The residue was purified by flash column chromatography (PE/EA=5:1) to give compound 11A (11 g, impure).

Step 2: Synthesis of Compound 11B

To a solution of crude compound 11A (5.3 g) in methanol (53 mL) was added 10% Pd/C (530 mg, 10% w/w) at rt. The mixture was stirred under hydrogen atmosphere (balloon) overnight. The resulting mixture was filtered and the filtrate was concentrated. The residue was purified by flash column chromatography (PE/EA=2:1) to give compound 11B (1.2 g, 20%, 2 steps).

Step 3: Synthesis of Compound 11C

To a mixture of compound 11B (250 mg, 0.56 mmol, 1.0 eq) in dry DCM (5 mL) was added trimethyloxonium tetrafluoroborate (167 mg, 1.13 mmol, 2.0 eq) and $Cs_2CO_3$ (183.5 mg, 0.563 mmol, 1.0 eq). The mixture was stirred at 25° C. overnight under nitrogen atmosphere. The resulting mixture was diluted with water and extracted with DCM. The DCM layer was washed with brine, dried over sodium sulfate, and concentrated in vacuo. The crude residue was purified by column chromatography on silica gel to give compound 11C (161 mg, 62%).

Step 2: Synthesis of Compound 11

To a solution of compound 11C (155 mg, 0.34 mmol, 1.0 eq) in $H_2O$/ACN (1.5 mL/1.5 mL) was added 3 N NaOH (0.34 mL, 1.02 mmol, 3 eq). The mixture was stirred at 25° C. overnight. To the mixture were added TFA (0.06 mL), TES (0.06 mL) and i-BuB(OH)$_2$ (68 mg, 0.68 mmol, 2 eq).

The resulting mixture was stirred at 25° C. for 1 h, and purified by prep-HPLC (under acidic conditions) to give compound 11 (57 mg, 63%).

LC-MS: 267 [M+H]$^+$ $^1$H NMR (400 MHz, CD$_3$OD) δ 7.19 (d, J=8.0 Hz, 1H), 6.67 (d, J=8.8 Hz, 1H), 3.82 (s, 3H), 3.42-3.30 (m, 2H), 3.25 (s, 3H), 3.07-3.05 (m, 1H), 1.15-1.05 (m, 2H).

Example 10

2-Hydroxy-4-(2-hydroxyethyl)-7-methoxy-3,4-dihydro-1,2-benzoxaborinine-8-carboxylic Acid Compound 12)

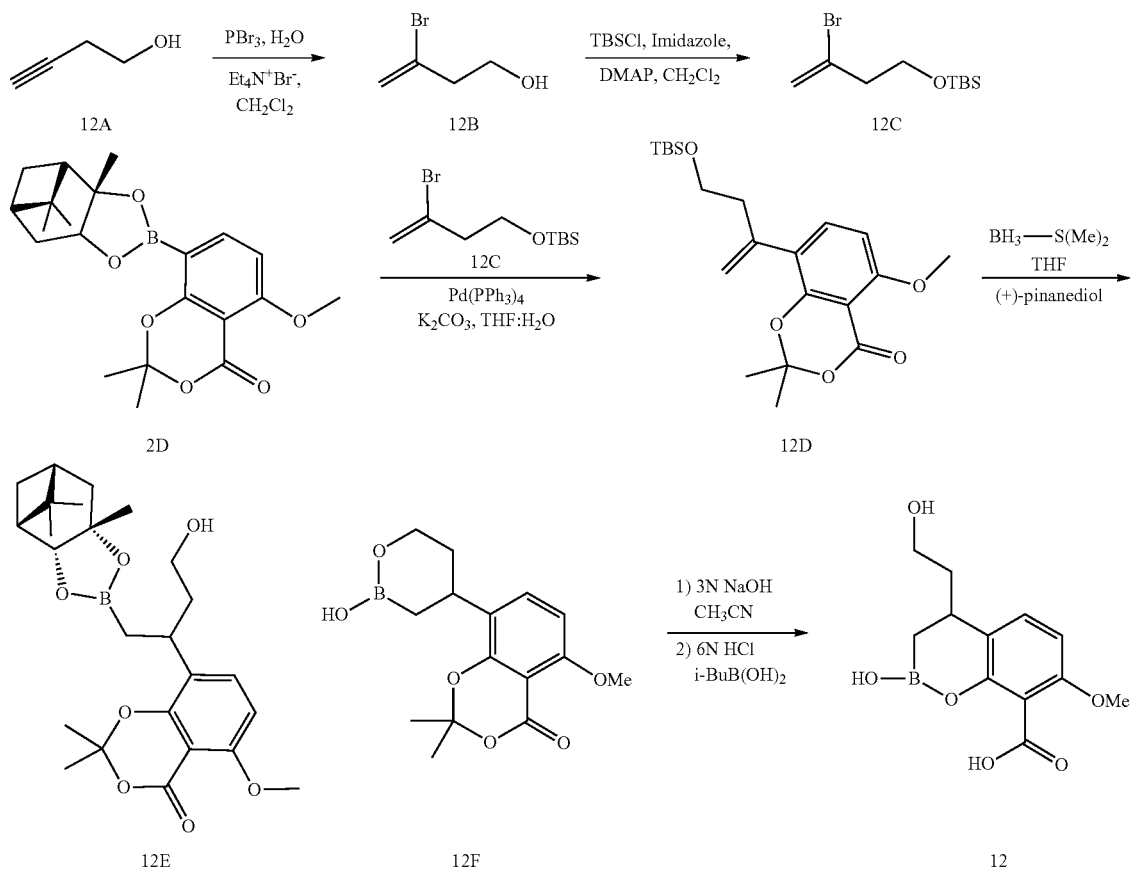

Step 1: Synthesis of Compound 12B

Gaseous HBr was produced by adding PBr$_3$ (10.5 mL, 110 mmol) dropwise to water (6.0 mL, 330 mmol) at room temperature. The HBr gas produced was bubbled into a solution of Et$_4$N+Br$^-$ (97.0 g, 0.3 mol, 1.2 eq) in DCM (300 mL) at 0° C. To the HBr solution was added 3-butyn-1-ol (12A, 19.0 mL, 0.25 mol, 1.0 eq) and the solution was heated at 40° C. for 5 hrs. Removal of the solvent, followed by distillation, afforded 3-bromo-3-buten-1-ol, 12B (27.9 g, 73%).

Step 2: Synthesis of Compound 12C

To a solution of 3-bromo-3-buten-1-ol (12B) (13.0 g, 86.1 mmol, 1.0 eq) in DCM (250 mL) at room temperature was added imidazole (7.74 g, 114 mmol, 1.3 eq), DMAP (2.15 g, 18.0 mmol, 0.2 eq), and TBSCl (14.5 g, 96.2 mmol, 1.1 eq). The reaction was stirred at room temperature for 3 hrs, filtered, washed with brine, dried over MgSO$_4$, concentrated, and purified via FCC (SiO$_2$, hexanes) to afford compound 12C (16.8 g, 73%).

Step 3: Synthesis of Compound 12D

To a solution of 2D (503 mg, 1.30 mmol, 1.0 eq) in THF (3.6 mL) was added alkene 12C (688 mg, 2.60 mmol, 2.0 eq), followed by a 2 M solution of K$_2$CO$_3$ (1.6 mL, 3.2 mmol, 2.5 eq). After bubbling the solution with N$_2$ for 10 min, Pd(PPh$_3$)$_4$ (147 mg, 0.13 mmol, 0.1 eq) was added and the reaction mixture was heated to 70° C. for 16 hrs. The reaction was quenched with NaHCO$_3$ (saturated aq), extracted with EtOAc (2×), dried over Na$_2$SO$_4$, concentrated, and purified via FCC (SiO$_2$, 10% EtOAc/hexanes) to afford compound 12D (360 mg, 70%) as an orange oil.

Step 4: Synthesis of Compounds 12E and 12F

To a solution of 12D (274 mg, 0.70 mmol, 1.0 eq) in THF (14 mL) was added BH$_3$—S(Me)$_2$ (1.2 eq, 0.42 mL, 2M in THF, 0.84 mmol, 1.2 eq) at 0° C. The reaction was allowed to warm up to room temperature slowly and stirred for 2 hrs. (+)-Pinanediol (291 mg, 1.7 mmol, 2.4 eq) was added and the reaction was stirred at room temperature overnight. The reaction mixture was quenched with H$_2$O, extracted with EtOAc (3×), dried over Na$_2$SO$_4$, and concentrated. The residue was purified with FCC (SiO$_2$, 40% EtOAc/hexanes), affording a mixture of 12E and 12F (109 mg), which were used for next step without further purification.

Step 5: Synthesis of Compound 12

The mixture of compounds 12E and 12F (109 mg) was dissolved in acetonitrile (3.0 mL), and a 3 M solution of NaOH (1.2 mL) was added at room temperature. The reaction mixture was allowed to stir for 24 hrs. The resulting solution was adjusted to pH 2-3 using 6 N HCl. i-Bu(OH)$_2$ (53 mg) was added. The reaction was stirred overnight, and purified by prep-HPLC to afford compound 12 (7.5 mg, 4%) as white fluffy solid.

LC-MS: 267.2 [M+1]$^+$

1H NMR (300 MHz, CD$_3$OD) δ 7.28 (d, 1H), 6.80 (d, 1H), 4.05 (m, 2H), 3.92 (s, 3H), 3.30-3.18 (m, 1H), 1.90-1.68 (m, 2H), 1.20 (dd, 1H), 0.90 (dd, 1H).

Example 11

2-Hydroxy-4-(hydroxymethyl)-7-methoxy-3,4-dihydro-1,2-benzoxaborinine-8-carboxylic Acid (Compound 3)

Compound 3 (described in Example 3) was also prepared using the following alternative synthetic sequence.

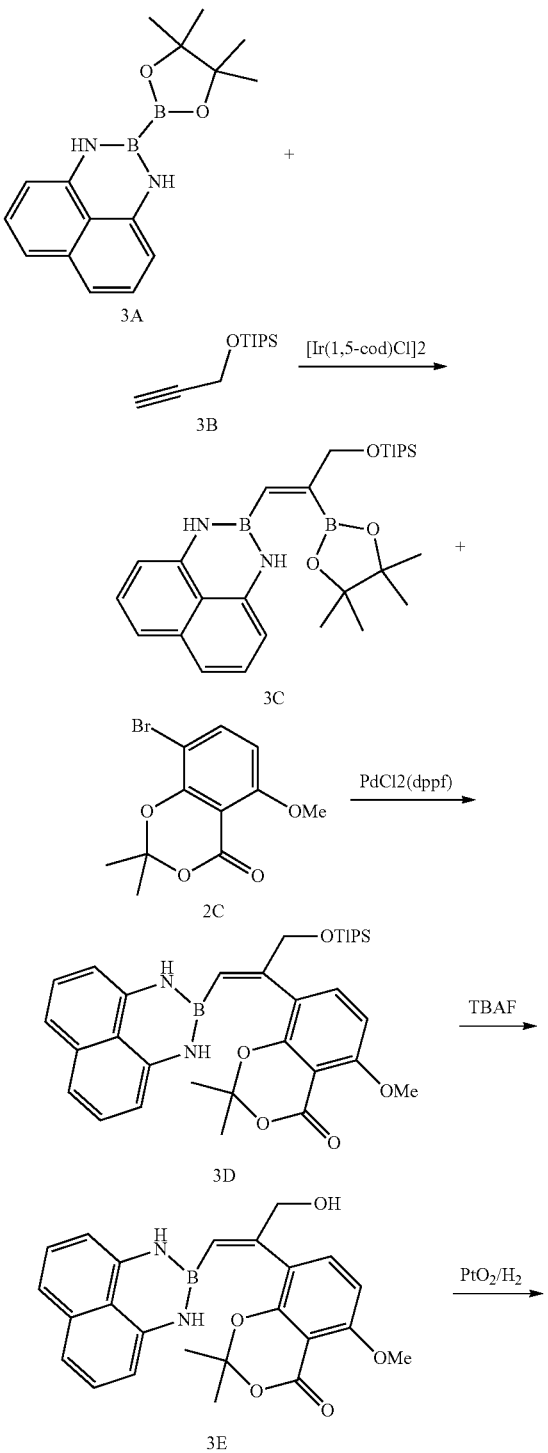

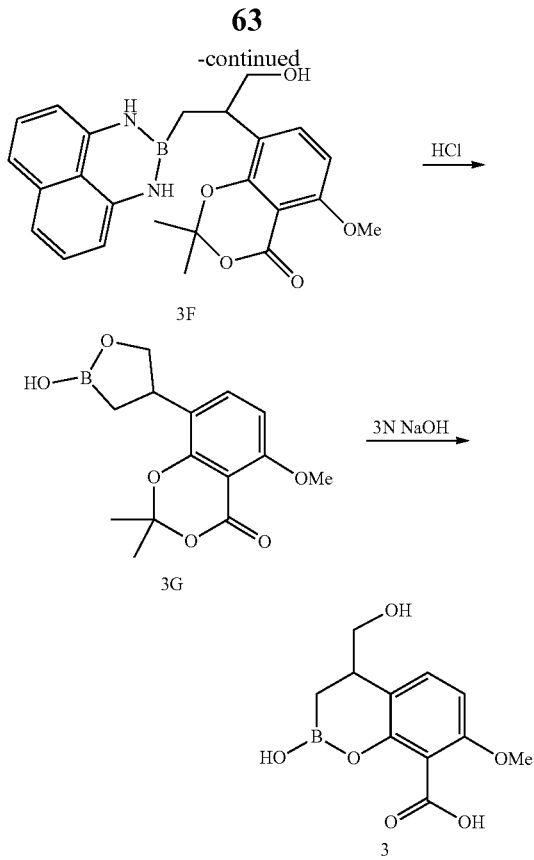

Step 1: Synthesis of Compound 3C

A solution of compound 3A (*J. Org. Chem.*, 2016, 81, 4269-4279) (26 g, 0.123 mol, 1.5 eq), triisopropylsilyl propargyl ether (3B) (24 g, 0.082 mol, 1.0 eq), and Bis(1,5-cyclooctadiene)diiridium(I) dichloride (0.826 g, 1.23 mmol, 0.015 eq) in toluene (260 mL) was heated to 80° C. and stirred overnight under $N_2$. The resulting mixture was cooled to rt and filtered. The filtrate was concentrated and the residue was purified by flash column chromatography (PE/EA=5:1) to give compound 3C (35.7 g, 86%).

Step 2: Synthesis of Compound 3D

To a solution of compound 3C (5.0 g, 9.881 mmol, 1.1 eq) in THF (50 mL) was added compound 2C (2.57 g, 8.983 mmol, 1.0 eq), $PdCl_2$(dppf) (368 mg, 0.494 mmol, 0.05 eq), water (1.625 g, 98.81 mmol, 10 eq), and $K_3PO_4 \cdot 3H_2O$ (7.175 g, 29.644 mmol, 3.0 eq). The mixture was stirred at 80° C. overnight under nitrogen atmosphere. The mixture was filtered and the filtrate was diluted with EA and $H_2O$. The layers were separated and the organic layer was washed with brine, dried over $Na_2SO_4$, and concentrated in vacuum. The residue was purified by column chromatography on silica gel to give compound 3D (4.79 g, 82%).

Step 3: Synthesis of Compound 3E

To a solution of compound 3D (34 g, 58.0 mmol, 1.0 eq) in THF (300 mL) at rt was added TBAF (18.1 g, 69.6 mmol, 1.2 eq). The mixture was stirred for 3 h at rt and TLC showed no compound 3D left. The resulting mixture was diluted with water (150 mL) and extracted with EA (2×300 mL). The organic phase was dried over $Na_2SO_4$ and concentrated. The residue was purified with flash column chromatography (PE/EA=1:1) to give compound 3E (16.1 g, 81%).

Step 4: Synthesis of Compound 3F

To a solution of compound 3E (16 g, 37.21 mmol) in methanol (160 mL) was added $PtO_2$ (1.6 g, 10% w/w) under $N_2$, then replaced with hydrogen. The mixture was stirred at rt for 6 h. The resulting mixture was filtered and the filtrate was concentrated. The residue was purified by silica gel column chromatography (PE/EA=1:1) to give compound 3F (13.6 g, 87%).

Step 5: Synthesis of Compound 3G

To a solution of compound 3F (13.4 g, 31.02 mmol, 1.0 eq) in THF (150 mL) at rt was added 3 N aq. HCl (51.7 mL, 155.1 mmol, 5.0 eq). The mixture was stirred overnight and LC-MS showed 10% compound 3F remained. Then additional 3 N HCl (20.7 mL, 61.02 mmol, 2.0 eq) was added. The mixture was stirred at rt for 3 h, at which point LC-MS showed complete consumption of the starting material. Water (75 mL) was added to the reaction mixture, and the resulting solution was extracted with EA (2×75 mL). The organic phase was washed with water (75 mL), brine (75 mL), dried over sodium sulfate, and concentrated. The crude was purified by silica gel column chromatography (PE/EA=1:1) to give compound 3G (6.7 g, 75%).

Step 6: Synthesis of Compound 3

To a solution of compound 3G (7.0 g, 23.9 mmol, 1.0 eq) in $H_2O/CH_3CN$ (35 mL/35 mL) at rt was added 3 N NaOH (16 mL, 47.8 mmol, 2.0 eq). The mixture was stirred at rt for 1.5 h, and TLC showed no 3G was left. Then 3 N HCl was added to adjust the solution to pH~2. The resulting solution was stirred at rt overnight, and lyophilized. The solid was dissolved in water (20 mL) and extracted with EA (5×20 mL). The organic layers were dried and concentrated to give crude compound 3 (5.4 g). The compound was further purified by prep-HPLC (under acidic conditions) to give pure compound 3.

LC-MS: 253 [M+H]$^+$ $^1$H NMR (400 MHz, $CD_3OD$) δ 7.08-7.06 (d, J=8.4 Hz, 1H), 6.43-6.41 (d, J=8.0 Hz, 1H), 3.81-3.78 (m, 1H), 3.77-3.74 (m, 3H), 3.67-3.63 (m, 1H), 2.96 (m, 1H), 0.78-0.76 (m, 2H).

Example 12

Disodium Salt of 4-(formamidomethyl)-2-hydroxy-7-methoxy-3,4-dihydro-1,2-benzoxaborinine-8-carboxylic Acid (Compound 13)

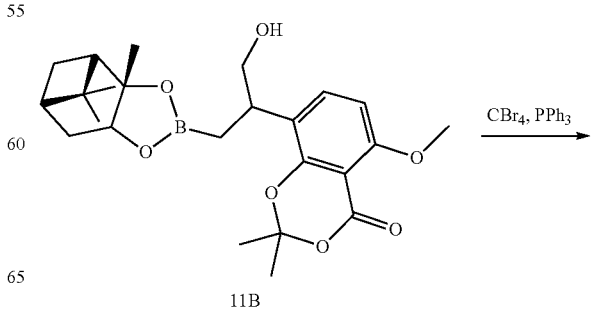

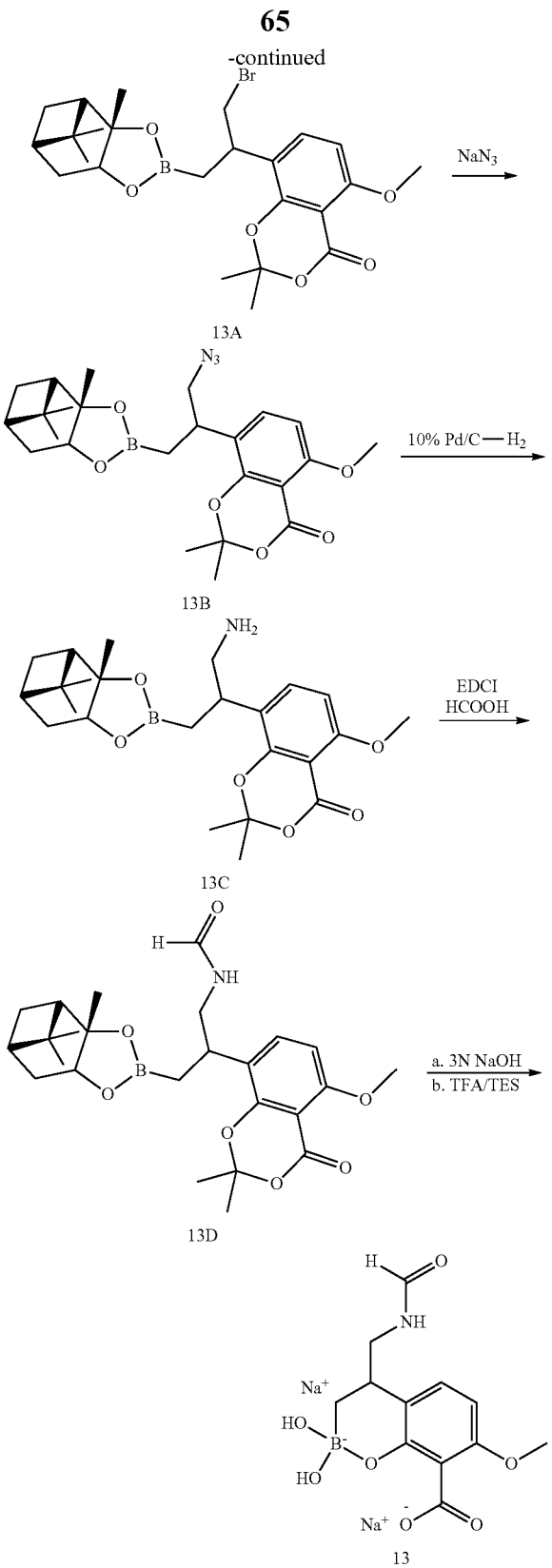

eq) and PPh₃ (1.33 g, 5.07 mmol, 1.5 eq). The mixture was stirred at rt for 2 h under nitrogen atmosphere. Then the mixture was concentrated in vacuum. The residue was purified by column chromatography on silica gel (PE/EA=30:1 to 5:1) to give compound 13A (1.1 g, 64%).

Step 2: Synthesis of Compound 13B

To a solution of compound 13A (280 mg, 0.55 mmol, 1.0 eq) in DMF (8 mL) was added NaN₃ (108 mg, 1.66 mmol, 3.0 eq). The mixture was stirred at 48° C. for 19 h under nitrogen atmosphere. Then the mixture was filtered and the filtrate was diluted with EA. The organic layer was washed water and with brine, dried over Na₂SO₄, and concentrated in vacuum to give crude compound 13B (250 mg, 96%), which was used for next step without further purification.

Step 3: Synthesis of Compound 13C

To a mixture of compound 13B (250 mg, 0.533 mmol, 1.0 eq) in MeOH (30 mL) was added Pd/C (25 mg, 10% w/w) under hydrogen atmosphere. The mixture was stirred at rt for 2 days. Then the mixture was filtered and the filtrate was concentrated in vacuum to give crude compound 13C (220 mg, 93%), which was used for next step without further purification.

Step 4: Synthesis of Compound 13D

To a mixture of compound 13C (500 mg, 1.13 mmol, 1.0 eq) in DCM (10 mL) was added EDCI (433 mg, 2.26 mmol, 2.0 eq), DMAP (14 mg, 0.113 mmol, 0.1 eq), and formic acid (104 mg, 2.26 mmol, 2.0 eq) under $N_2$. The mixture was stirred at rt for 4 h. Then the resulting mixture was purified by prep-HPLC to give compound 13D (230 mg, 45%).

Step 5: Synthesis of Compound 13

To a solution of compound 13D (120 mg, 0.255 mmol, 1.0 eq) in H₂O/ACN (1 mL/1 mL) was added 3 N NaOH (0.17 mL, 0.509 mmol, 2 eq) and the mixture was stirred at rt for 2 h. To the reaction mixture were slowly added TFA (0.06 mL) and TES (0.06 mL), followed by i-BuB(OH)₂ (52 mg, 0.509 mmol, 2 eq). The resulting mixture was stirred at rt for 1 h, concentrated and purified by prep-HPLC (under acidic conditions) to give an acid form of compound 13 (25 mg).

To a solution of the acid form of compound 13 (25 mg, 0.089 mmol, 1.0 eq) in H₂O/ACN (0.2 mL/0.2 mL) was added 3 N NaOH (0.06 mL, 0.18 mmol, 2 eq). The mixture was stirred at rt for 0.5 h, and purified by prep-HPLC (under neutral conditions) to give compound 13 (17 mg, 55%).

LC-MS: 280 [M+H]+; 278 [M−H]⁻

$^1$H NMR (400 MHz, D₂O) δ 8.01 (s, 1H), 7.01-6.99 (d, J=8.4 Hz, 1H), 6.44-6.42 (d, J=8.0 Hz, 1H), 3.75 (s, 3H), 3.51-3.49 (d, J=5.6 Hz, 2H), 2.89-2.85 (m, 1H), 0.63-0.59 (m, 1H), 0.36-0.30 (m, 1H).

Step 1: Synthesis of Compound 13A

To a mixture of compound 11B (1.5 g, 3.38 mmol, 1.0 eq) in DCM (10 mL) was added CBr₄ (1.68 g, 5.07 mmol, 1.5

Example 13

Disodium Salt of 4-(aminomethyl)-2-hydroxy-7-methoxy-3,4-dihydro-1,2-benzoxaborinine-8-carboxylic Acid (Compound 14)

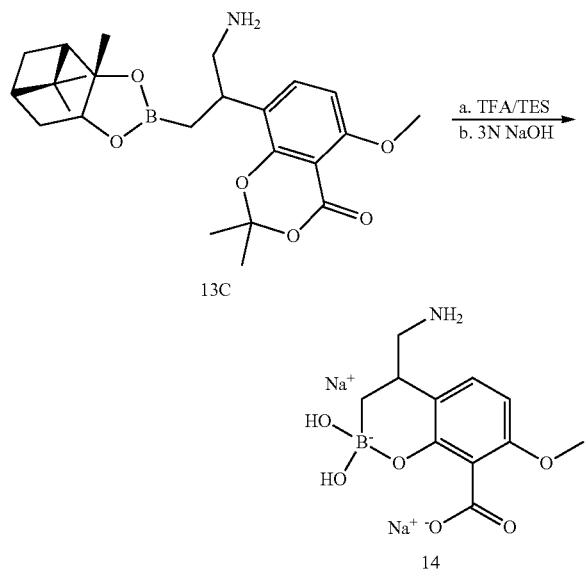

To a solution of compound 13C (180 mg, 0.406 mmol, 1.0 eq) in H$_2$O/ACN (1 mL/1 mL) was added TFA (0.2 mL) and TES (0.2 mL), followed by i-BuB(OH)$_2$ (83 mg, 0.812 mmol, 2 eq). The mixture was stirred at rt for 5 h. The reaction mixture was concentrated under reduced pressure. The resulting residue was dissolved in CH$_3$CN/H$_2$O and the pH of the solution was adjusted with 3 N NaOH to pH~10. The mixture was purified by prep-HPLC (under neutral conditions) to give compound 14 (30 mg, 29%).

LC-MS: 252 [M+H]$^+$ $^1$H NMR (400 MHz, D$_2$O) δ 6.95-6.93 (d, J=8.4 Hz, 1H), 6.41-6.39 (d, J=8.8 Hz, 1H), 3.71 (s, 3H), 3.15-3.07 (m, 3H), 0.62-0.60 (m, 1H), 0.45-0.41 (m, 1H).

Example 14

Disodium Salt of 4-(Azidomethyl)-2-hydroxy-7-methoxy-3,4-dihydro-1,2-benzoxaborinine-8-carboxylic Acid (Compound 15)

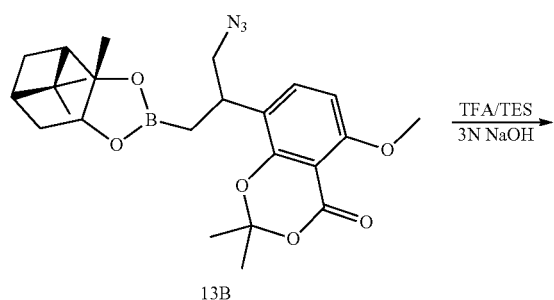

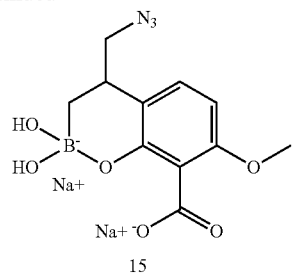

To a solution of compound 13B (200 mg, 0.255 mmol, 1.0 eq) in H$_2$O/ACN (0.5 mL/0.5 mL) was added TFA (0.06 mL) and TES (0.06 mL), followed by i-BuB(OH)$_2$ (87 mg, 0.853 mmol, 2 eq). The mixture was stirred at 27° C. for 8 h. The reaction mixture was subsequently concentrated at rt and 3 N NaOH (0.28 mL, 0.84 mmol, 2 eq) was added to the crude. The mixture was stirred at rt overnight, concentrated, and purified by prep-HPLC (under neutral conditions) to give compound 15 (39 mg, 33%).

LC-MS: 278 [M+H]$^+$, 555 [2M+H]$^+$, and 535 [2M−H]$^−$ $^1$H NMR (400 MHz, D$_2$O) δ 7.03-7.01 (d, J=8.0 Hz, 1H), 6.45-6.42 (d, J=8.4 Hz, 1H), 3.72 (s, 3H), 3.58-3.52 (m, 2H), 2.92 (m, 1H), 0.73-0.71 (m, 1H), 0.48 (m, 1H).

Example 15

Disodium Salt of 2-hydroxy-4-[[4-(hydroxymethyl)triazol-1-yl]methyl]-7-methoxy-3,4-dihydro-1,2-benzoxaborinine-8-carboxylic Acid (Compound 16)

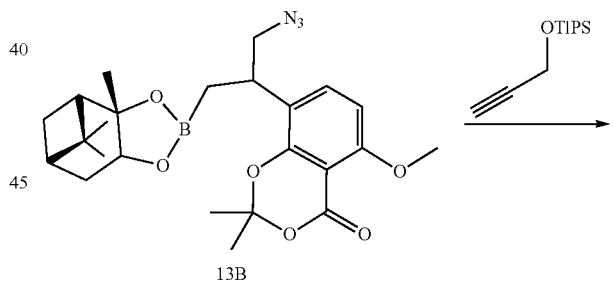

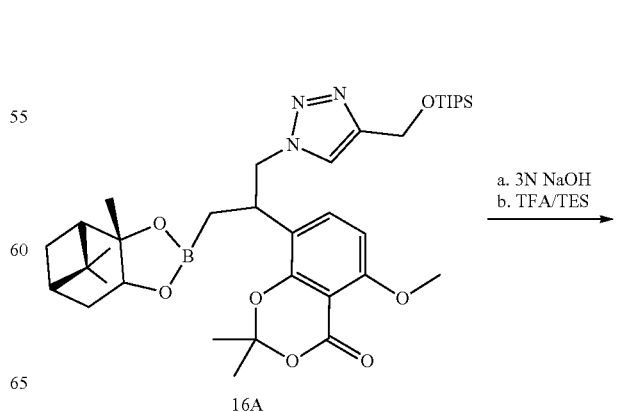

69

-continued

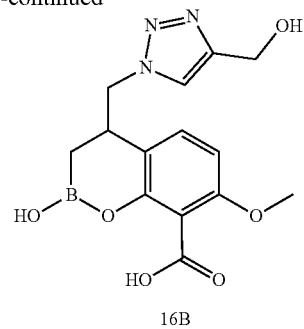

16B

| 3N NaOH

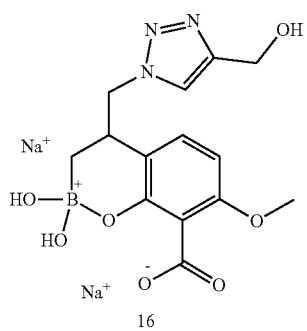

16

Step 1: Synthesis of Compound 16A

To a solution of compound 13B (140 mg, 0.30 mmol, 1.0 eq) in 1,2-dichlorobenzene (2 mL) was added triisopropyl (prop-2-ynoxy)silane (127 mg, 0.60 mmol, 2.0 eq). The reaction was stirred at 120° C. overnight under nitrogen atmosphere. The resulting mixture was concentrated under vacuum. The residue was purified by prep-TLC (PE/EA=1:1) to give compound 16A (80 mg, 51%).

Step 2: Synthesis of Compound 16

To a solution of compound 16A (80 mg, 0.12 mmol, 1.0 eq) in H$_2$O/ACN (1 mL/1 mL) was added 3 N NaOH (0.12 mL, 0.36 mmol, 3 eq). The mixture was stirred at rt overnight, followed by a slow addition of TFA (1 mL), TES (1 mL), and i-BuB(OH)$_2$ (23 mg, 0.235 mmol, 2 eq). The reaction was stirred at rt for an additional 1 h, concentrated, and purified by prep-HPLC (under acidic conditions) to give compound 16B (27 mg) in acid form. To a solution of the compound 16B acid (27 mg, 0.081 mmol, 1.0 eq) in H$_2$O/ACN (0.2 mL/0.2 mL) was added 3 N NaOH (0.06 mL, 0.18 mmol, 2 eq). The mixture was stirred at rt for 30 min, then triturated with H$_2$O/acetone (1:20) to give compound 16 (17 mg, 53%).

LC-MS: 334 [M+H]$^+$ $^1$H NMR (400 MHz, CD$_3$OD) δ 7.58 (s, 1H), 6.40-6.38 (d, J=8.4 Hz, 1H), 6.15-6.13 (d, J=8.4 Hz, 1H), 4.64-4.61 (m, 3H), 4.46 (m, 1H), 3.69 (s, 3H), 3.22-3.19 (m, 1H), 0.51-0.49 (d, J=5.6 Hz, 2H).

70

Example 16

Disodium Salt of 4-(acetamidomethyl)-2-hydroxy-7-methoxy-3,4-dihydro-1,2-benzoxaborinine-8-carboxylic Acid (Compound 17)

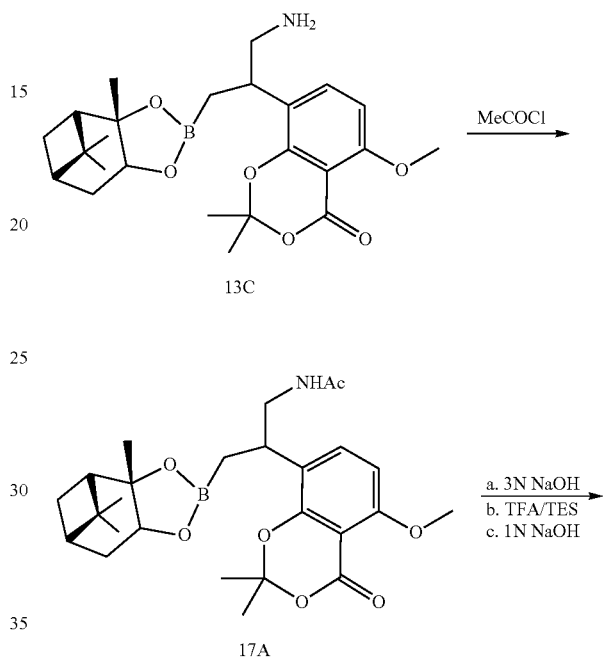

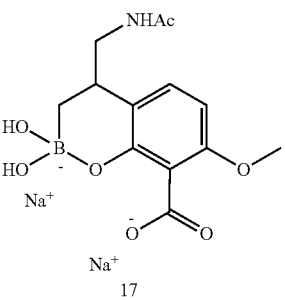

17

Step 1: Synthesis of Compound 17A

To a mixture of compound 13C (150 mg, 0.34 mmol, 1.0 eq) in DCM (5 mL) was added acetyl chloride (52 mg, 0.68 mmol, 2.0 eq) and triethylamine (0.14 mL, 1.02 mmol, 3.0 eq) under N$_2$. The reaction was stirred at rt for 1 h. The resulting mixture was diluted with DCM and washed with water to give crude compound 17A (160 mg, 92%), which was used for next step without further purification.

Step 2: Synthesis of Compound 17

To a solution of compound 17A (150 mg, 0.31 mmol, 1.0 eq) in H$_2$O/ACN (1.5 mL/1.5 mL) was added 3 N NaOH (0.31 mL, 0.93 mmol, 3 eq). The mixture was stirred at rt for 3 h, then TFA (1.5 mL) and TES (1.5 mL) were slowly added, followed by i-BuB(OH)$_2$ (62 mg, 0.62 mmol, 2 eq). The resulting mixture was stirred at rt for 1 h, then purified by prep-HPLC (under acidic conditions) to give an acid form of 17. To a solution of the acid form of 17 (62 mg, 0.21 mmol, 1.0 eq) in H$_2$O/ACN (0.2 mL/0.2 mL) was added 1 N NaOH (0.41 mL, 0.41 mmol, 2 eq). The mixture was stirred at rt for 30 min, and lyophilized. The solid was triturated with a solution of water and acetone (1:20), and dried to give compound 17 (40 mg, 22%).

LC-MS: 294 [M+H]$^+$, 292 [M−H]$^−$ $^1$H NMR (400 MHz, CD$_3$OD) δ 6.83-6.82 (d, J=8.0 Hz, 1H), 6.26-6.24 (d, J=8.4 Hz, 1H), 3.77 (s, 3H), 3.39-3.38 (m, 2H), 2.88-2.85 (m, 1H), 1.88-1.86 (m, 3H), 0.63-0.58 (dd, J=6.8 Hz and 6.0 Hz, 1H), 0.49-0.44 (dd, J=5.2 Hz and 5.2 Hz, 1H).

Example 17

Potentiation of Aztreonam

The potency and spectrum of β-lactamase inhibitors (BLIs) was determined by assessing their aztreonam potentiation activity in a dose titration potentiation assay using strains of various bacteria that are resistant to aztreonam due to expression of various β-lactamases. Aztreonam is a monobactam antibiotic and is hydrolyzed by the majority of β-lactamases that belong to class A or C (but not class B or D). The potentiation effect was observed as the ability of BLI compounds to inhibit growth in the presence of sub-inhibitory concentration of aztreonam. MICs of test strains varied from 64 μg/mL to >128 μg/mL. Aztreonam was present in the test medium at 4 μg/mL. Compounds were tested at concentrations up to 20 μg/mL. In this assay, potency of compounds was reported as the minimum concentration of BLI required to inhibit growth of bacteria in the presence of 4 μg/mL of aztreonam (MPC$_{@4}$). Table 1 summarizes the BLI potency of aztreonam potentiation (MPC$_{@4}$) for various strains overexpressing class A (ESBL and KPC), and class C β-lactamases. Aztreonam MIC for each strain is also shown.

TABLE 1

Activity of BLIs to potentiate aztreonam against strains expressing class A and class C enzymes.

| Compound | Aztreonam MIC (μg/mL) | | | | | | | |
|---|---|---|---|---|---|---|---|---|
| | >128 AZT MPC4 CTX-M-14 KP1005 | >128 AZT MPC4 CTX-M-15 KP1009 | >128 AZT MPC4 SHV-5 ec308 | 64 AZT MPC4 SHV-12 KP1010 | 128 AZT MPC4 TEM-10 ec302 | >128 AZT MPC4 KPC-2 KP1004 | 64 AZT MPC4 ECL1002 | >128 AZT MPC4 CMY-6 EC1010 |
| 1 | Z | Y | Y | X | Y | X | Y | X |
| 2 | Z | Z | X | X | Y | Y | Y | Y |
| 3 | X | X | X | X | X | X | X | X |
| 4 | X | X | X | X | X | X | X | X |
| 5 | X | X | X | X | X | X | X | X |
| 6 | X | X | X | X | X | X | X | X |
| 7 | X | X | X | X | X | X | X | X |
| 8 | X | X | X | X | X | X | X | X |
| 9 | X | X | X | X | X | X | X | X |
| 10 | Z | Z | X | X | X | X | Y | Y |
| 11 | X | X | X | X | X | X | X | X |
| 12 | Z | Z | X | X | Z | X | Y | Y |
| 13 | X | X | X | X | X | X | X | X |
| 14 | Y | Y | Y | Y | Y | X | Y | Y |
| 15 | X | X | X | X | X | X | X | X |
| 16 | X | X | X | X | X | X | X | X |
| 17 | Y | X | X | X | X | X | X | X |
| Tazobactam | Y | Y | Y | X | X | Z | Z | Y |
| Clavulanic Acid | X | X | X | X | X | Z | Z | Z |

X = MPC$_{@4}$ ≤ 5 μg/mL
Y = 5 μg/mL < MPC$_{@4}$ ≤ 20 μg/mL
Z = MPC$_{@4}$ > 20 μg/mL

Example 18

Potentiation of Tigemonam

Selected β-lactamase inhibitors were also tested for their ability to potentiate the monobactam tigemonam. The potentiation effect was observed as the ability of BLI compounds to inhibit growth in the presence of sub-inhibitory concentration of tigemonam. MICs of test strains varied from 16 μg/mL to >64 μg/mL. Tigemonam was present in the test medium at 4 μg/mL. Compounds were tested at concentrations up to 20 μg/mL. In this assay, potency of compounds was reported as the minimum concentration of BLI required to inhibit growth of bacteria in the presence of 4 μg/mL of tigemonam (MPC$_{@4}$). Table 2 summarizes the BLI potency of tigemonam potentiation (MPC$_{@4}$) for various strains overexpressing class A (ESBL) and class C β-lactamases. Tigemonam MIC for each strain is also shown.

TABLE 2

Activity of BLIs to potentiate tigemonam against strains expressing class A and class C enzymes.
Table 2.

| Compound | Tigemonam MIC (µg/mL) | | | | | | |
|---|---|---|---|---|---|---|---|
| | >64 TIG $MPC_4$ CTX-M-14 KP1005 | >64 TIG $MPC_4$ CTX-M-15 KP1009 | >64 TIG $MPC_4$ SHV-5 ec308 | >64 TIG $MPC_4$ SHV-12 KP1010 | >64 TIG $MPC_4$ TEM-10 ec302 | 32 TIG $MPC_4$ ECL1002 | 16 TIG $MPC_4$ CMY-6 EC1010 |
| 1 | Z | Z | Z | Z | Z | X | X |
| 2 | Z | Z | Y | Y | Z | X | X |
| 3 | X | X | X | X | X | X | X |
| 4 | Y | X | X | X | Y | X | X |
| 5 | X | X | X | X | X | X | X |
| 6 | X | X | X | X | X | X | X |
| 7 | Y | X | X | X | X | X | X |
| 8 | X | X | X | X | X | X | X |
| 9 | Y | X | X | X | X | X | X |
| 10 | Z | Z | X | X | Y | X | X |
| 11 | X | X | X | X | X | X | X |
| 12 | Z | Z | Z | Y | Z | X | X |
| 13 | Y | X | X | X | Y | X | X |
| 14 | Z | Z | Z | Y | Z | X | X |
| 15 | X | X | X | X | X | X | X |
| 16 | Y | X | X | X | Y | X | X |
| 17 | Y | X | X | X | Y | X | X |
| Tazobactam | Y | Y | X | X | X | Y | X |
| Clavulanic Acid | X | X | X | X | X | Z | Z |

X = $MPC_{@4}$ ≤ 5 µg/mL
Y = 5 µg/mL < $MPC_{@4}$ ≤ 20 µg/mL
Z = $MPC_{@4}$ > 20 µg/mL

Example 19

Potentiation of Biapenem

β-lactamase inhibitors were also tested for their ability to potentiate the carbapenem biapenem against strains producing class A (KPC), class D (OXA-48), and class B (metallo β-lactamases, NDM-1 and VIM-1) carbapenemases. The potentiation effect was observed as the ability of BLI compounds to inhibit growth in the presence of a sub-inhibitory concentration of biapenem. Biapenem MIC of test strains were 16-32 µg/mL. Biapenem was present in the test medium at 1 µg/mL. Compounds were tested at concentrations up to 20 µg/mL. In this assay, potency of compounds was reported as the minimum concentration of BLI required to inhibit growth of bacteria in the presence of 1 µg/mL of biapenem ($MPC_{@1}$). Table 3 summarizes the BLI potency of biapenem potentiation ($MPC_{@1}$) for four strains overexpressing class A (KPC), class D (OXA-48), and class B (NDM-1 and VIM-1) carbapenemases. Biapenem MIC for each strain is also shown.

TABLE 3

Activity of BLIs to potentiate biapenem against strains expressing class A (KPC), class D (OXA-48), and class B (NDM-1 and VIM-1) cabapenemases.
Table 3.

| Compound | Biapenem MIC (µg/mL) | | | |
|---|---|---|---|---|
| | 32 BPM $MPC_1$ KP1004 KPC-2 | 16 BPM $MPC_1$ OXA-48 KP1086 | 16 BPM $MPC_1$ KP1081 NDM-1 | 16 BPM $MPC_1$ KP1054 VIM-1 |
| 1 | X | X | X | Z |
| 2 | X | X | Z | Z |
| 3 | X | X | X | Y |
| 4 | X | X | X | Y |
| 5 | X | X | Y | Z |
| 6 | X | X | X | Y |
| 7 | X | X | X | Y |
| 8 | X | X | Y | Z |
| 9 | X | X | X | Z |
| 10 | X | X | Z | Z |
| 11 | X | X | X | Y |
| 12 | X | X | Y | Z |
| 13 | X | X | X | Y |
| 14 | X | Y | X | Z |
| 15 | X | X | X | Y |
| 16 | X | Y | Y | Y |
| 17 | X | Y | Y | Y |
| Tazobactam | Z | Y | Z | Z |
| Clavulanic Acid | Y | Z | Z | Z |

X = $MPC_{@1}$ ≤ 5 µg/mL
Y = 5 µg/mL < $MPC_{@1}$ ≤ 20 µg/mL
Z = $MPC_{@1}$ > 20 µg/mL

Example 20

Potentiation of Meropenem

β-lactamase inhibitors were also tested for their ability to potentiate the carbapenem meropenem against strains of *Acinetobacter baumannii* producing class D (OXA-23 and OXA-72) carbapenemases. The potentiation effect was observed as the ability of BLI compounds to inhibit growth in the presence of a sub-inhibitory concentration of meropenem. Meropenem MIC of test strains were 32 to >64 µg/mL. Meropenem was present in the test medium at 8 µg/mL. Compounds were tested at concentrations up to 20 µg/mL. In this assay, potency of compounds was reported as the minimum concentration of BLI required to inhibit growth of bacteria in the presence of 8 µg/mL of meropenem ($MPC_{@8}$). Table 4 summarizes the BLI potency of meropenem potentiation ($MPC_{@8}$) for two strains overexpressing OXA-72 and OXA-23 carbapenemases. Meropenem MIC for each strain is also shown.

TABLE 4

Activity of BLIs to potentiate meropenem against strains expressing class D carbapenemases from Acinetobacter baumannii
Table 4.

| | Meropenem MIC (µg/mL) | |
|---|---|---|
| | >64 MPM $MPC_8$ AB1053 | 32 MPM $MPC_8$ AB1054 |
| Compound | OXA-72 | OXA-23 |
| 1 | Z | Z |
| 2 | Y | Y |
| 3 | X | X |
| 4 | X | X |
| 5 | X | X |
| 6 | X | X |
| 7 | Y | Y |
| 8 | X | X |
| 9 | X | Y |
| 10 | Z | Z |
| 11 | X | X |
| 12 | X | Y |
| 13 | X | X |
| 14 | Y | Z |
| 15 | X | X |
| 16 | X | Y |
| 17 | X | Y |

X = $MPC_{@1}$ ≤ 5 µg/mL
Y = 5 µg/mL < $MPC_{@1}$ ≤ 20 µg/mL
Z = $MPC_{@1}$ > 20 µg/mL

What is claimed is:

1. A compound having the structure of Formula (Ic) or Formula (IIc):

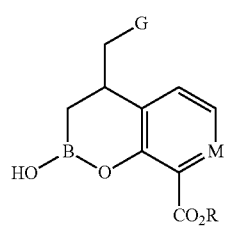
(Ic)

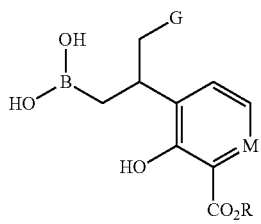
(IIc)

or a pharmaceutically acceptable salt thereof, wherein:

G is selected from the group consisting of —OH, -OMe, -OBn, —CH$_2$OH, N$_3$, NH$_2$, —NHC(=O)H, —NHC(=O)CH$_3$, and

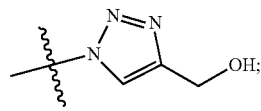 [SMILES: *n1cc(CO)nn1]

M is selected from the group consisting of —CR$^7$ and N;
R$^7$ is selected from the group consisting of —H, —OR$^8$, and halogen;
R$^8$ is C$_{1-4}$ alkyl; and
R is —H.

2. The compound of claim 1, wherein G is selected from the group consisting of —OH and —OBn.

3. The compound of claim 1, wherein G is —OH.

4. The compound of claim 1, wherein M is selected from the group consisting of —CH, —COMe, CF, and N.

5. The compound of claim 1, wherein M is —COMe.

6. The compound of claim 1, having the structure selected from the group consisting of:

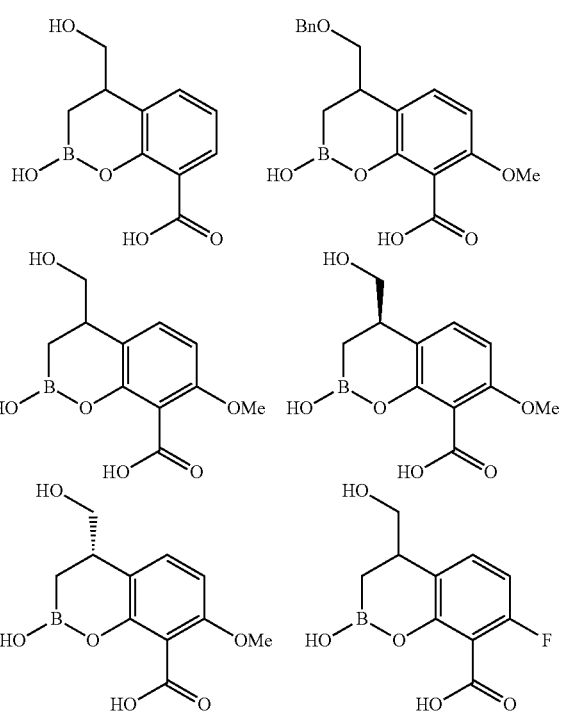

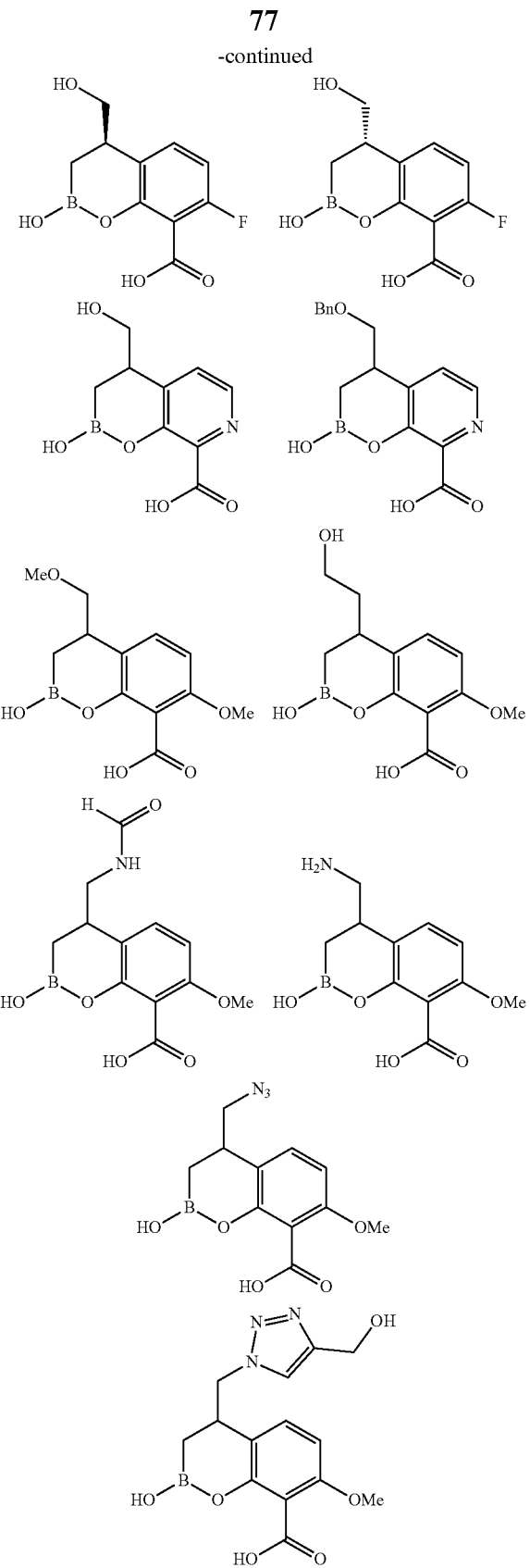

and pharmaceutically acceptable salts thereof.

7. A pharmaceutical composition comprising a therapeutically effective amount of a compound of claim 1 and a pharmaceutically acceptable excipient.

8. The pharmaceutical composition of claim 7, further comprising an additional medicament.

9. The composition of claim 8, wherein the additional medicament is selected from the group consisting of an antibacterial agent, an antifungal agent, an antiviral agent, an anti-inflammatory agent, and an anti-allergic agent.

10. The composition of claim 9, wherein the additional medicament is a β-lactam antibacterial agent.

11. The composition of claim 10, wherein the β-lactam antibacterial agent is selected from the group consisting of Amoxicillin, Ampicillin (Pivampicillin, Hetacillin, Bacampicillin, Metampicillin, Talampicillin), Epicillin, Carbenicillin (Carindacillin), Ticarcillin, Temocillin, Azlocillin, Piperacillin, Mezlocillin, Mecillinam (Pivmecillinam), Sulbenicillin, Benzylpenicillin (G), Clometocillin, Benzathine benzylpenicillin, Procaine benzylpenicillin, Azidocillin, Penamecillin, Phenoxymethylpenicillin (V), Propicillin, Benzathine phenoxymethylpenicillin, Pheneticillin, Cloxacillin (Dicloxacillin, Flucloxacillin), Oxacillin, Meticillin, Nafcillin, Faropenem, Tomopenem, Razupenem, Cefazolin, Cefacetrile, Cefadroxil, Cefalexin, Cefaloglycin, Cefalonium, Cefaloridine, Cefalotin, Cefapirin, Cefatrizine, Cefazedone, Cefazaflur, Cefradine, Cefroxadine, Ceftezole, Cefaclor, Cefamandole, Cefminox, Cefonicid, Ceforanide, Cefotiam, Cefprozil, Cefbuperazone, Cefuroxime, Cefuzonam, Cefoxitin, Cefotetan, Cefmetazole, Loracarbef, Cefixime, Ceftriaxone, Cefcapene, Cefdaloxime, Cefdinir, Cefditoren, Cefetamet, Cefmenoxime, Cefodizime, Cefoperazone, Cefotaxime, Cefpimizole, Cefpiramide, Cefpodoxime, Cefsulodin, Cefteram, Ceftibuten, Ceftiolene, Ceftizoxime, Flomoxef, Latamoxef, Cefepime, Cefozopran, Cefpirome, Cefquinome, Ceftobiprole, Ceftaroline, CXA-101, RWJ-54428, MC-04,546, ME1036, Ceftiofur, Cefquinome, Cefovecin, RWJ-442831, RWJ-333441, and RWJ-333442.

12. The composition of claim 10, wherein the β-lactam antibacterial agent is selected from the group consisting of Ceftazidime, Biapenem, Doripenem, Ertapenem, Imipenem, Meropenem, Tebipenem, Tebipenem pivoxil, Apapenem, and Panipenem.

13. The composition of claim 10, wherein the β-lactam antibacterial agent is selected from Aztreonam, Tigemonam, BAL30072, SYN 2416, or Carumonam.

14. The compound of claim 1, having a structure selected from:
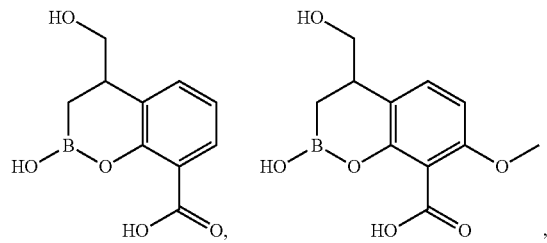
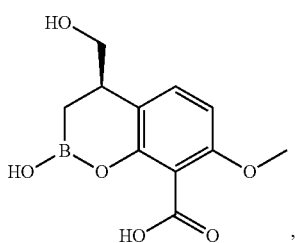
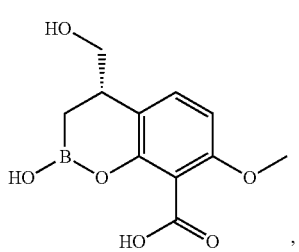
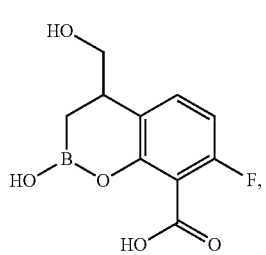
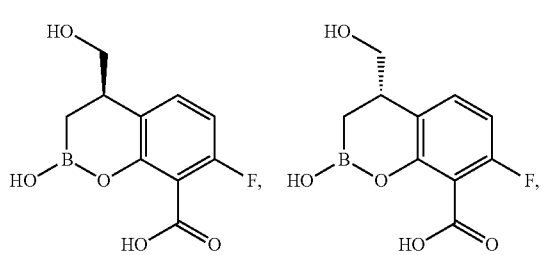
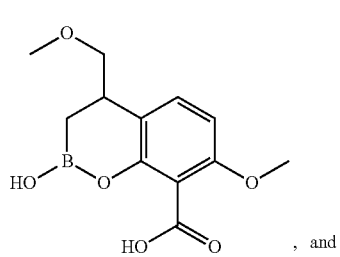, and
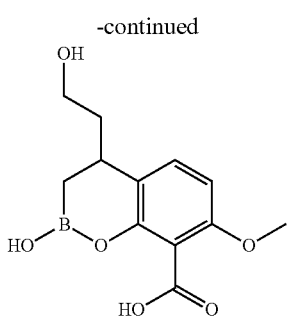
and pharmaceutically acceptable salts thereof.
15. The compound of claim 1, having a structure selected from:
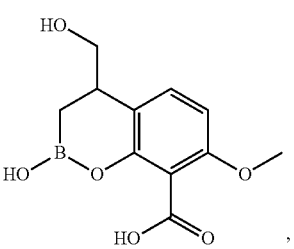
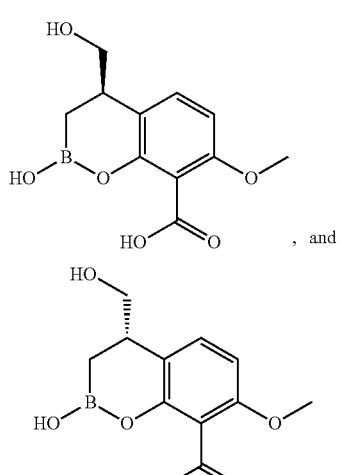, and
and pharmaceutically acceptable salts thereof.
16. The compound of claim 1, having the structure of
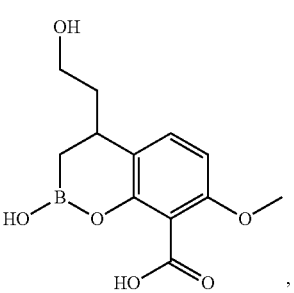 [SMILES: COc1ccc2c(c1C(=O)O)OB(O)CC2CCO],
or a pharmaceutically acceptable salt thereof.

17. The compound of claim 1, having a structure selected from:

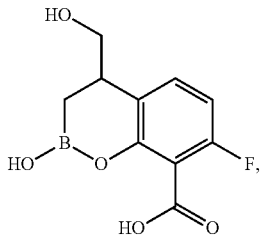

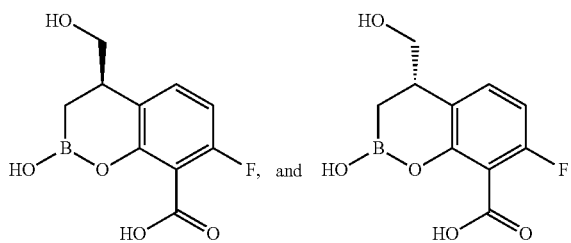

and pharmaceutically acceptable salts thereof.

18. The compound of claim 1, having the structure of:

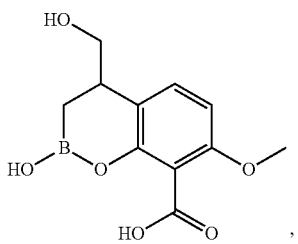

or a pharmaceutically acceptable salt thereof.

19. The compound of claim 1, having the structure of:

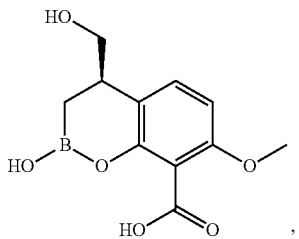 [SMILES: COc1ccc2c(c1C(=O)O)OB(O)C[C@H]2CO]

or a pharmaceutically acceptable salt thereof.

20. The compound of claim 1, having the structure of:

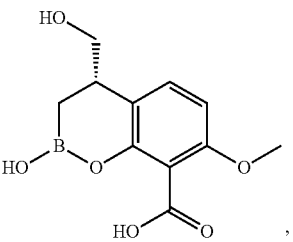 [SMILES: COc1ccc2c(c1C(=O)O)OB(O)C[C@@H]2CO]

or a pharmaceutically acceptable salt thereof.

21. The compound of claim 1, having the structure of:

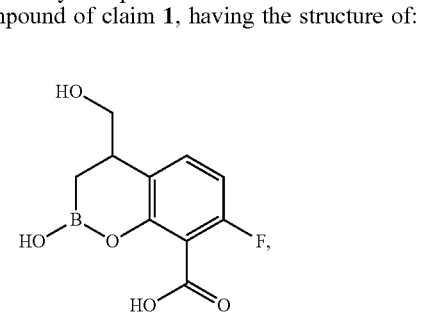

or a pharmaceutically acceptable salt thereof.

22. The compound of claim 1, having the structure of:

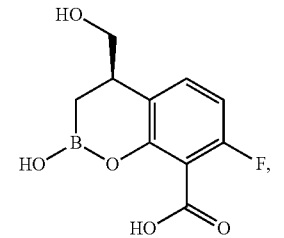 [SMILES: O=C(O)c1c(F)ccc2c1OB(O)C[C@H]2CO]

or a pharmaceutically acceptable salt thereof.

23. The compound of claim 1, having the structure of:

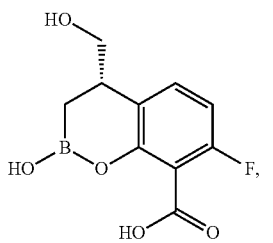 [SMILES: O=C(O)c1c(F)ccc2c1OB(O)C[C@@H]2CO]

or a pharmaceutically acceptable salt thereof.

* * * * *